US009718873B2

(12) United States Patent
Whittle et al.

(10) Patent No.: US 9,718,873 B2
(45) Date of Patent: Aug. 1, 2017

(54) BROADLY NEUTRALIZING HUMAN ANTIBODY THAT RECOGNIZES THE RECEPTOR-BINDING POCKET OF INFLUENZA HEMAGGLUTININ

(71) Applicants: Children's Hospital Boston, Boston, MA (US); Duke University, Durham, NC (US)

(72) Inventors: James Whittle, Boston, MA (US); Stephen C. Harrison, Brighton, MA (US); Barton F. Haynes, Durham, NC (US); Hua-Xin Liao, Durham, NC (US); M. A. Moody, Durham, NC (US); Thomas B. Kepler, Durham, NC (US); Aaron G. Schmidt, Boston, MA (US)

(73) Assignees: Duke University, Durham, NC (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/171,322

(22) Filed: Feb. 3, 2014

(65) Prior Publication Data

US 2014/0302043 A1    Oct. 9, 2014

Related U.S. Application Data

(63) Continuation-in-part of application No. PCT/US2012/049573, filed on Aug. 3, 2012.

(60) Provisional application No. 61/514,662, filed on Aug. 3, 2011.

(51) Int. Cl.
| | | |
|---|---|---|
| C07K 16/10 | (2006.01) | |
| A61K 38/02 | (2006.01) | |
| A61K 31/713 | (2006.01) | |
| A61K 47/48 | (2006.01) | |
| A61K 51/10 | (2006.01) | |

(52) U.S. Cl.
CPC ........ *C07K 16/1018* (2013.01); *A61K 31/713* (2013.01); *A61K 38/02* (2013.01); *A61K 47/4853* (2013.01); *A61K 51/1006* (2013.01); *C07K 2299/00* (2013.01); *C07K 2317/33* (2013.01); *C07K 2317/55* (2013.01); *C07K 2317/565* (2013.01); *C07K 2317/76* (2013.01)

(58) Field of Classification Search
None
See application file for complete search history.

(56) References Cited

U.S. PATENT DOCUMENTS 8,591,914 B2 * 11/2013 Yang et al. ................ 424/211.1
8,900,590 B2 * 12/2014 Olsen et al. ................ 424/178.1

FOREIGN PATENT DOCUMENTS

BE    WO 2009/147248 A2 * 12/2009 ........... A61K 39/395

OTHER PUBLICATIONS

Yoshida et al. (PLoS Pathogens, Mar. 2009, vol. 5, p. 1-9).*
Lim et al. (Virology Journal, 2008, vol. 5, p. 1-4).*
Whittle et al. (PNAS, 2011, vol. 108, p. 14216-14221).*

* cited by examiner

*Primary Examiner* — Agnieszka Boesen
(74) *Attorney, Agent, or Firm* — Mintz Levin Cohn Ferris Glovsky and Popeo, P.C.; Peter F. Corless; Christopher R. Cowles

(57) ABSTRACT

The invention features a novel influenza antibody that specifically binds to influenza hemagglutinin and reduces or inhibits hemagglutinin binding to sialic acid. The invention also provides methods, compositions, and kits featuring the novel antibody and its use in preventing or treating influenza infection.

22 Claims, 23 Drawing Sheets

Heavy chain DNA sequences:

CL860UCA_VH  [SEQ ID NO: 1]
CAGGTGCAGCTGGTGCAGTCTGGGGCTGAGGTGAAGAAGCCTGGGGCCTCAGTGAAGGTCTCCTGCAAGGCTTCT
GGATACACCTTCACCGGCTACTATATGCACTGGGTGCGACAGGCCCCTGGACAAGGGCTTGAGTGGATGGGATGG
ATCAACCCTAACAGTGGTGGCACAAACTATGCACAGAAGTTTCAGGGCTGGGTCACCATGACCAGGGACACGTCC
ATCAGCACAGCCTACATGGAGCTGAGCAGGCTGAGATCTGACGACACGGCCGTGTATTACTGTGCGAGAGGGGGA
CTGGAACCcCGATCTGTAGACTACTACTACTACGGTATGGACGTCTGGGGCCAAGGGACCACGGTCACCGTCTCC
TCA

CH65_VH  [SEQ ID NO: 2]
GAAGTGCAGCTGGTGCAGTCTGGAGCTGAGGTGAAGAAGCCTGGGGCCTCAGTGAAAGTCTCCTGCAAGGCTTCT
GGATACACCTTCACCGACTATCATATAAACTGGGTGCGACAGGCCCCTGGACAAGGGCTTGAGTGGATGGGATGG
ATCCACCCTAACAGTGGTGACACAAACTATGCACAGAAGTTTCAGGGCTGGGTCACCATGACCAGGGACACGGCC
ATCAGCACAGCCTACATGGAGGTGAATGGCTTGAAATCTGACGACACGGCCGTGTATTATTGTGCGAGAGGGGGA
CTGGAACCCCGATCTGTAGACTACTACTATTATGGTATGGACGTCTGGGGCCAAGGGACCACGGTCACCGTCTCC
TCA

CH66_VH  [SEQ ID NO: 3]
CAGGTGCAGCTGGTGCAGTCTGGGGCTGAGGTGAAGAAGCCTGGGGCCTCAGTGAAAGTCTCCTGCAAGGCTTCT
GGATACACCTTCACCGACTATCATATAAACTGGGTGCGACAGGCCCCTGGACAAGGGCTTGAGTGGATGGGATGG
ATCCACCCTAACAGTGGTGACACAAACTATGCACAGAAGTTTCAGGGCTGGGTCACCATGACCAGGGACACGTCC
ATCAGCACAGCCTACATGGAGGTGAATGGCTTGAAATCTGACGACACGGCCGTGTATTATTGTGCGAGAGGGGGA
CTGGAACCTCGATCTGTAGACTACTACTATTATGGTATGGACGTCTGGGGCCAAGGGACCACGGTCACCGTCTCC
TCA

CH67_VH  [SEQ ID NO: 4]
CAGGTGCAGCTGGTGCAGTCTGGGGCTGAGGTGAGGAAGCCTGGGGCCTCAGTGAAGGTCTCCTGCAAGGCTTCT
GGATACACCTTCACCGACAACTATATACACTGGGTGCGACAGGCCCCTGGACAAGGGCTTGAGTGGATGGGATGG
ATCCACCCTAACAGTGGTGCCACAAAGTATGCACAGAAGTTTGAGGGCTGGGTCACCATGACCAGGGACACGTCA
ATCAGCACAGTCTACATGGAACTGAGCAGATCGAGATCTGACGACACGGCCGTATATTACTGTGCGAGAGCGGGA
CTGGAACCACGATCCGTAGACTACTACTTCTACGGTTTGGACGTCTGGGGCCAAGGGACCGCGGTCACCGTCTCC
TCA

Figure 7

Light chain DNA sequences:

CL860UCA_VL  [SEQ ID NO: 5]
CAGTCTGTGCTGACTCAGCCACCCTCGGTGTCAGTGGCCCCAGGACAGACGGCCAGGATTACCTGTGGGGGAAAC
AACATTGGAAGTAAAAGTGTGCACTGGTACCAGCAGAAGCCAGGCCAGGCCCCTGTGCTGGTCGTCTATGATGAT
AGCGACCGGCCCTCAGGGATCCCTGAGCGATTCTCTGGCTCCAACTCTGGGAACACGGCCACCCTGACCATCAGC
AGGGTCGAAGCCGGGGATGAGGCCGACTATTACTGTCAGGTGTGGGATAGTAGTAGTGATCATGTGGTATTCGGC
GGAGGGACCAAGCTGACCGTCCTA

CH65_VL  [SEQ ID NO: 6]
CAGTCTGTGCTGACTCAGCCACCCTCGGTGTCAGTGGCCCCAGGGCAGACGGCCAGGATTACCTGTGGGGGAAAT
GATATTGGAAGGAAGAGTGTGCACTGGAACCAGCAGAAGCCAGGCCAGGCCCCTGTGCTGGTCGTCTGTTATGAT
AGCGACCGGCCCTCAGGGATCCCTGAGCGATTCTCTGGCTCCAATTCAGGGAACACGGCCACCCTGACCATCAGT
AGGGTCGAAGCCGGGGATGAGGCCGACTATTATTGTCAGGTGTGGGATAGTAGTAGTGATCATGTGATATTCGGC
GGAGGGACCAAGCTGACCGTCCTA

CH66_VL  [SEQ ID NO: 7]
CAGTCTGCCCTGACTCAGCCACCCTCGGTGTCAGTGGCCCCAGGGCAGACGGCCAGGATTACCTGTGGGGGAAAT
GATATTGGAAGGAAGAGTGTGCACTGGAACCAGCAGAAGCCAGGCCAGGCCCCTGTGCTGGTCGTCTGTTATGAT
AGTGACCGGCCCTCAGGGATCCCTGAGCGATTCTCTGGCTCCAATTCAGGGAACACGGCCACCCTGACCATCAGC
AGGGTCGAAGCCGGGGATGAGGCCGACTATTATTGTCAGGTGTGGGATAGTAGTAGTGATCATGTGGTATTCGGC
GGAGGGACCAAGCTGACCGTCCTA

CH67_VL  [SEQ ID NO: 8]
CAGTCTGCCCTGACTCAGCCACCCTCGGTGTCAGTGGCCCCAGGACAGACGGCCACGATTACCTGTGGGGGAAAC
AACATTGGACGTAAAAGAGTGGACTGGTTCCAGCAGAAGCCAGGCCAGGCCCCTGTGCTGGTCGTCTATGAGGAT
AGCGACCGGCCCTCAGGGATCCCTGAGCGATTCTCTGACTCCAACTCTGGGACCACGGCCACCCTGACCATCAGC
AGGGTCGAAGCCGGGGATGAGGCCGACTATTACTGTCAGGTGTGGGATAGTGATAGTGATCATGTGGTATTCGGC
GGAGGGACCAAACTGACCGTCCTA

Figure 8

Heavy chain amino acid sequences:

CL860UCA_VH   [SEQ ID NO: 9]
QVQLVQSGAEVKKPGASVKVSCKASGYTFTGYYMHWVRQAPGQGLEWMGWINPNSGGTNYAQKFQGWVTMTRDTS
ISTAYMELSRLRSDDTAVYYCARGGLEPRSVDYYYYGMDVWGQGTTVTVSS

CH65_VH   [SEQ ID NO: 10]
EVQLVQSGAEVKKPGASVKVSCKASGYTFTDYHINWVRQAPGQGLEWMGWIHPNSGDTNYAQKFQGWVTMTRDTA
ISTAYMEVNGLKSDDTAVYYCARGGLEPRSVDYYYYGMDVWGQGTTVTVSS

CH66VH   [SEQ ID NO: 11]
QVQLVQSGAEVKKPGASVKVSCKASGYTFTDYHINWVRQAPGQGLEWMGWIHPNSGDTNYAQKFQGWVTMTRDTS
ISTAYMEVNGLKSDDTAVYYCARGGLEPRSVDYYYYGMDVWGQGTTVTVSS

CH67VH   [SEQ ID NO: 12]
QVQLVQSGAEVRKPGASVKVSCKASGYTFTDNYIHWVRQAPGQGLEWMGWIHPNSGATKYAQKFEGWVTMTRDTS
ISTVYMELSRSRSDDTAVYYCARAGLEPRSVDYYFYGLDVWGQGTAVTVSS

Figure 9

Light chain amino acid sequences:

CL860UCA_VL  [SEQ ID NO: 13]
QSVLTQPPSVSVAPGQTARITCGGNNIGSKSVHWYQQKPGQAPVLVVYDDSDRPSGIPERFSGSNSGNTATLTIS
RVEAGDEADYYCQVWDSSSDHVVFGGGTKLTVL

CH65_VL  [SEQ ID NO: 14]
QSVLTQPPSVSVAPGQTARITCGGNDIGRKSVHWNQQKPGQAPVLVVCYDSDRPSGIPERFSGSNSGNTATLTIS
RVEAGDEADYYCQVWDSSSDHVIFGGGTKLTVL

CH66VL  [SEQ ID NO: 15]
QSALTQPPSVSVAPGQTARITCGGNDIGRKSVHWNQQKPGQAPVLVVCYDSDRPSGIPERFSGSNSGNTATLTIS
RVEAGDEADYYCQVWDSSSDHVVFGGGTKLTVL

CH67VL  [SEQ ID NO: 16]
QSALTQPPSVSVAPGQTATITCGGNNIGRKRVDWFQQKPGQAPVLVVYEDSDRPSGIPERFSDSNSGTTATLTIS
RVEAGDEADYYCQVWDSDSDHVVFGGGTKLTVL

Figure 10

Alignment of VH DNA sequences of CL860UCA, CH65, CH66 and CH67:

```
CL860UCA_VH   CAGGTGCAGC TGGTGCAGTC TGGGGCTGAG GTGAAGAAGC CTGGGGCCTC AGTGAAGGTC
CH65_VH       G-A------- ---------- ---A------ ---------- ---------- ------A---
CH66_VH       ---------- ---------- ---------- ---------- ---------- ------A---
CH67_VH       ---------- ---------- ---------- ----G----- ---------- ----------  60

CL860UCA_VH   TCCTGCAAGG CTTCTGGATA CACCTTCACC GGCTACTATA TGCACTGGGT GCGACAGGCC
CH65_VH       ---------- ---------- ---------- -A---TC--- -AA------- ----------
CH66_VH       ---------- ---------- ---------- -A---TC--- -AA------- ----------
CH67_VH       ---------- ---------- ---------- -A-A------ -A-------- ----------  120

CL860UCA_VH   CCTGGACAAG GGCTTGAGTG GATGGGATGG ATCAACCCTA ACAGTGGTGG CACAAACTAT
CH65_VH       ---------- ---------- ---------- ---C------ ---------A ----------
CH66_VH       ---------- ---------- ---------- ---C------ ---------A ----------
CH67_VH       ---------- ---------- ---------- ---C------ ---------C ------G---  180

CL860UCA_VH   GCACAGAAGT TCAGGGCTG GGTCACCATG ACCAGGGACA CGTCCATCAG CACAGCCTAC
CH65_VH       ---------- ---------- ---------- ---------- --G------- ----------
CH66_VH       ---------- ---------- ---------- ---------- ---------- ----------
CH67_VH       ---------- --G------- ---------- ---------- ----A----- -----T----  240

CL860UCA_VH   ATGGAGCTGA GCAGGCTGAG ATCTGACGAC ACGGCCGTGT ATTACTGTGC GAGAGGGGGA
CH65_VH       ------G--- ATG-CT---A ---------- ---------- ----T----- ----------
CH66_VH       ------G--- ATG-CT---A ---------- ---------- ----T----- ----------
CH67_VH       -----A---- ----ATC--- ---------- --------A- ---------- -----C----  300

CL860UCA_VH   CTGGAACCcC GATCTGTAGA CTACTACTAC TACGGTATGG ACGTCTGGGG CCAAGGGACC
CH65_VH       --------C- ---------- --------T --T------- ---------- ----------
CH66_VH       --------T- ---------- --------T --T------- ---------- ----------
CH67_VH       --------A- -----C---- --------T- -------T--- ---------- ----------  360

CL860UCA_VH   ACGGTCACCG TCTCCTCA
CH65_VH       ---------- --------
CH66_VH       ---------- --------
CH67_VH       G--------- --------   360
```

Figure 11

Alignment of VL DNA sequences of CL860UCA, CH65, CH66 and CH67:

```
CL860UCA_VL    CAGTCTGTGC TGACTCAGCC ACCCTCGGTG TCAGTGGCCC CAGGACAGAC GGCCAGGATT
CH65_VL        ---------- ---------- ---------- ---------- ----G----- ----------
CH66_VL        --------CC- ---------- ---------- ---------- ----G----- ----------
CH67_VL        --------CC- ---------- ---------- ---------- ---------- ------C----    60

CL860UCA_VL    ACCTGTGGGG GAAACAACAT TGGAAGTAAA AGTGTGCACT GGTACCAGCA GAAGCCAGGC
CH65_VL        ---------- ----TG-T-- ------G--G ---------- --A------- ----------
CH66_VL        ---------- ----TG-T-- ------G--G ---------- --A------- ----------
CH67_VL        ---------- ---------- ----C----- --A---G--- ---T------ ----------   120

CL860UCA_VL    CAGGCCCCTG TGCTGGTCGT CTATGATGAT AGCGACCGGC CCTCAGGGAT CCCTGAGCGA
CH65_VL        ---------- ---------- --G-T----- ---------- ---------- ----------
CH66_VL        ---------- ---------- --G-T----- --T------- ---------- ----------
CH67_VL        ---------- ---------- -------G--- ---------- ---------- ----------   180

CL860UCA_VL    TTCTCTGGCT CCAACTCTGG GAACACGGCC ACCCTGACCA TCAGCAGGGT CGAAGCCGGG
CH65_VL        ---------- ----T--A-- ---------- ---------- ----T----- ----------
CH66_VL        ---------- ----T--A-- ---------- ---------- ---------- ----------
CH67_VL        --------A-- ---------- --C------- ---------- ---------- ----------   240

CL860UCA_VL    GATGAGGCCG ACTATTACTG TCAGGTGTGG GATAGTAGTA GTGATCATGT GGTATTCGGC
CH65_VL        ---------- -------T-- ---------- ---------- ---------- -A--------
CH66_VL        ---------- -------T-- ---------- ---------- ---------- ----------
CH67_VL        ---------- ---------- ---------- -------GA-- ---------- ----------   300

CL860UCA_VL    GGAGGGACCA AGCTGACCGT CCTA
CH65_VL        ---------- ---------- ----
CH66_VL        ---------- ---------- ----
CH67_VL        ---------- -A-------- ----    300
```

Figure 12

Alignment of VH amino acid sequences of CL860UCA, CH65, CH66 and CH67:

```
CL860UCA_VH    QVQLVQSGAE VKKPGASVKV SCKASGYTFT GYYMHWVRQA PGQGLEWMGW INPNSGGTNY
CH65_VH        E--------- ---------- ---------- D-HIN----- ---------- -H----D---
CH66VH         ---------- ---------- ---------- D-HIN----- ---------- -H----D---
CH67VH         ---------- -R-------- ---------- DN-I------ ---------- -H----A-K-

CL860UCA_VH    AQKFQGWVTM TRDTSISTAY MELSRLRSDD TAVYYCARGG LEPRSVDYYY YGMDVWGQGT
CH65_VH        ---------- ----A----- --VNG-K--- ---------- ---------- ----------
CH66VH         ---------- ---------- --VNG-K--- ---------- ---------- ----------
CH67VH         ----E----- --------V- -----S---- --------A- ---------F --L-------

CL860UCA_VH    TVTVSS
CH65_VH        ------
CH66VH         ------
CH67VH         A-----    120
```

Figure 13

Alignment of VL amino acid sequences of CL860UCA, CH65, CH66 and CH67:

```
CL860UCA_VL    QSVLTQPPSV SVAPGQTARI TCGGNNIGSK SVHWYQQKPG QAPVLVVYDD SDRPSGIPER
CH65_VL        ---------- ---------- -----D--R- ----N----- --------CY- ----------
CH66VL         --A------- ---------- -----D--R- ----N----- --------CY- ----------
CH67VL         --A------- --------T- --------R- R-D-F----- --------E-  ----------   60

CL860UCA_VL    FSGSNSGNTA TLTISRVEAG DEADYYCQVW DSSSDHVVFG GGTKLTVL
CH65_VL        ---------- ---------- ---------- -------I-- --------
CH66VL         ---------- ---------- ---------- ---------- --------
CH67VL         --D-----T-- ---------- ---------- --D------- --------   110
```

Figure 14A

Representative HA receptor binding domains from H1 influenza strains

>A/SOLOMON_ISLANDS/3/2006 [SEQ ID NO: 17]
APLQLGNCSVAGWILGNPECELLISRESWSYIVEKPNPENGTCYPGHFADYEELREQLSSV
SSFERFEIFPKESSWPNHTTTGVSASCSHNGESSFYKNLLWLTGKNGLYPNLSKSYANNKE
KEVLVLWGVHHPPNIGDQRALYHTENAYVSVVSS
HYSRKFTPEIAKRPKVRDREGRINYYWTLL EPGDTIIFEANGNLIAPRYA FALSRGFGSG

>A/JOHANNESBURG/82/96 [SEQ ID NO: 18]
APLQLGNCSVAGWILGNPECESLFSKESWSYIAETPNPENGTCYPGHFADYEELREQLSSV
SSFERFEIFPKESSWPNHTVTKGVTASCSHNGKSSFYKNLLWLTEKNGLYPNLSKSYVNNK
EKEVLVLWGVHHPSNIGDQRAIYHTENAYVSVVSSHYSRRFTPEIAKRPKVRGQEGRINYY
WTLLEPGDTIIFEANGNLIAPWYAFALSRGFGSG

>A/SHENZEN/227/95 [SEQ ID NO: 19]
APLQLGNCSVAGWILGNPECESLFSKESWSYIAETPNPENGTCYPGYFADYEELREQLSSV
SSFERFEIFPKESSWPKHTVTKGVTASCSHNGKSSFYKNLLWLTEKNGLYPNLSKSYVNNK
EKEVLVLWGVHHPSNIGDQRAIYHTENAYVSVVSSHYSRRFTPEIAKRPKVRGQEGRINYY
WTLLEPGDTIIFEANGNLIAPWYAFALSRGFGSG

>A/FLORIDA/2/1993 [SEQ ID NO: 20]
APLQLGNCSVAGWILGNPECESLFTKESWSYIAETPNPENGTCYPGYFADYEELREQLSSV
SSFERFEIFPKESSWPNHTVTKGVTASCSHNGKSSFYRNLLWLTEKNGLYPNLSKSYVNNK
EKEVLVLWGVHHPSNMGDQRAIYHTENAYVSVVSSHYSRRFTPEIAKRPKVRDQEGRINYY
WTLLEPGDTIIFEANGNLIAPRYAFALSRGFGSG

>A/MOSCOW/13/1998 [SEQ ID NO: 21]
APLQLGNCSIAGWILGNPECESLFSKESWSYIAETPNPENGTCYPGYFADYEELREQLSSV
SSFERFEIFPKESSWPNHTVTKGVTASCSHNGKSSFYKNLLWLTEKNGLYPNLSKSYVNNK
KKEVLVLWGVHHPSNIGDQRAIYHTENAYVSVVSSHYSRRFTPEIAKRPKVRNQEGRINYY
WTLLEPGDTIIFEANGNLIAPWYAFALSRGFESG

>A/JOHANNESBURG/159/97 [SEQ ID NO: 22]
APLQLG NCSVAGWILG NPECESLIFK ESWSYIVETP NPENGTCYPG YFADYEELRE
QLSSVSSFER FEIFPKESSW PNHTVTGVSA SCSHNGKSSF YRNLLWLTEK
NGLYPNLSKS YVNNKEKEVL VLWGVHHPSN IRDQRAIYHT ENAYVSVVSS
HYSRRFTPEI AKRPKVRGQE GRINYYWTLL EPGDTIIFEA NGNLIAPWYA FALSRGFGSG

>A/BRISBANE/59/2007 [SEQ ID NO: 23]
APLQLG NCSVAGWILG NPECELLISK ESWSYIVEKP NPENGTCYPG
HFADYEELREQLSSVSSFER FEIFPKESSW PNHTVTGVSA SCSHNGESSF
YRNLLWLTGK NGLYPNLSKSYANNKEKEVL VLWGVHHPPN IGDQKALYHT
ENAYVSVVSS HYSRKFTPEI AKRPKVRDQEGRINYYWTLL EPGDTIIFEA NGNLIAPRYA
FALSRGFGSG

>A/BEIJING/262/1995 [SEQ ID NO: 24]
APLQLG NCSVAGWILG NPECESLISK ESWSYIVETP NPENGTCYPG
YFADYEELREQLSSVSSFER FEIFPKESSW PNHTVTGVTA SCSHNGKSSF
YRNLLWLTEK NGLYPNLSNSYVNNKEKEVL VLWGVHHPSN IGVQRAIYHT
ENAYVSVVSS HYSRRFTPEI AKRPKVRGQE GRINYYWTLL EPGDTIIFEA NGNLIAPWYA
FALSRGFGSG

Figure 14A (CONTINUED)

>A/AUCKLAND/65/2001 [SEQ ID NO: 25]
APLQLGNCSVAGWILGNP ECELLISKES WSYIVETPNP ENGTCYPGYF ADYEELREQL
SSVSSFERFEIFPKGSSWPN HTVTGVSASC SHNGKSSFYR NLLWLTGKNG
LYPNLSMSYV NNKEKEVLVLWGVHHPPNIG DQRALYHTEN AYVSVVSSHY
SRRFTPEIAK RPKVRDQEGR INYYWTLLEPGDTIIFEANG NLIAPWYAFA LSRGFGSG

>A/VICTORIA/36/1988 [SEQ ID NO: 26]
APLQLGNCSIAGWILGNPECESLFSKKSWSYIAETPNSENGTCYPGYFADYEELREQLSSV
SSFERFEIFPKESSWPNHTVTKGVTASCSHKGRSSFYRNLLWLTEKNGLYPNLSKSYVNNK
EKEVLVLWGVHHPSNIGDQRAIYHTENAYVSVVSSHYNRRFTPEIAKRPKVRGQEGRINYY
WTLLEPGDTIIFEANGNLIAPWYAFALSRGFGSG

>A/BANGKOK/163/2000 [SEQ ID NO: 27]
APLQLGNCSVAGWILGNPECELLISKESWSYIVETPNPENGTCYPGYFADYEELREQLSSV
SSFERFEIFPKESSWPNHTVTGVSASCSHNGKSSFYRNLLWLTGKNGLYPNLSMSYVNNK
EKEVLVLWGVHHPPNIGNQRALYHTENAYVSVVSSHYSRRFTPEIAKRPKVRDQEGRINYY
WTLLEPGDTIIFEANGNLIAPWYAFALSRGFGSG

>A/CHILE/8885/2001 [SEQ ID NO: 28]
APLQLGNCSVAGWILGNPECELLISKGSWSYIVETPNPENGTCYPGYFADYEELREQLSSV
SSFERFEIFPKGSSWPNHTVTGVSASCSHNGKSSFYRNLLWLTGKNGLYPNLSMSYVNNK
EKEVLVLWGVHHPPNIGNQRALYHTENAYVSVVSSHYSRRFTPEIAKRPKVRDQEGRINYY
WTLLEPGDTIIFEANGNLIAPWYAFALSRGFGSG

>A/NEIMENGGU/52/2002 [SEQ ID NO: 29]
APLQLGNCSVAGWILGNPECELLISKESWSYIVETPNPENGTCYPGYFADYEELREQLSSV
SSFERFEIFPKESSWPNHTVTGVSASCSHNGKSSFYRNLLWLTGKNGLYPNLSKSYANNKK
KEVLVLWGVHHPPNIGNQRALYHTENAYVSVVSSHYSRRFTPEIAKRPKVRDQEGRINYYW
TLLEPGDTIIFEANGNLIAPRYAFALSRGFGSG

>A/BRAZIL/1403/2003/A [SEQ ID NO: 30]
APLQLGNCSVAGWILGNPECELLISKESWSYIVETPNPENGACYPGYFADYEELREQLSSV
SSFERFEIFPKKSSWPNHTVTGVSASCSHNGKSSFYRNLLWLTGKNGLYPNLSKSYANNKK
KEVLILWGVHHPPNIGDQRTLYHTENAYVSVVSSHYSRRFTPEITKRPKVRDQEGRINYYW
TLLEPGDTIIFEANGNLIAPWYAFALSRGFGSG

>A/BRAZIL/1403/2003/B [SEQ ID NO: 31]
APLQLGNCSVAGWILGNPECELLISKESWSYIVETPNPENGACYPGYFADYEELREQLSSV
SSFERFEIFPKKSSWPNHTVTGVSASCSHNGKSSFYRNLLWLTGKNGLYPNLSKSYANNKK
KEVLILWGVHHPPNIGDQRTLYHTENAYVSVVSSHYSRRFTPEITKRPKVRDQEGRINYYW
TLLEPGDTIIFEANGNLIAPWYAFALSRGFGSG

>A/FUJIAN/156/2000 [SEQ ID NO: 32]
APLQLGNCSVAGWILGNPECELLISKESWSYIVETPNPENGTCYPGYFADYEELREQLSSV
SSFERFEIFPKESSWPNHTVTGVSASCSHNGKSSFYRNLLWLTGKNGLYPNLSKSYANNKE
KEVLVLWGVHHPPNIGNQRALYHTENAYVSVVSSHYSRRFTPEIAKRPKVRDQEGRINYYW
TLLEPGDTIIFEANGNLIAPRYAFALSRGFGSG

Figure 14A (CONTINUED)

>A/OSTRAVA/801/98 [SEQ ID NO: 33]
APLQLGNCSVAGWILGNPECESLISKESWSYIVETPNPENGTCYPGYFADYEELREQLSSV
SSFERFEIFPKESSWP<u>NHTVTGVSAS</u>CSHNGKSSFYRNLLWL<u>TKKNGLYPNLSKS</u>YVNNKE
KEVLVLWGVHHPS<u>NIGDQRTIYH</u>TENAYVSVVSSHYSRRFTPEIAK<u>RPKVRDQE</u>GRINYYW
TLLEPGDTIIFEANGNLIAPWYAFALSRGFGSG

>A/CALIFORNIA/07/2009 [SEQ ID NO: 34]
APLHLGKCNIAGWILGNPECESLSTASSWSYIVETPSSDNGTCYPGDFIDYEELREQLSSVS
SFERFEIFPKTSSWP<u>NHDSNKGVTAA</u>CPHAGAKSFYKNLIWL<u>VKKGNSYPKLSKS</u>YINDKG
KEVLVLWGIHHPS<u>TSADQQSLYQ</u>NADAYVFVGSSRYSKKFKPEIAI<u>RPKVRDQE</u>GRMNYY
WTLVEPGDKITFEATGNLVVPRYAFAMERNAGSG

Figure 14B

Representative HA receptor binding domains from H2 influenza strains

>A/Adachi/2/1957 [SEQ ID NO: 35]
NGKLCKLNGIPPLELGDCSIAGWLLGNPECDRLLSVPEWSYIMEKENPRNGLCYPGSFNDY
EELKHLLSSVKHFEKVKILPKDRWTQHTTTGGSQACAVSGNPSFFRNMVWLTKKGSDYPV
AKGSYNNTSGEQMLIIWGVHHPIDETEQRTLYQNVGTYVSVGTSTLNKRSTPEIATRPKVN
GLGSRMEFSWTLLDMWDTINFESTGNLIAPEYGFKIKRGSS >A/Albany/1/1960 [SEQ ID NO: 36]
NGKLCKLNGIPPLELGDCSIAGWLLGNPECDRLLRVPEWSYIMEKENPRDGLCYPGSFNDY
EELKHLLSSVKHFEKVRILPKDRWTQHTTTGGSRACAVSGNPSFFRNMIWLTKKGSNYPVA
KGSYNNTSGEQMLIIWGVHHPIDETEQRTLYQNVETYVSVVTSTLNKRSTPKIATRPKVNGL
GGRMEFSWTLLDMWDTINFESTGNLIAPEYGFKISKRGSS >A/Chile/13/57 [SEQ ID NO: 37]
NGKLCKLNGIPPLELGDCSIAGWLLGNPECDRLLSVPEWSYIMEKENPRDGLCYPGSFNDY
EELKHLLSSVKHFEKVKILPKDRWTQHTTTGGSRACAVSGNPSFFRNMVWLTEKGSNYPV
AKGSYNNTSGEQMLIIWGVHHPNDETEQRTLYQNVGTYVSVGTSTLNKRSTPEIATRPKVN
GLGGRMEFSWTLLDMWDTINFESTGNLIAPEYGFKISKRGSS >A/Kumamoto/1/65 [SEQ ID NO: 38]
NGKLCKLNGIPPLELGDCSIAGWLLGNPECDRLLRVPEWSYIMEKENPRYSLCYPGSFNDY
EELKHLLSSVKHFEKVRILPKDRWTQHTTTGDSKACAVSGKPSFFRNMVWLTKKGPNYPV
AKGSYNNTSGEQMLIIWGVHHPKDEAEQRALYQNVGTYVSASTSTLNKRSIPEIATRPEVN
GLGSRMEFSWTLLDAWDTINFESTGNLVAPEYGFKISKRGSS

Figure 14C

Representative HA receptor binding domains from H3 influenza strains

>A/Wisconsin/67/2005 [SEQ ID NO: 39]
HQILDGENCTLIDALLGDPQCDGFQNKKWDLFVERSKAYSNCYPYDVPDYASLRSLVASSG
TLEFNDESFNWTGVTQNGTSSSCKRRSNNSFFSRLNWLTHLKFKYPALNVTMPNNEKFDK
LYIWGVHHPVTDNDQIFLYAQASGRITVSTKRSQQTVIPNIGSRPRIRNIPSRISIYWTIVKPG
DILLINSTGNLIAPRGYFKIRSGKSS >A/Wisconsin/15/2009 [SEQ ID NO: 40]
HQILDGKNCTLIDALLGDPQCDGFQNKKWDLFVERSKAYSNCYPYDVPDYASLRSLVASSG
TLEFNNESFNWTGVTQNGTSSACIRRSKNSFFSRLNWLTHLNFKYPALNVTMPNNEQFDKL
YIWGVHHPGTDKDQIFPYAQASGRITVSTKRSQQTAIPNIGSRPRVRNIPSRISIYWTIVKPG
DILLINSTGNLIAPRGYFKIRSGKSS >A/X31 [SEQ ID NO: 41]
HRILDGIDCTLIDALLGDPHCDVFQNETWDLFVERSKAFSNCYPYDVPDYASLRSLVASSGT
LEFITEGFTWTGVTQNGGSNACKRGPGSGFFSRLNWLTKSGSTYPVLNVTMPNNDNFDKL
YIWGIHHPSTDQEQTSLYVQASGRVTVSTRRSQQTIIPNIGSRPWVRGLSSRISIYWTIVKPG
DVLVINSNGNLIAPRGYFKMRTGKSS >A/Brisbane/10/2007 [SEQ ID NO: 42]
HQILDGENCTLIDALLGDPQCDGFQNKKWDLFVERSKAYSNCYPYDVPDYASLRSLVASSG
TLEFNNESFNWTGVTQNGTSSACIRRSNNSFFSRLNWLTHLKFKYPALNVTMPNNEKFDKL
YIWGVHHPGTDNDQIFPYAQASGRITVSTKRSQQTVIPNIGSRPRVRNIPSRISIYWTIVKPG
DILLINSTGNLIAPRGYFKIRSGKSS >A/Moscow/10/99 [SEQ ID NO: 43]
HQILDGENCTLIDALLGDPHCDGFQNKEWDLFVERSKAYSNCYPYDVPDYASLRSLVASSG
TLEFNNESFNWTGVAQNGTSSSCKRRSIKSFFSRLNWLHQLKYRYPALNVTMPNNDKFDK
LYIWGVHHPSTDSDQTSLYTQASGRVTVSTKRSQQTVIPNIGSRPWVRGISSRISIYWTIVKP
GDILLINSTGNLIAPRGYFKIRSGKSS

Figure 14D

HA receptor binding domain from ferret-adapted H5 influenza A

>A/Indonesia/5/2005_ferret_adapted [SEQ ID NO: 44]*
 VKPLILRD CSVAGWLLGN PMCDEFINVP EWSYIVEKAN PTNDLCYPGS FNDYEELKHL
LSRINHFEKI QIIPKSSWS<u>D HEASSGVSSA</u> CPYLGSPSFF RNVVWL<u>IKKN STYPTIKKS</u>Y
NNTNQEDLLV LWGIHHP<u>KDA AEQTRLY</u>QNP TTYISIGTST LNQRLVPKIA T<u>RSKVNGLSS</u>
RMEFFWTILK PNDAINFESN GNFIAPEYAY KIVKKGD >A/Indonesia/5/2005 [SEQ ID NO: 45]*
 VKPLILRD CSVAGWLLGN PMCDEFINVP EWSYIVEKAN PTNDLCYPGS FNDYEELKHL
LSRINHFEKI QIIPKSSWS<u>D HEASSGVSSA</u> CPYLGSPSFF RNVVWL<u>IKKN STYPTIKKS</u>Y
NNTNQEDLLV LWGIHHP<u>NDA AEQTRLY</u>QNP TTYISIGTST LNQRLVPKIA T<u>RSKVNGQSG</u>
RMEFFWTILK PNDAINFESN GNFIAPEYAY KIVKKGDS

*Mutations responsible for adaptation are noted in bold.

Figure 15

```
A/INDONESIA/5/2005_FERRET_H5N1              KPLILRDCSVAGWLLGNPMCDEFINVPEWSYIVEKANPTN
A/ADACHI/2/1957_H2N2_                       PPLELGDCSIAGWLLGNPECDRLLSVPEWSYIMEKENPRN
A/CALIFORNIA/07/2009_H1N1                   APLHLGKCNIAGWILGNPECESLSTASSWSYIVETPSSDN
A/SOLOMON_ISLANDS/3/2006_H1N1               APLQLGNCSVAGWILGNPECELLISRESWSYIVEKPNPEN
A/X31_H3N2                                  RILDGIDCTLIDALLGDPHCDVFQN-ETWDLFVERSKAFS

A/INDONESIA/5/2005_FERRET_H5N1    DLCYPGSFNDYEELKHLLSRINHFEKIQIIPK-SSWSDHEASSGVSSACP
A/ADACHI/2/1957_H2N2              GLCYPGSFNDYEELKHLLSSVKHFEKVKILPK-DRWTQHTTTGG-SQACA
A/CALIFORNIA/07/2009_H1N1         GTCYPGDFIDYEELREQLSSVSSFERFEIFPKTSSWPNHDSNKGVTAACP
A/SOLOMON_ISLANDS/3/2006_H1N1     GTCYPGHFADYEELREQLSSVSSFERFEIFPKESSWPNHTTT-GVSASCS
A/X31_H3N2                        -NCYPYDVPDYASLRSLVASSG---TLEFITEGFTWTGVTQNGG-SNACK

A/INDONESIA/5/2005_FERRET_H5N1    YLGSPSFFRNVVWLIKKNSTYPTIKKSYNNTNQEDLLVLWGIHHPKDAAE
A/ADACHI/2/1957_H2N2              VSGNPSFFRNMVWLTKKGSDYPVAKGSYNNTSGEQMLIIWGVHHPIDETE
A/CALIFORNIA/07/2009_H1N1         HAGAKSFYKNLIWLVKKGNSYPKLSKSYINDKGKEVLVLWGIHHPSTSAD
A/SOLOMON_ISLANDS/3/2006_H1N1     HNGESSFYKNLLWLTGKNGLYPNLSKSYANNKEKEVLVLWGVHHPPNIGD
A/X31_H3N2                        RGPGSGFFSRLNWLTKSGSTYPVLNVTMPNNDNFDKLYIWGIHHPSTDQE

A/INDONESIA/5/2005_FERRET_H5N1    QTRLYQNPTTYISIGTSTLNQRLVPKIATRSKVNGLSSRMEFFWTILKPN
A/ADACHI/2/1957_H2N2              QRTLYQNVGTYVSVGTSTLNKRSTPEIATRPKVNGLGSRMEFSWTLLDMW
A/CALIFORNIA/07/2009_H1N1         QQSLYQNADAYVFVGSSRYSKKFKPEIAIRPKVRDQEGRMNYYWTLVEPG
A/SOLOMON_ISLANDS/3/2006_H1N1     QRALYHTENAYVSVVSSHYSRKFTPEIAKRPKVRDREGRINYYWTLLEPG
A/X31_H3N2                        QTSLYVQASGRVTVSTRRSQQTIIPNIGSRPWVRGLSSRISIYWTIVKPG

A/INDONESIA/5/2005_FERRET_H5N1    DAINFESNGNFIAPEYAYKIVKKGD
A/ADACHI/2/1957_H2N2              DTINFESTGNLIAPEYGFKIKRGSS
A/CALIFORNIA/07/2009_H1N1         DKITFEATGNLVVPRYAFAMERNAG
A/SOLOMON_ISLANDS/3/2006_H1N1     DTIIFEANGNLIAPRYAFALSRGFG
A/X31_H3N2                        DVLVINSNGNLIAPRGYFKMRTGKS
```

US 9,718,873 B2

BROADLY NEUTRALIZING HUMAN ANTIBODY THAT RECOGNIZES THE RECEPTOR-BINDING POCKET OF INFLUENZA HEMAGGLUTININ

CROSS-REFERENCE TO RELATED APPLICATIONS

This application is a Continuation-in-Part filing of PCT/US2012/49573, filed on Aug. 3, 2012, which claims the benefit of U.S. Provisional Patent Application No. 61/514,662, filed Aug. 3, 2011, the contents of all of which are incorporated herein by reference in their entirety.

STATEMENT OF RIGHTS TO INVENTIONS MADE UNDER FEDERALLY SPONSORED RESEARCH

This work was supported by grant nos. U19 AI067854 and P01GM62580 from the National Institutes of Health. The Government has certain rights in this invention.

BACKGROUND OF THE INVENTION

The well-known seasonal drift of influenza virus antigenicity accounts for the absence of long-term immune protection in previously infected individuals. The hemagglutinin (HA), a trimeric surface glycoprotein that binds the viral receptor and promotes fusion and penetration from low-pH endosomes, is the principal surface antigen on influenza virions. HA presents conserved as well as variable epitopes, but neutralizing antibodies against the latter dominate the response to immunization and infection.

Accordingly, there is a need for developing broadly neutralizing therapeutics that can effectively treat or prevent drifted strains of influenza.

SUMMARY OF THE INVENTION

As described below, the present invention is based upon the discovery of novel antibodies that broadly neutralize influenza antigenic variants. The invention features compositions and kits containing the novel antibodies, as well as methods for using these novel therapeutic molecules to treat or prevent influenza viral infection.

In aspects, the invention provides isolated anti-influenza antibody or antibody fragment that specifically binds to an epitope of an influenza hemagglutinin (HA). Binding of the antibody or antibody fragment to the influenza HA epitope reduces or inhibits influenza HA binding to sialic acid.

The present invention also provides in other aspects an isolated anti-influenza antibody or antibody fragment that specifically binds to a sialic acid binding domain of a surface antigen of influenza virus. In one embodiment, the surface antigen of influenza virus is HA.

In embodiments, the epitope of influenza HA comprises a sialic-acid binding domain.

In embodiments, the HA is H1 HA, H2 HA, H3 HA, or H5 HA (an HA from a human adapted H5 strain).

In related embodiments, the antibody contacts one or more residues in influenza HA epitope comprising residue 158; residues 158-160; 135-136, 190-195, and 226; 222, 225, and 227; and residues 187 and 189 where the numbering refers to the one used in structures such as that for A/Solomon Islands/3/2006 (Protein Data Bank accession number 3SM5).

In related embodiments, the influenza HA epitope comprises the amino acids set forth in any one of SEQ ID NOs:17-44.

In related embodiments, the influenza HA epitope comprises the CH65-CH67 binding residues in any one of SEQ ID NOs:17-44 (e.g., the CH65-CH67 binding residues identified in FIG. 15).

In other embodiments, the anti-influenza antibody or antibody fragment contacts one or more residues in the sialic acid binding pocket of the HA epitope selected from the group consisting of residues: 134-136, 190-195 and 226. In another embodiment, the antibody or antibody fragment further contacts one or more residues in the HA epitope selected from the group consisting of residues: 158, 158-160, 135-136, 190-195 and 226, and 187 and 189, where the numbering refers to the one used in structures such as that for A/Solomon Islands/3/2006 (Protein Data Bank accession number 3SM5).

In another embodiment, the antibody CDR H1 region contacts residue 158 of the HA epitope; the CDR H2 region contacts residues 158-160 of the HA epitope; the CDR H3 region contacts residues 135-136, 190-194 and 226 of the HA epitope; the CDR L1 region contacts residues 222, 225 and 227 of the HA epitope; or the CDR L3 region contacts residues 187 and 198 of the HA epitope.

In embodiments, the anti-influenza antibody or antibody fragment comprises a variable heavy ($V_H$) chain, and wherein the $V_H$ chain comprises an amino acid sequence set forth in SEQ ID NO: 9, SEQ ID NO: 10, SEQ ID NO: 11, or SEQ ID NO: 12.

In embodiments, the anti-influenza antibody or antibody fragment comprises one or more heavy chain CDR regions present in a variable heavy ($V_H$) chain amino acid sequence of SEQ ID NO: 9, SEQ ID NO: 10, SEQ ID NO: 11, or SEQ ID NO: 12. In related embodiments, the one or more heavy chain CDR regions comprises a CDR3 region present in the variable heavy ($V_H$) chain amino acid sequence of SEQ ID NO: 9, SEQ ID NO: 10, SEQ ID NO: 11, or SEQ ID NO: 12.

In embodiments, the anti-influenza antibody or antibody fragment comprises a variable light ($V_L$) chain, and wherein the $V_L$ chain comprises an amino acid sequence set forth in SEQ ID NO: 13, SEQ ID NO: 14, SEQ ID NO: 15, or SEQ ID NO: 16.

In embodiments, the anti-influenza antibody or antibody fragment comprises one or more light chain CDR regions present in a variable light ($V_L$) chain amino acid sequence of SEQ ID NO: 13, SEQ ID NO: 14, SEQ ID NO: 15, or SEQ ID NO: 16. In related embodiments, the one or more light chain CDR regions comprises a CDR3 region present in the variable heavy ($V_L$) chain amino acid sequence of SEQ ID NO: 13, SEQ ID NO: 14, SEQ ID NO: 15, or SEQ ID NO: 16.

In embodiments, the anti-influenza antibody or antibody fragment comprises i) a variable heavy ($V_H$) chain amino comprising an amino acid sequence set forth in SEQ ID NO: 10, and ii) a variable light ($V_L$) chain comprising an amino acid sequence set forth in SEQ ID NO: 14.

In embodiments, the anti-influenza antibody or antibody fragment comprises a variable heavy ($V_H$) chain, wherein the CDR3 region of the $V_H$ chain comprises Arg104, Ser105, Val106, Asp107, Tyr109, Tyr110, Tyr112, or a combination thereof.

In embodiments, the anti-influenza antibody is a monoclonal antibody or antibody fragment thereof.

In embodiments, the anti-influenza antibody is a humanized antibody.

In embodiments, the antibody fragment is an Fab fragment, an Fab' fragment, an Fd fragment, a Fd' fragment, an Fv fragment, a dAb fragment, an F(ab')$_2$ fragment, a single chain fragment, a diabody, or a linear antibody.

In embodiments, the anti-influenza antibody or antibody fragment further comprises an agent conjugated to the anti-influenza antibody or antibody fragment thereof. In related embodiments, the agent conjugated to the antibody or antibody fragment thereof is a therapeutic agent or detectable label.

The therapeutic agent can be any therapeutic agent suitable for use with the novel antibodies. Such agents are well known in the art and include small molecules, nanoparticles, polypeptides, radioisotopes, inhibitory nucleic acids, and the like. In embodiments, the therapeutic agent is an antiviral agent or a toxin. In embodiments, the therapeutic agent is an siRNA, shRNA, or antisense nucleic acid molecule that reduces influenza virus production.

The detectable label can be any detectable label suitable for use with the novel antibodies. Such labels are well known in the art and include labels that are detected by spectroscopic, photochemical, biochemical, immunochemical, physical, or chemical means. In embodiments, the detectable label is an enzyme, a fluorescent molecule, a particle label, an electron-dense reagent, a radiolabel, a microbubble, biotin, digoxigenin, or a hapten or a protein that has been made detectable.

In aspects, the invention provides pharmaceutical compositions containing at least one of the anti-influenza antibody or antibody fragments described herein. In embodiments, the pharmaceutical compositions contain a pharmaceutically acceptable carrier, diluent, or excipient.

In aspects, the invention provides isolated polynucleotides encoding an anti-influenza antibody or antibody fragments described herein. In related aspects, the invention provides expression vectors comprising such an isolated polynucleotide. In further related aspects, the invention provides host cells comprising such an expression vector.

In aspects, the invention provides methods for treating or preventing an influenza virus infection in a subject in need thereof. The methods involve administering to the subject an effective amount of an anti-influenza antibody or antibody fragment described herein, or a pharmaceutical composition containing the antibody or antibody fragment. The methods treat or prevent influenza virus infection in the subject, including reducing or alleviating symptoms associated with infection.

In aspects, the invention provides methods for neutralizing an influenza virus in a subject in need thereof. The methods involve administering to the subject an effective amount of an anti-influenza antibody or antibody fragment described herein, or a pharmaceutical composition containing the antibody or antibody fragment. The methods neutralize the influenza virus in the subject, thereby treating or prevent influenza virus infection in the subject, including reducing or alleviating symptoms associated with infection.

In aspects, the invention provides methods for establishment of influenza virus infection in a subject in need thereof. The methods involve administering to the subject an effective amount of an anti-influenza antibody or antibody fragment described herein, or a pharmaceutical composition containing the antibody or antibody fragment. The methods inhibit establishment of influenza virus infection in the subject, thereby preventing symptoms associated with infection.

In aspects, the invention provides methods for inhibiting dissemination of influenza virus infection in a subject in need thereof. The methods involve administering to the subject an effective amount of an anti-influenza antibody or antibody fragment described herein, or a pharmaceutical composition containing the antibody or antibody fragment. The methods inhibit dissemination of influenza virus infection in the subject, thereby reducing or alleviating symptoms associated with infection.

In aspects, the invention provides methods for inhibiting influenza virus entry into a cell in a subject. The methods involve administering to the subject an effective amount of an anti-influenza antibody or antibody fragment described herein, or a pharmaceutical composition containing the antibody or antibody fragment. The methods inhibit influenza virus entry into a cell in the subject, thereby preventing symptoms associated with infection or reducing or alleviating symptoms associated with infection.

In aspects, the invention provides methods for inhibiting influenza virus entry into a cell. The methods involve contacting a cell having or at risk of developing influenza virus infection with an anti-influenza antibody or antibody fragment described herein, or a pharmaceutical composition containing the antibody or antibody fragment. The methods inhibit influenza virus entry into the cell.

In any of the above aspects, the subject has or is at risk of developing an influenza infection. In related embodiments, the subject is a mammal (e.g., human). In related embodiments, the subject is susceptible to viral infection (e.g., a pregnant female, a young subject or an infant subject, an elderly subject).

In any of the above aspects and embodiments, the anti-influenza antibody or antibody fragment, or the pharmaceutical composition is administered by intramuscular injection, intravenous injection, subcutaneous injection, or inhalation.

In aspects, the invention provides kits for treating or preventing influenza virus infection; kits for neutralizing influenza virus; kits for inhibiting establishment of influenza virus infection; kits for inhibiting dissemination of influenza virus infection; and kits for inhibiting influenza virus entry into a cell.

In embodiments, the kits contain an anti-influenza antibody or antibody fragment described herein.

In embodiments, the kits also contain a therapeutic agent. In related embodiments, the therapeutic agent inhibits influenza infection.

In embodiments, the kits also contain directions for using the kits in any of the methods described herein.

In any of the above embodiments, the influenza can be H1N1, H2N2, H3N2, or a human adapted H5 influenza strain (i.e., an H5 influenza that has acquired human-receptor specificity; see FIG. 14D for exemplary strains).

Additional objects and advantages of the invention will be set forth in part in the description which follows, and in part will be obvious from the description, or may be learned by practice of the invention. The objects and advantages of the invention will be realized and attained by means of the elements and combinations disclosed herein, including those pointed out in the appended claims. It is to be understood that both the foregoing general description and the following detailed description are exemplary and explanatory only and are not restrictive of the invention as claimed. The accompanying drawings, which are incorporated herein and constitute a part of this specification, illustrate several embodiments of the invention and, together with the description, serve to explain the principles of the invention.

DEFINITIONS

To facilitate an understanding of the present invention, a number of terms and phrases are defined below.

As used herein, the singular forms "a", "an", and "the" include plural forms unless the context clearly dictates otherwise. Thus, for example, reference to "an influenza antibody" includes reference to more than one influenza antibody.

Unless specifically stated or obvious from context, as used herein, the term "or" is understood to be inclusive.

As used herein, the terms "comprises," "comprising," "containing," "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, and the like.

The basic four-chain antibody unit is a heterotetrameric glycoprotein composed of two identical light (L) chains and two identical heavy (H) chains. An IgM antibody consists of 5 of the basic heterotetramer unit along with an additional polypeptide called J chain, and therefore contains 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for µ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71, and Chapter 6.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In embodiments, the antibody is purified: (1) to 80%, 85%, 90%, 95%, 99% or more by weight of antibody as determined by the Lowry method; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue, silver stain, and the like. Isolated antibody includes the antibody in situ within recombinant cells since at least one component of the antibody's natural environment will not be present. In embodiments, an isolated antibody will be prepared by at least one purification step.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

An "Fv antibody" refers to the minimal antibody fragment that contains a complete antigen-recognition and -binding site either as two-chains, in which one heavy and one light chain variable domain form a non-covalent dimer, or as a single-chain (scFv or sFv), in which one heavy and one light chain variable domain are covalently linked by a flexible peptide linker so that the two chains associate in a similar dimeric structure. In this configuration the complementary determining regions (CDRs) of each variable domain interact to define the antigen-binding specificity of the Fv dimer. Alternatively a single variable domain (or half of an Fv) can be used to recognize and bind antigen, although generally with lower affinity.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

A "monoclonal antibody" refers to homogenous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster, and the like) that have the desired specificity, affinity, and capability (Jones et al., 1986, *Nature*, 321:522-525; Riechmann et al., 1988, *Nature*, 332:323-327; Verhoeyen et al., 1988, *Science*, 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residue either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc) with the desired specificity, affinity, and capability while the constant regions are homologous to the sequences in antibodies derived from another (usually human) to avoid eliciting an immune response in that species.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (see Kabat et al., *Sequences of Proteins of Immunological Interest* (5th ed., 1991, National Institutes of Health, Bethesda Md.)); and (2) an approach based on crystallographic studies of antigen-antibody complexes (see Al-lazikani et al. *J. Molec. Biol.* 273:927-948 (1997)). In addition, combinations of these two approaches are sometimes used in the art to determine CDRs.

"Administering" is defined herein as a means of providing an agent or a composition containing the agent to a subject in a manner that results in the agent being inside the subject's body. Such an administration can be by any route including, without limitation, oral, transdermal (e.g., vagina, rectum, oral mucosa), by injection (e.g., subcutaneous, intravenous, parenterally, intraperitoneally, intrathecal), or by inhalation (e.g., oral or nasal). Pharmaceutical preparations are, of course, given by forms suitable for each administration route.

By "agent" is meant any small molecule chemical compound, antibody, nucleic acid molecule, or polypeptide, or fragments thereof.

By "analog" is meant a molecule that is not identical, but has analogous functional or structural features. For example, an amide, ester, carbamate, carbonate, ureide, or phosphate analog of an influenza antibody is a molecule that either: 1) does not destroy the biological activity of the influenza antibody and confers upon that influenza antibody advantageous properties in vivo, such as uptake, duration of action, or onset of action; or 2) is itself biologically inactive but is converted in vivo to a biologically active compound. Analogs include prodrug forms of an influenza antibody. Such a prodrug is any compound that when administered to a biological system generates the influenza antibody as a result of spontaneous chemical reaction(s), enzyme catalyzed chemical reaction(s), and/or metabolic chemical reaction(s).

By "control" is meant a standard or reference condition.

The term "derivative" means a pharmaceutically active compound with equivalent or near equivalent physiological functionality to a given agent (e.g., an influenza antibody). As used herein, the term "derivative" includes any pharmaceutically acceptable salt, ether, ester, prodrug, solvate, stereoisomer including enantiomer, diastereomer or stereoisomerically enriched or racemic mixture, and any other compound which upon administration to the recipient, is capable of providing (directly or indirectly) such a compound or an antivirally active metabolite or residue thereof.

By "disease" is meant any condition or disorder that damages or interferes with the normal function of a cell, tissue, or organ.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

Competition between antibodies is determined by an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242-253 (1983)); solid phase direct biotin-avidin EIA (see Kirkland et al., *J. Immunol.* 137:3614-3619 (1986)); solid phase direct labeled assay, solid phase direct labeled sandwich assay (see Harlow and Lane, "*Antibodies, A Laboratory Manual*," Cold Spring Harbor Press (1988)); solid phase direct label RIA using I-125 label (see Morel et al., *Molec. Immunol.* 25(1):7-15 (1988)); solid phase direct biotin-avidin EIA (Cheung et al., *Virology* 176:546-552 (1990)); and direct labeled RIA (Moldenhauer et al., *Scand. J. Immunol.* 32:77-82 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. When a competing antibody is present in excess, it will inhibit specific binding of a reference antibody to a common antigen by at least 25%, 50, 75%, or more.

By "enhances" or "increases" is meant a positive alteration of at least about 10%, 25%, 50%, 75%, or 100% relative to a reference.

By "fragment" is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen, or reversed Hoogsteen hydrogen bonding between complementary nucleobases. For example, adenine and thymine are complementary nucleobases that pair through the formation of hydrogen bonds.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. In embodiments, the preparation is at least 75%, at least 90%, or at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, HPLC analysis, and the like.

The terms "identical" or "percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software are known in the art that may be used to obtain alignments of amino acid or nucleotide sequences. One such non-limiting example of a sequence alignment algorithm is the algorithm described in Karlin et al., *Proc. Natl. Acad. Sci.*, 87:2264-2268 (1990), as modified in Karlin et al., *Proc. Natl. Acad. Sci.*, 90:5873-5877 (1993), and incorporated into the NBLAST and XBLAST programs (Altschul et al., *Nucleic Acids Res.*, 25:3389-3402 (1991)). In certain embodiments, Gapped BLAST may be used as described in Altschul et al., *Nucleic Acids Res.* 25:3389-3402 (1997). BLAST-2, WU-BLAST-2 (Altschul et al., *Methods in Enzymology*, 266:460-480 (1996)), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain embodiments, the GAP program in the GCG software package, which incorporates the algorithm of Needleman and Wunsch (*J. Mol. Biol.* (48):444-453 (1970)) may be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). In certain embodiments, the percent identity between nucleotide or amino acid sequences is determined using the algorithm of Myers and Miller (CABIOS, 4:11-17 (1989)). For example, the percent identity may be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as $100 \times (Y/Z)$, where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 5, at least about 10, about 20, about 40-60 residues in length or any integral value therebetween, or over a longer region than 60-80 residues, at least about 90-100 residues, or the sequences are substantially identical over the full length of the sequences being compared.

A "conservative amino acid substitution" is one in which one amino acid residue is replaced with another amino acid residue having a similar side chain Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen(s). Methods of identifying nucleotide and amino acid conservative substitutions which do not eliminate antigen binding are well-known in the art (see, e.g., Brummell et al., *Biochem.* 32: 1180-1 187 (1993); Kobayashi et al. *Protein Eng.* 12(10):879-884 (1999); and Burks et al. *Proc. Natl. Acad. Sci. USA* 94:412-417 (1997)).

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or diluent" refers to an excipient, carrier or diluent that can be administered to a subject, together with an agent, and which does not destroy the pharmacological activity thereof and is nontoxic when administered in doses sufficient to deliver a therapeutic amount of the agent.

A "pharmaceutically acceptable salt" of an influenza antibody recited herein is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, $HOOC-(CH_2)_n-COOH$ where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the antibodies provided herein, including those listed by *Remington's Pharmaceutical Sciences*, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

The term "patient" or "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

As used herein, the terms "prevent," "preventing," "prevention," "prophylactic treatment," and the like, refer to reducing the probability of developing a disease or condition in a subject, who does not have, but is at risk of or susceptible to developing a disease or condition.

By "reduces" is meant a negative alteration of at least about 10%, 25%, 50%, 75%, or 100% relative to a reference.

By "reference" is meant a standard or control condition.

By "specifically binds" is meant a compound or antibody that recognizes and binds a polypeptide of the invention, but which does not substantially recognize and bind other molecules in a sample, for example, a biological sample, which naturally includes a polypeptide of the invention.

That an antibody "specifically binds" to an epitope or protein means that the antibody reacts or associates more frequently, more rapidly, with greater duration, with greater affinity, or with some combination of the above to an epitope or protein than with alternative substances, including unrelated proteins. In certain embodiments, "specifically binds" means, for instance, that an antibody binds to a protein with a $K_D$ of about 0.1 mM or less, but more usually less than about 1 μM. In certain embodiments, "specifically binds" means that an antibody binds to a protein at times with a $K_D$ of at least about 0.1 μM or less, and at other times at least about 0.01 μM or less. Because of the sequence identity between homologous proteins in different species, specific binding can include an antibody that recognizes a particular protein in more than one species. It is understood that an antibody or binding moiety that specifically binds to a first target may or may not specifically bind to a second target. As such, "specific binding" does not necessarily require (although it can include) exclusive binding, i.e. binding to a single target. Generally, but not necessarily, reference to binding means specific binding.

As used herein, "substantially pure" refers to material which is at least 50% pure (i.e., free from contaminants), more preferably at least 90% pure, more preferably at least 95% pure, more preferably at least 98% pure, more preferably at least 99% pure.

As used herein, the terms "treat," treating," "treatment," and the like refer to reducing or ameliorating a disorder and/or symptoms associated therewith. By "ameliorate" is meant decrease, suppress, attenuate, diminish, arrest, or stabilize the development or progression of a disease. It will be appreciated that, although not precluded, treating a disorder or condition does not require that the disorder, condition or symptoms associated therewith be completely eliminated.

The term "therapeutic effect" refers to some extent of relief of one or more of the symptoms of a disorder or its associated pathology. The term refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; relief to some extent of one or more of the symptoms associated with the specific infection (e.g., symptoms associated with influenza infection); reduced morbidity and mortality, and improvement in quality of life issues. The above parameters for assessing successful treatment and improvement in the disease are readily measurable by routine procedures familiar to a physician.

"Therapeutically effective amount" is intended to qualify the amount required to achieve a therapeutic effect. A physician or veterinarian having ordinary skill in the art can readily determine and prescribe the "therapeutically effective amount" (e.g., $ED_{50}$) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved.

The phrase "combination therapy" embraces the administration of an influenza antibody and a second therapeutic agent as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days, or weeks depending upon the combination selected). "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. For example, one combination of the present invention comprises an influenza antibody and at least one additional therapeutic agent (e.g., antiviral agent, including anti-influenza agents) at the same or different times or they can be formulated as a single, co-formulated pharmaceutical composition comprising the two compounds. As another example, a combination of the present invention (e.g., an influenza antibody and at least one additional therapeutic agent, such as an antiviral agent) is formulated as separate pharmaceutical compositions that can be administered at the same or different time. Sequential or substantially simultaneous administration of each therapeutic agent can be effected by any appropriate route including, but not limited to, oral routes, intravenous routes, intramuscular routes, and direct absorption through mucous membrane tissues (e.g., nasal, mouth, vaginal, and rectal). The therapeutic agents can be administered by the same route or by different routes. For example, one component of a particular combination may be administered by intravenous injection while the other component(s) of the combination may be administered orally. The components may be administered in any therapeutically effective sequence.

The phrase "combination" embraces groups of compounds or non-drug therapies useful as part of a combination therapy.

The term "vector" means a construct that is capable of delivering and expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DESCRIPTION OF THE DRAWINGS

FIG. 5. Sequences (SEQ ID NOS 52-56, respectively, in order of appearance) at the VDJ recombination site of CH65. The key indicates the origin of the heavy-chain coding segments (V, D, J, and n-nucleotide).

FIG. 6. Heavy chain DNA sequences of CH65-CH67 HA antibodies.

FIG. 7. Light chain DNA sequences of CH65-CH67 HA antibodies.

FIG. 8. Heavy chain amino acid sequences of CH65-CH67 HA antibodies.

FIG. 9. Light chain amino acid sequences of CH65-CH67 HA antibodies.

FIG. 10. Alignment of VH DNA sequences of CL860UCA (SEQ ID NO: 1), CH65(SEQ ID NO: 2), CH66 (SEQ ID NO: 3) and CH67 (SEQ ID NO: 4).

FIG. 11. Alignment of VL DNA sequences of CL860UCA (SEQ ID NO: 5), CH65 (SEQ ID NO: 6), CH66 (SEQ ID NO: 7) and CH67 (SEQ ID NO: 8).

FIG. 12. Alignment of VH amino acid sequences of CL860UCA (SEQ ID NO: 9), CH65 (SEQ ID NO: 10), CH66 (SEQ ID NO: 11) and CH67 (SEQ ID NO: 12).

FIG. 13. Alignment of VL amino acid sequences of CL860UCA (SEQ ID NO: 13), CH65 (SEQ ID NO: 14), CH66 (SEQ ID NO: 15) and CH67 (SEQ ID NO: 16).

FIG. 14. Representative receptor binding domains from H1 (A), H2 (B), H3 (C), and H5 (D) hemagglutinin. The CH65-CH67 antibody binding epitopes are underlined.

FIG. 15. Sequence alignment of representative receptor binding domains from H1, H2, H3, and H5 hemagglutinin (SEQ ID NOS 57-61, respectively, in order of appearance). The amino acid residues that interact with the CH65-CH67 antibodies are underlined.

DETAILED DESCRIPTION OF THE INVENTION

Figure 1A:
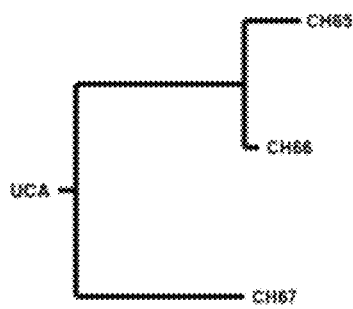
FIG. 1. (A) Inferred lineage of clone 860. Left: the unmutated common ancestor (UCA) of the three antibodies (shown by their numbers, right) isolated from the donor. (B) Alignment of heavy-chain (top) (SEQ ID NOS 51 and 10-12, respectively, in order of appearance) and light-chain (bottom) (SEQ ID NOS 13-16, respectively, in order of appearance) sequences in the lineage. (C) Contact of the Fab from CH65 with HA1. Heavy chain in dark blue; light chain in light blue; CDRs in colors as labeled in (B); HA in red, with the atomic surface shown as a partly transparent overlay. Residues that have mutated from the UCA are in green stick representation.

The invention features novel antibodies that broadly neutralize influenza antigenic variants. The invention also provides compositions and kits containing the novel antibodies, as well as methods for using these novel therapeutic molecules to treat or prevent (e.g., vaccinate) influenza infection.

The receptor for influenza virus is sialic acid, attached by terminal α-2,3 or α-2,6 linkage to glycans on glycoproteins or glycolipids (reviewed in Wiley, D. C. and Skehel, J. J. *Annu. Rev. Biochem.* 56:365-394 (1987)). Most neutralizing antibodies block cell attachment, either because their footprint overlaps the receptor-binding site or because they exert steric interference when bound elsewhere on the HA surface (Knossow, M. and Skehel, J. J. *Immunology* 119:1-7 (2006)). Two mouse monoclonal neutralizing antibodies, for which structures of Fab:HA complexes have been determined, have loops that project into the sialic-acid binding pocket on HA and present an aspartic-acid side chain roughly where the sialic-acid carboxylate would be (Fleury, D. et al., *Nat. Struct. Biol.* 5:119-123 (1998); and Barbey-Martin, C. et al., *Virology* 294:70-74 (2002)). But both of these antibodies also have extensive contacts with other surface regions, in which escape mutations could occur more readily than in the receptor site.

The invention is based, at least in part, on the discovery of novel antibodies having principal contacts in the receptor pocket. One such antibody, designated CH65, was found by isolating rearranged heavy- and light-chain genes from sorted single plasma cells, obtained from a subject who had received the 2007 trivalent vaccine. CH65 neutralizes a remarkably broad range of H1 seasonal isolates spanning more than three decades. Its 19-residue heavy-chain complementarity-determining region 3 (CDR-H3) inserts into the receptor pocket, mimicking many of the interactions made by sialic acid.

Both heavy- and light-chain CDRs participate in more restricted, additional contacts with the outward-facing surface of HA1. The inferred, unmutated ancestor of CH65 differs from the affinity matured antibody at 12 positions in the heavy-chain variable domain, and at 6 in the light-chain variable domain. The human B-cell repertoire thus includes the potential to generate antibodies directed primarily at the receptor binding site. The large number of seasonal H1 viruses neutralized by antibody CH65 suggests that such responses are ordinarily too rare to select for resistance, or that resistance comes at too great a fitness cost—as would be the case if potential escape mutations were to compromise receptor binding. Thus, it is surprising that the inventors have discovered that broad neutralization of influenza virus can be achieved by antibodies with contacts that mimic those of the receptor. Accordingly, the invention provides novel antibodies that mimic the contact between influenza HA and the sialic acid receptor. These novel antibodies can effectively treat and/or prevent infection by drifted strains of influenza. As such, the invention features compositions and kits containing the novel antibodies, as well as methods for using these therapeutic molecules to treat and/or prevent influenza infection. The invention also relates to combination therapies including the novel antibodies.

CH65-CH67 Hemagglutinin Antibodies

The present invention provides novel anti-influenza antibodies that specifically bind to an epitope of an influenza hemagglutinin (HA). Binding of the antibodies to the HA reduces or inhibits influenza hemagglutinin binding to sialic acid.

As stated above, the invention features in certain embodiments, an anti-influenza antibody or antibody fragment that specifically binds to a sialic acid binding domain of a surface antigen of influenza virus. Preferably, the surface antigen of influenza virus is HA.

In embodiments, the epitope of influenza HA comprises a sialic-acid binding domain.

In embodiments, the HA is H1 HA, H2 HA, H3 HA, or H5 HA (an HA from a human adapted H5 strain).

In related embodiments, the antibody or antibody fragment contacts one or more residues in the influenza HA epitope comprising residue: 158; 158-160; 135-136, 190-195, and 226; 222, 225, and 227; and 187 and 189 where the numbering refers to the one used in structures such as that for A/Solomon Islands/3/2006 (Protein Data Bank accession number 3SM5).

In one embodiment, and as stated above, the antibody contacts one or more residues in the sialic acid binding pocket of the HA epitope selected from the group consisting of residue: 134-136, 190-195, and 226.

In another embodiment, and as stated above, the antibody further contacts one or more residues in the HA epitope selected from the group consisting of residue: 158, 158-160, 135-136, 190-195 and 226, and 187 and 189.

As described herein, in certain embodiments, the antibody CDR H1 region contacts residue 158 of the HA epitope; the CDR H2 region contacts residues 158-160 of the HA epitope; the CDR H3 region contacts residues 135-136, 190-194 and 226 of the HA epitope; the CDR L1 region contacts residues 222, 225 and 227 of the HA epitope; or the CDR L3 region contacts residues 187 and 198 of the HA epitope.

In related embodiments, the influenza HA epitope comprises the amino acids set forth in any one of SEQ ID NOs:17-44.

In related embodiments, the influenza HA epitope comprises the CH65-CH67 binding residues in any one of SEQ ID NOs:17-44 (e.g., the CH65-CH67 binding residues identified in FIG. 15).

In embodiments, the anti-influenza antibody or antibody fragment comprises a variable heavy ($V_H$) chain, and wherein the $V_H$ chain comprises an amino acid sequence set forth in SEQ ID NO: 9, SEQ ID NO: 10, SEQ ID NO: 11, or SEQ ID NO: 12.

In embodiments, the anti-influenza antibody or antibody fragment comprises one or more heavy chain CDR regions present in a variable heavy ($V_H$) chain amino acid sequence of SEQ ID NO: 9, SEQ ID NO: 10, SEQ ID NO: 11, or SEQ ID NO: 12. In related embodiments, the one or more heavy chain CDR regions comprises a CDR3 region present in the variable heavy ($V_H$) chain amino acid sequence of SEQ ID NO: 9, SEQ ID NO: 10, SEQ ID NO: 11, or SEQ ID NO: 12.

In embodiments, the anti-influenza antibody or antibody fragment comprises a variable light ($V_L$) chain, and wherein the $V_L$ chain comprises an amino acid sequence set forth in SEQ ID NO: 13, SEQ ID NO: 14, SEQ ID NO: 15, or SEQ ID NO: 16.

In embodiments, the anti-influenza antibody or antibody fragment comprises one or more light chain CDR regions present in a variable light ($V_L$) chain amino acid sequence of SEQ ID NO: 13, SEQ ID NO: 14, SEQ ID NO: 15, or SEQ ID NO: 16. In related embodiments, the one or more light chain CDR regions comprises a CDR3 region present in the variable heavy ($V_L$) chain amino acid sequence of SEQ ID NO: 13, SEQ ID NO: 14, SEQ ID NO: 15, or SEQ ID NO: 16.

In embodiments, the anti-influenza antibody or antibody fragment comprises i) a variable heavy ($V_H$) chain amino comprising an amino acid sequence set forth in SEQ ID NO: 10, and ii) a variable light ($V_L$) chain comprising an amino acid sequence set forth in SEQ ID NO: 14.

In embodiments, the anti-influenza antibody or antibody fragment comprises a variable heavy ($V_H$) chain, wherein the CDR3 region of the $V_H$ chain comprises Arg104, Ser105, Val106, Asp107, Tyr109, Tyr110, Tyr112, or a combination thereof.

In embodiments, the anti-influenza antibody is a monoclonal antibody or antibody fragment thereof.

In embodiments, the anti-influenza antibody is a humanized antibody.

In embodiments, the antibody fragment is an Fab fragment, an Fab' fragment, an Fd fragment, a Fd' fragment, an Fv fragment, a dAb fragment, an F(ab')$_2$ fragment, a single chain fragment, a diabody, or a linear antibody.

In embodiments, the anti-influenza antibody or antibody fragment further comprises an agent conjugated to the anti-influenza antibody or antibody fragment thereof. In related embodiments, the agent conjugated to the antibody or antibody fragment thereof is a therapeutic agent or detectable label.

The therapeutic agent can be any therapeutic agent suitable for use with the novel antibodies. Such agents are well known in the art and include small molecules, nanoparticles, polypeptides, radioisotopes, inhibitory nucleic acids, and the like. In embodiments, the therapeutic agent is an antiviral agent or a toxin. In embodiments, the therapeutic agent is an siRNA, shRNA, or antisense nucleic acid molecule that reduces influenza virus production.

The detectable label can be any detectable label suitable for use with the novel antibodies. Such labels are well known in the art and include labels that are detected by spectroscopic, photochemical, biochemical, immunochemical, physical, or chemical means. In embodiments, the detectable label is an enzyme, a fluorescent molecule, a particle label, an electron-dense reagent, a radiolabel, a microbubble, biotin, digoxigenin, or a hapten or a protein that has been made detectable.

In any of the above embodiments, the influenza can be H1N1, H2N2, H3N2, or a human adapted H5 strain.

The antibodies of the invention can be prepared by any conventional means known in the art. For example, polyclonal antibodies can be prepared by immunizing an animal (e.g., a rabbit, rat, mouse, donkey, goat, hamster, guinea pig, sheep, ungulate, cow, camel, fowl, chicken, and the like) by multiple subcutaneous or intraperitoneal injections of the relevant antigen (e.g., a purified peptide fragment, full-length recombinant protein, fusion protein, and the like) optionally conjugated to suitable hapten (e.g., keyhole limpet hemocyanin (KLH), serum albumin, and the like). The antigens can be diluted in any suitable vehicle (e.g., sterile saline) and combined with an adjuvant (e.g., Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, and the like.

Monoclonal antibodies can be prepared using hybridoma methods, such as those described by Kohler and Milstein, *Nature* 256:495 (1975). Using the hybridoma method, an appropriate host animal is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g., radioimmunoassay (RIA), enzyme-linked immunosorbent assay (ELISA), and the like) can then be propagated either in vitro culture using standard methods (see Goding, *Monoclonal Antibodies: Principles and Practice*, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides (including the isolated polynucleotides described herein) encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (see McCafferty et al., 1990*, Nature,* 348:552-554; Clackson et al., 1991, Nature, 352:624-628; and Marks et al., 1991*, J. Mol. Biol.,* 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments of the present invention, the monoclonal antibody is a humanized antibody. Humanized antibodies are antibodies that contain minimal sequences from non-human (e.g., rodent) antibodies within the antigen determination or hypervariable region that comprise the three complementary determination regions (CDRs) within each antibody chain. Such antibodies are used therapeutically to reduce antigenicity and HAMA (human anti-mouse antibody) responses when administered to a human subject. In practice, humanized antibodies are typically human antibodies with minimum to virtually no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDRs of a human antibody with those of a non-human antibody (e.g., mouse, rat, rabbit, hamster, and the like.) having the desired specificity, affinity, and capability (see, e.g., the methods of Jones et al., *Nature* 321: 522-525 (1986); Riechmann et al., Nature 332:323-327 (1988); and Verhoeyen et al., *Science* 239:1534-1536 (1988). The humanized antibody can be further modified by the substitution of additional residue either in the variable human framework region and/or within the replaced non-human residues to refine and optimize antibody specificity, affinity, and/or capability.

The choice of human heavy and/or light chain variable domains to be used in making humanized antibodies can be important for reducing antigenicity. According to the "best-fit" method, the sequence of the variable domain of a non-human antibody is screened against the entire library of known human variable-domain amino acid sequences. Thus in certain embodiments, the human amino acid sequence which is most homologous to that of the non-human antibody from which the CDRs are taken is used as the human framework region (FR) for the humanized antibody (see Sims et al., *J. Immunol.* 151: 2296 (1993); Chothia et al., *J. Mol. Biol.* 196:901 (1987)). Another method uses a particular FR derived from the consensus sequence of all human antibodies of a particular subgroup of light or heavy chains and can be used for several difference humanized antibodies (see Carter et al., *PNAS* 89; 4285 (1992); Presta et al., *J.*

*Immunol.* 151: 2623 (1993)). In embodiments, a combination of methods is used to pick the human variable FR to use in generation of humanized antibodies.

It is further understood that antibodies to be humanized must retain high affinity for the antigen as well as other favorable biological properties. To achieve this goal, humanized antibodies can be prepared by a process of analysis of the parental sequence from the non-human antibody to be humanized and the various candidate humanizing sequences. Three-dimensional immunoglobulin models are available and familiar to those skilled in the art. Computer programs can be used to illustrate and display probable three-dimensional conformational structures of selected candidate antibody sequences. Use of such models permits analysis of the likely role of the residues in the function of the antibody to be humanized, i.e., the analysis of residues that influence the ability of the candidate antibody to bind its antigen. In this way, FR residues can be selected and combined from the parental antibody to the recipient humanized antibody so that the desired antibody characteristics are achieved. In general, the residues in the CDRs of the antigen determination region (or hypervariable region) are retained from the parental antibody (e.g. the non-human antibody with the desired antigen binding properties) in the humanized antibody for antigen binding. In certain embodiments, at least one additional residue within the variable FR is retained from the parental antibody in the humanized antibody. In certain embodiments, up to six additional residues within the variable FR are retained from the parental antibody in the humanized antibody.

Amino acids from the variable regions of the mature heavy and light chains of immunoglobulins are designated Hx and Lx respectively, where x is a number designating the position of an amino acid according to the scheme of Kabat, Sequences of Proteins of Immunological Interest, U.S. Department of Health and Human Services, 1987, 1991. Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Moreover, any two antibody sequences can be uniquely aligned, for example to determine percent identity, by using the Kabat numbering system so that each amino acid in one antibody sequence is aligned with the amino acid in the other sequence that has the same Kabat number. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

In addition to humanized antibodies, fully human antibodies can be directly prepared using various techniques known in the art Immortalized human B lymphocytes immunized in vitro or isolated from an immunized individual that produce an antibody directed against a target antigen can be generated (See, e.g., Cole et al., *Monoclonal Antibodies and Cancer Therapy*, Alan R. Liss, p. 77 (1985); Boerner et al., *J. Immunol.* 147:86-95 (1991); and U.S. Pat. No. 5,750,373). Also, the human antibody can be selected from a phage library, where that phage library expresses human antibodies (see Vaughan et al., *Nat. Biotech.* 14:309-314 (1996); Sheets et al., *Proc. Nat'l. Acad. Sci.* 95:6157-6162 (1998); Hoogenboom and Winter, *J. Mol. Biol.* 227:381 (1991); and Marks et al., *J. Mol. Biol.* 222:581 (1991)). Human antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies. Bispecific antibodies are antibodies that are capable of specifically recognizing and binding at least two different epitopes. The different epitopes can either be within the same molecule (e.g., influenza HA) or on different molecules such that the bispecific antibody can specifically recognize and bind an epitope in an antigen of interest (e.g., influenza HA) as well as, for example, another viral protein (e.g., neuromimidase, M2, and the like). Bispecific antibodies can be intact antibodies or antibody fragments. Techniques for making bispecific antibodies are common in the art (see Millstein et al., *Nature* 305:537-539 (1983); Brennan et al., *Science* 229:81 (1985); Suresh et al, *Methods in Enzymol.* 121:120 (1986); Traunecker et al., *EMBO J.* 10:3655-3659 (1991); Shalaby et al., *J. Exp. Med.* 175:217-225 (1992); Kostelny et al., *J. Immunol.* 148:1547-1553 (1992); Gruber et al., *J. Immunol.* 152:5368 (1994); and U.S. Pat. No. 5,731,168). Antibodies with more than two valencies are also contemplated. For example, trispecific antibodies can be prepared (see Tutt et al., *J. Immunol.* 147:60 (1991)).

In embodiments, the antibodies of the invention are antibody fragments. Various techniques are known for the production of antibody fragments: Traditionally, these fragments are derived via proteolytic digestion of intact antibodies (see, e.g., Morimoto et al., *Journal of Biochemical and Biophysical Methods* 24:107-117 (1993); and Brennan et al., *Science* 229:81 (1985)). Antibody fragments can also be produced recombinantly. Fab, Fv, and scFv antibody fragments can all be expressed in and secreted from *E. coli* or other host cells, thus allowing the production of large amounts of these fragments. Such antibody fragments can also be isolated from antibody phage libraries as discussed above. The antibody fragment can also be linear antibodies as described in U.S. Pat. No. 5,641,870, for example, and can be monospecific or bispecific. Other techniques for the production of antibody fragments will be readily apparent to the skilled practitioner.

According to the present invention, techniques can be adapted for the production of single-chain antibodies specific to a polypeptide of the invention (see U.S. Pat. No. 4,946,778). In addition, methods can be adapted for the construction of Fab expression libraries (see Huse et al., *Science* 246:1275-1281 (1989)) to allow rapid and effective identification of monoclonal Fab fragments with the desired specificity for influenza HA. Antibody fragments that contain the idiotypes to a polypeptide of the invention may be produced by techniques in the art including, but not limited to: (a) an F(ab')2 fragment produced by pepsin digestion of an antibody molecule; (b) an Fab fragment generated by reducing the disulfide bridges of an F(ab')2 fragment, (c) an Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

Another alteration contemplated by the present invention is that the variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention can comprise antibodies, or immunoreactive fragments thereof, in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein may comprise alterations or modifications to one or more of the three heavy chain constant domains (CH1, CH2 or CH3) and/or to the light chain constant domain (CL). In some embodiments of the invention modified constant regions wherein one or more domains are partially or entirely deleted are contemplated. In some embodiments the modified antibodies will comprise domain deleted constructs or variants wherein the entire CH2 domain has been removed ($\Delta$CH2 constructs). In some embodiments the omitted constant region domain will be replaced by a short amino acid spacer (e.g., 10 residues) that provides some of the molecular flexibility typically imparted by the absent constant region.

The present invention further embraces variants and equivalents which are substantially homologous to the chimeric, humanized and human antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The antibodies of the present invention can be assayed for immunospecific binding by any method known in the art. The immunoassays which can be used include, but are not limited to, competitive and non-competitive assay systems using techniques such as BIAcore analysis, FACS analysis, immunofluorescence, immunocytochemistry, Western blots, radioimmunoassays, ELISA, "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, and the like. Such assays are routine and well known in the art (see, e.g., Ausubel et al, eds, 1994, *Current Protocols in Molecular Biology*, Vol. 1, John Wiley & Sons, Inc., New York, which is incorporated by reference herein in its entirety).

In embodiments, the immunospecificity of an antibody against a influenza HA is determined using ELISA. An ELISA assay comprises preparing antigen, coating wells of a microtiter plate with antigen, adding the antibody conjugated to a detectable compound such as an enzymatic substrate (e.g., horseradish peroxidase or alkaline phosphatase) to the well, incubating for a period of time and detecting the presence of the antigen. In some embodiments, the antibody is not conjugated to a detectable compound, but instead a second conjugated antibody that recognizes the antibody against the influenza HA antigen is added to the well. In some embodiments, instead of coating the well with the antigen, the antibody can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art (see e.g. Ausubel et al, eds, 1994, *Current Protocols in Molecular Biology*, Vol. 1, John Wiley & Sons, Inc., New York at 11.2.1).

The binding affinity of an antibody to influenza HA and the off-rate of an antibody-antigen interaction can be determined by competitive binding assays. One example of a competitive binding assay is a radioimmunoassay comprising the incubation of labeled antigen (e.g. $^3$H or $^{125}$I), or fragment or variant thereof, with the antibody of interest in the presence of increasing amounts of unlabeled antigen followed by the detection of the antibody bound to the labeled antigen. The affinity of the antibody against an antigen and the binding off-rates can be determined from the data by scatchard plot analysis. In some embodiments, BIAcore kinetic analysis is used to determine the binding on and off rates of antibodies against a cancer stem cell marker. BIAcore kinetic analysis comprises analyzing the binding and dissociation of antibodies from chips with immobilized cancer stem cell marker antigens on their surface.

Influenza Hemagglutinin Antibody Polypeptides and Polynucleotides

The present invention also encompasses isolated polynucleotides that encode a polypeptide comprising an influenza hemagglutinin (HA) antibody or fragment thereof.

The term "polynucleotide encoding a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

The present invention further relates to variants of the polynucleotides, for example, fragments, analogs, and derivatives. The variant of the polynucleotide can be a naturally occurring allelic variant of the polynucleotide or a non-naturally occurring variant of the polynucleotide. In certain embodiments, the polynucleotide can have a coding sequence which is a naturally occurring allelic variant of the coding sequence of the disclosed polypeptides. As known in the art, an allelic variant is an alternate form of a polynucleotide sequence that have, for example, a substitution, deletion, or addition of one or more nucleotides, which does not substantially alter the function of the encoded polypeptide.

In embodiments, the polynucleotides can comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In embodiments, the polynucleotides can comprise the coding sequence for the mature polypeptide fused in the same reading frame to a marker sequence that allows, for example, for purification of the encoded polypeptide. For example, the marker sequence can be a hexa-histidine tag (SEQ ID NO: 46) supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. Additional tags include, but are not limited to, Calmodulin tags, FLAG tags, Myc tags, S tags, SBP tags, Softag 1, Softag 3, V5 tag, Xpress tag, Isopeptag, SpyTag, Biotin Carboxyl Carrier Protein (BCCP) tags, GST tags, fluorescent protein tags (e.g., green fluorescent protein tags), maltose binding protein tags, Nus tags, Strep-tag, thioredoxin tag, TC tag, Ty tag, and the like.

In embodiments, the present invention provides isolated nucleic acid molecules having a nucleotide sequence at least 80% identical, at least 85% identical, at least 90% identical, at least 95% identical, or at least 96%, 97%, 98% or 99% identical to a polynucleotide encoding a polypeptide comprising an influenza HA antibody or antibody fragment of the present invention.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80% identical, at least 85% identical, at least 90% identical, and in some embodiments, at least 95%, 96%, 97%, 98%, or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The polynucleotide variants can contain alterations in the coding regions, non-coding regions, or both. In some embodiments, the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as E. coli).

The polypeptides of the present invention can be recombinant polypeptides, natural polypeptides, or synthetic polypeptides comprising an antibody, or fragment thereof, against influenza HA. It will be recognized in the art that some amino acid sequences of the invention can be varied without significant effect of the structure or function of the protein. Thus, the invention further includes variations of the polypeptides which show substantial activity or which include regions of a humanized antibody, or fragment thereof, against influenza HA. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in Remington's Pharmaceutical Sciences, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., *Proc. Nat'l. Acad. Sci.* USA 81:5662-5066 (1984) and U.S. Pat. No. 4,588,585.

In embodiments, a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (e.g., by synthesis, site-directed mutagenesis, or another method), the polynucleotide sequences encoding a particular isolated polypeptide of interest will be inserted into an expression vector and optionally operatively linked to an expression control sequence appropriate for expression of the protein in a desired host. Proper assembly can be confirmed by nucleotide sequencing, restriction mapping, and expression of a biologically active polypeptide in a suitable host. As well known in the art, in order to obtain high expression levels of a transfected gene in a host, the gene can be operatively linked to transcriptional and translational expression control sequences that are functional in the chosen expression host.

Recombinant expression vectors are used to amplify and express DNA encoding the influenza HA antibodies. Recombinant expression vectors are replicable DNA constructs which have synthetic or cDNA-derived DNA fragments encoding an influenza HA antibody or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous, and in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a polypeptide include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are well known in the art (see Pouwels et al., *Cloning Vectors: A Laboratory Manual*, Elsevier, N.Y., 1985).

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, *Bio/Technology* 6:47 (1988).

The proteins produced by a transformed host can be purified according to any suitable method. Such standard methods include chromatography (e.g., ion exchange, affinity and sizing column chromatography, and the like), centrifugation, differential solubility, or by any other standard technique for protein purification. Affinity tags such as hexahistidine, maltose binding domain, influenza coat sequence, glutathione-S-transferase, and the like can be attached to the protein to allow easy purification by passage over an appropriate affinity column Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a cancer stem cell protein-Fc composition. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods of Treatment

The present invention provides methods for treating or preventing influenza infection.

In aspects, the invention provides methods for treating or preventing an influenza virus infection in a subject in need thereof. The methods involve administering to the subject an effective amount of an anti-influenza antibody or antibody fragment described herein, or a pharmaceutical composition containing the antibody or antibody fragment. The methods treat or prevent influenza virus infection in the subject, including reducing or alleviating symptoms associated with infection.

In aspects, the invention provides methods for neutralizing an influenza virus in a subject in need thereof. The methods involve administering to the subject an effective amount of an anti-influenza antibody or antibody fragment described herein, or a pharmaceutical composition containing the antibody or antibody fragment. The methods neutralize the influenza virus in the subject, thereby treating or prevent influenza virus infection in the subject, including reducing or alleviating symptoms associated with infection.

In aspects, the invention provides methods for establishment of influenza virus infection in a subject in need thereof. The methods involve administering to the subject an effective amount of an anti-influenza antibody or antibody fragment described herein, or a pharmaceutical composition containing the antibody or antibody fragment. The methods inhibit establishment of influenza virus infection in the subject, thereby preventing symptoms associated with infection.

In aspects, the invention provides methods for inhibiting dissemination of influenza virus infection in a subject in need thereof. The methods involve administering to the subject an effective amount of an anti-influenza antibody or antibody fragment described herein, or a pharmaceutical composition containing the antibody or antibody fragment. The methods inhibit dissemination of influenza virus infection in the subject, thereby reducing or alleviating symptoms associated with infection.

In aspects, the invention provides methods for inhibiting influenza virus entry into a cell in a subject. The methods involve administering to the subject an effective amount of an anti-influenza antibody or antibody fragment described herein, or a pharmaceutical composition containing the antibody or antibody fragment. The methods inhibit influenza virus entry into a cell in the subject, thereby preventing symptoms associated with infection or reducing or alleviating symptoms associated with infection.

In aspects, the invention provides methods for inhibiting influenza virus entry into a cell. The methods involve contacting a cell having or at risk of developing influenza virus infection with an anti-influenza antibody or antibody fragment described herein, or a pharmaceutical composition containing the antibody or antibody fragment. The methods inhibit influenza virus entry into the cell.

In any of the above aspects, the influenza can be H1N1, H2N2, H3N2, or a human adapted H5 strain.

In any of the above aspects, the subject has or is at risk of developing an influenza infection. In related embodiments, the subject is a mammal (e.g., human). In related embodiments, the subject is susceptible to viral infection (e.g., a pregnant female, a young subject or an infant subject, an elderly subject).

In any of the above aspects and embodiments, the anti-influenza antibody or antibody fragment, or the pharmaceutical composition is administered by intramuscular injection, intravenous injection, subcutaneous injection, or inhalation.

Pharmaceutical Compositions

The invention provides for pharmaceutical compositions containing the novel influenza HA antibodies described herein. In embodiments, the pharmaceutical compositions contain a pharmaceutically acceptable carrier, excipient, or diluent, which includes any pharmaceutical agent that does not itself induce the production of an immune response harmful to a subject receiving the composition, and which may be administered without undue toxicity. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful for treating and/or preventing influenza infection.

A thorough discussion of pharmaceutically acceptable carriers, diluents, and other excipients is presented in *Remington's Pharmaceutical Sciences* (17th ed., Mack Publishing Company) and *Remington: The Science and Practice of Pharmacy* (21st ed., Lippincott Williams & Wilkins), which are hereby incorporated by reference. The formulation of the pharmaceutical composition should suit the mode of administration. In embodiments, the pharmaceutical composition is suitable for administration to humans, and can be sterile, non-particulate and/or non-pyrogenic.

Pharmaceutically acceptable carriers, excipients, or diluents include, but are not limited, to saline, buffered saline, dextrose, water, glycerol, ethanol, sterile isotonic aqueous buffer, and combinations thereof.

Wetting agents, emulsifiers and lubricants, such as sodium lauryl sulfate and magnesium stearate, as well as coloring agents, release agents, coating agents, sweetening, flavoring and perfuming agents, preservatives, and antioxidants can also be present in the compositions.

Examples of pharmaceutically-acceptable antioxidants include, but are not limited to: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

In embodiments, the pharmaceutical composition is provided in a solid form, such as a lyophilized powder suitable for reconstitution, a liquid solution, suspension, emulsion, tablet, pill, capsule, sustained release formulation, or powder.

In embodiments, the pharmaceutical composition is supplied in liquid form, for example, in a sealed container indicating the quantity and concentration of the active ingredient in the pharmaceutical composition. In related embodiments, the liquid form of the pharmaceutical composition is supplied in a hermetically sealed container.

Methods for formulating the pharmaceutical compositions of the present invention are conventional and well-known in the art (see Remington and Remington's). One of skill in the art can readily formulate a pharmaceutical composition having the desired characteristics (e.g., route of administration, biosafety, and release profile).

Methods for preparing the pharmaceutical compositions include the step of bringing into association the active ingredient with a pharmaceutically acceptable carrier and, optionally, one or more accessory ingredients. The pharmaceutical compositions can be prepared by uniformly and intimately bringing into association the active ingredient with liquid carriers, or finely divided solid carriers, or both, and then, if necessary, shaping the product. Additional methodology for preparing the pharmaceutical compositions, including the preparation of multilayer dosage forms, are described in *Ansel's Pharmaceutical Dosage Forms and Drug Delivery Systems* (9th ed., Lippincott Williams & Wilkins), which is hereby incorporated by reference.

Methods of Delivery

The pharmaceutical compositions of the invention can be administered to a subject by oral and non-oral means (e.g., topically, transdermally, or by injection). Such modes of administration and the methods for preparing an appropriate pharmaceutical composition for use therein are described in *Gibaldi's Drug Delivery Systems in Pharmaceutical Care* (1st ed., American Society of Health-System Pharmacists), which is hereby incorporated by reference.

In embodiments, the pharmaceutical compositions are administered orally in a solid form.

Pharmaceutical compositions suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound(s) described herein, a derivative thereof, or a pharmaceutically acceptable salt or prodrug thereof as the active ingredient(s). The active ingredient can also be administered as a bolus, electuary, or paste.

In solid dosage forms for oral administration (e.g., capsules, tablets, pills, dragees, powders, granules and the like), the active ingredient is mixed with one or more pharmaceutically acceptable carriers, excipients, or diluents, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions can also comprise buffering agents. Solid compositions of a similar type can also be prepared using fillers in soft and hard-filled gelatin capsules, and excipients such as lactose or milk sugars, as well as high molecular weight polyethylene glycols and the like.

A tablet can be made by compression or molding, optionally with one or more accessory ingredients. Compressed tablets can be prepared using binders (for example, gelatin or hydroxypropylmethyl cellulose), lubricants, inert diluents, preservatives, disintegrants (for example, sodium starch glycolate or cross-linked sodium carboxymethyl cellulose), surface-actives, and/or dispersing agents. Molded tablets can be made by molding in a suitable machine a mixture of the powdered active ingredient moistened with an inert liquid diluent.

The tablets and other solid dosage forms, such as dragees, capsules, pills, and granules, can optionally be scored or prepared with coatings and shells, such as enteric coatings and other coatings well-known in the art.

The pharmaceutical compositions can also be formulated so as to provide slow, extended, or controlled release of the active ingredient therein using, for example, hydroxypropylmethyl cellulose in varying proportions to provide the desired release profile, other polymer matrices, liposomes and/or microspheres. The pharmaceutical compositions can also optionally contain opacifying agents and may be of a composition that releases the active ingredient(s) only, or preferentially, in a certain portion of the gastrointestinal tract, optionally, in a delayed manner. Examples of embedding compositions include polymeric substances and waxes. The active ingredient can also be in micro-encapsulated form, if appropriate, with one or more pharmaceutically acceptable carriers, excipients, or diluents well-known in the art (see, e.g., Remington and Remington's).

The pharmaceutical compositions can be sterilized by, for example, filtration through a bacteria-retaining filter, or by incorporating sterilizing agents in the form of sterile solid compositions which can be dissolved in sterile water, or some other sterile injectable medium immediately before use.

In embodiments, the pharmaceutical compositions are administered orally in a liquid form.

Liquid dosage forms for oral administration of an active ingredient include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. In addition to inert diluents, the liquid pharmaceutical compositions can include adjuvants such as wetting agents, emulsifying and suspending agents, sweetening, flavoring, coloring, perfuming and preservative agents, and the like.

Suspensions, in addition to the active ingredient(s) can contain suspending agents such as, but not limited to, ethoxylated isostearyl alcohols, polyoxyethylene sorbitol and sorbitan esters, microcrystalline cellulose, aluminum metahydroxide, bentonite, agar-agar and tragacanth, and mixtures thereof.

In embodiments, the pharmaceutical compositions are administered by non-oral means such as by topical application, transdermal application, injection, and the like. In related embodiments, the pharmaceutical compositions are administered parenterally by injection, infusion, or implantation (e.g., intravenous, intramuscular, intraarticular, subcutaneous, and the like).

Compositions for parenteral use can be presented in unit dosage forms, e.g. in ampoules or in vials containing several doses, and in which a suitable preservative can be added. Such compositions can be in form of a solution, a suspension, an emulsion, an infusion device, a delivery device for implantation, or it can be presented as a dry powder to be reconstituted with water or another suitable vehicle before use. One or more co-vehicles, such as ethanol, can also be employed. Apart from the active ingredient(s), the compositions can contain suitable parenterally acceptable carriers and/or excipients or the active ingredient(s) can be incorporated into microspheres, microcapsules, nanoparticles, liposomes, or the like for controlled release. Furthermore, the compositions can also contain suspending, solubilising, stabilising, pH-adjusting agents, and/or dispersing agents.

The pharmaceutical compositions can be in the form of sterile injections. To prepare such a composition, the active ingredient is dissolved or suspended in a parenterally acceptable liquid vehicle. Exemplary vehicles and solvents include, but are not limited to, water, water adjusted to a suitable pH by addition of an appropriate amount of hydrochloric acid, sodium hydroxide or a suitable buffer, 1,3-butanediol, Ringer's solution and isotonic sodium chloride solution. The pharmaceutical composition can also contain one or more preservatives, for example, methyl, ethyl or n-propyl p-hydroxybenzoate. To improve solubility, a dissolution enhancing or solubilising agent can be added or the solvent can contain 10-60% w/w of propylene glycol or the like.

The pharmaceutical compositions can contain one or more pharmaceutically acceptable sterile isotonic aqueous or nonaqueous solutions, dispersions, suspensions or emulsions, or sterile powders, which can be reconstituted into sterile injectable solutions or dispersions just prior to use. Such pharmaceutical compositions can contain antioxidants; buffers; bacteriostats; solutes, which render the formulation isotonic with the blood of the intended recipient; suspending agents; thickening agents; preservatives; and the like.

Examples of suitable aqueous and nonaqueous carriers, which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In some embodiments, in order to prolong the effect of an active ingredient, it is desirable to slow the absorption of the compound from subcutaneous or intramuscular injection. This can be accomplished by the use of a liquid suspension of crystalline or amorphous material having poor water solubility. The rate of absorption of the active ingredient then depends upon its rate of dissolution which, in turn, can depend upon crystal size and crystalline form. Alternatively, delayed absorption of a parenterally-administered active ingredient is accomplished by dissolving or suspending the compound in an oil vehicle. In addition, prolonged absorption of the injectable pharmaceutical form can be brought about by the inclusion of agents that delay absorption such as aluminum monostearate and gelatin.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices.

Materials for use in the preparation of microspheres and/or microcapsules include biodegradable/bioerodible polymers such as polyglactin, poly-(isobutyl cyanoacrylate), poly(2-hydroxyethyl-L-glutamine) and poly(lactic acid).

Biocompatible carriers which can be used when formulating a controlled release parenteral formulation include carbohydrates such as dextrans, proteins such as albumin, lipoproteins or antibodies.

Materials for use in implants can be non-biodegradable, e.g., polydimethylsiloxane, or biodegradable such as, e.g., poly(caprolactone), poly(lactic acid), poly(glycolic acid) or poly(ortho esters).

In embodiments, the active ingredient(s) are administered by aerosol. This is accomplished by preparing an aqueous aerosol, liposomal preparation, or solid particles containing the compound. A nonaqueous (e.g., fluorocarbon propellant) suspension can be used. The pharmaceutical composition can also be administered using a sonic nebulizer, which would minimize exposing the agent to shear, which can result in degradation of the compound.

Ordinarily, an aqueous aerosol is made by formulating an aqueous solution or suspension of the active ingredient(s) together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Dosage forms for topical or transdermal administration of an active ingredient(s) includes powders, sprays, ointments, pastes, creams, lotions, gels, solutions, patches and inhalants. The active ingredient(s) can be mixed under sterile conditions with a pharmaceutically acceptable carrier, and with any preservatives, buffers, or propellants as appropriate.

Transdermal patches suitable for use in the present invention are disclosed in *Transdermal Drug Delivery: Developmental Issues and Research Initiatives* (Marcel Dekker Inc., 1989) and U.S. Pat. Nos. 4,743,249, 4,906,169, 5,198,223, 4,816,540, 5,422,119, 5,023,084, which are hereby incorporated by reference. The transdermal patch can also be any transdermal patch well-known in the art, including transscrotal patches. Pharmaceutical compositions in such transdermal patches can contain one or more absorption enhancers or skin permeation enhancers well-known in the art (see, e.g., U.S. Pat. Nos. 4,379,454 and 4,973,468, which are hereby incorporated by reference). Transdermal therapeutic systems for use in the present invention can be based on iontophoresis, diffusion, or a combination of these two effects.

Transdermal patches have the added advantage of providing controlled delivery of active ingredient(s) to the body. Such dosage forms can be made by dissolving or dispersing the active ingredient(s) in a proper medium. Absorption enhancers can also be used to increase the flux of the active ingredient across the skin. The rate of such flux can be controlled by either providing a rate controlling membrane or dispersing the active ingredient(s) in a polymer matrix or gel.

Such pharmaceutical compositions can be in the form of creams, ointments, lotions, liniments, gels, hydrogels, solutions, suspensions, sticks, sprays, pastes, plasters and other kinds of transdermal drug delivery systems. The compositions can also include pharmaceutically acceptable carriers or excipients such as emulsifying agents, antioxidants, buffering agents, preservatives, humectants, penetration enhancers, chelating agents, gel-forming agents, ointment bases, perfumes, and skin protective agents.

Examples of emulsifying agents include, but are not limited to, naturally occurring gums, e.g. gum acacia or gum tragacanth, naturally occurring phosphatides, e.g. soybean lecithin and sorbitan monooleate derivatives.

Examples of antioxidants include, but are not limited to, butylated hydroxy anisole (BHA), ascorbic acid and derivatives thereof, tocopherol and derivatives thereof, and cysteine.

Examples of preservatives include, but are not limited to, parabens, such as methyl or propyl p-hydroxybenzoate and benzalkonium chloride.

Examples of humectants include, but are not limited to, glycerin, propylene glycol, sorbitol and urea.

Examples of penetration enhancers include, but are not limited to, propylene glycol, DMSO, triethanolamine, N,N-dimethylacetamide, N,N-dimethylformamide, 2-pyrrolidone and derivatives thereof, tetrahydrofurfuryl alcohol, propylene glycol, diethylene glycol monoethyl or monomethyl ether with propylene glycol monolaurate or methyl laurate, eucalyptol, lecithin, Transcutol®, and Azone®.

Examples of chelating agents include, but are not limited to, sodium EDTA, citric acid and phosphoric acid.

Examples of gel forming agents include, but are not limited to, Carbopol, cellulose derivatives, bentonite, alginates, gelatin and polyvinylpyrrolidone.

In addition to the active ingredient(s), the ointments, pastes, creams, and gels of the present invention can contain excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain excipients such as lactose, talc, silicic acid, aluminum hydroxide, calcium silicates and polyamide powder, or mixtures of these substances. Sprays can additionally contain customary propellants, such as chlorofluorohydrocarbons, and volatile unsubstituted hydrocarbons, such as butane and propane.

Injectable depot forms are made by forming microencapsule matrices of compound(s) of the invention in biodegradable polymers such as polylactide-polyglycolide. Depending on the ratio of compound to polymer, and the nature of the particular polymer employed, the rate of compound release can be controlled. Examples of other biodegradable polymers include poly(orthoesters) and poly(anhydrides). Depot injectable formulations are also prepared by entrapping the drug in liposomes or microemulsions which are compatible with body tissue.

Subcutaneous implants are well-known in the art and are suitable for use in the present invention. Subcutaneous implantation methods are preferably non-irritating and mechanically resilient. The implants can be of matrix type, of reservoir type, or hybrids thereof. In matrix type devices, the carrier material can be porous or non-porous, solid or semi-solid, and permeable or impermeable to the active compound or compounds. The carrier material can be biodegradable or may slowly erode after administration. In some instances, the matrix is non-degradable but instead relies on the diffusion of the active compound through the matrix for the carrier material to degrade. Alternative subcutaneous implant methods utilize reservoir devices where the active compound or compounds are surrounded by a rate controlling membrane, e.g., a membrane independent of component concentration (possessing zero-order kinetics). Devices consisting of a matrix surrounded by a rate controlling membrane also suitable for use.

Both reservoir and matrix type devices can contain materials such as polydimethylsiloxane, such as Silastic™, or other silicone rubbers. Matrix materials can be insoluble polypropylene, polyethylene, polyvinyl chloride, ethylvinyl acetate, polystyrene and polymethacrylate, as well as glycerol esters of the glycerol palmitostearate, glycerol stearate, and glycerol behenate type. Materials can be hydrophobic or hydrophilic polymers and optionally contain solubilising agents.

Subcutaneous implant devices can be slow-release capsules made with any suitable polymer, e.g., as described in U.S. Pat. Nos. 5,035,891 and 4,210,644, which are hereby incorporated by reference.

In general, at least four different approaches are applicable in order to provide rate control over the release and transdermal permeation of a drug compound. These approaches are: membrane-moderated systems, adhesive diffusion-controlled systems, matrix dispersion-type systems and microreservoir systems. It is appreciated that a controlled release percutaneous and/or topical composition can be obtained by using a suitable mixture of these approaches.

In a membrane-moderated system, the active ingredient is present in a reservoir which is totally encapsulated in a shallow compartment molded from a drug-impermeable laminate, such as a metallic plastic laminate, and a rate-controlling polymeric membrane such as a microporous or a non-porous polymeric membrane, e.g., ethylene-vinyl acetate copolymer. The active ingredient is released through the rate controlling polymeric membrane. In the drug reservoir, the active ingredient can either be dispersed in a solid polymer matrix or suspended in an unleachable, viscous liquid medium such as silicone fluid. On the external surface of the polymeric membrane, a thin layer of an adhesive polymer is applied to achieve an intimate contact of the transdermal system with the skin surface. The adhesive polymer is preferably a polymer which is hypoallergenic and compatible with the active drug substance.

In an adhesive diffusion-controlled system, a reservoir of the active ingredient is formed by directly dispersing the active ingredient in an adhesive polymer and then by, e.g., solvent casting, spreading the adhesive containing the active ingredient onto a flat sheet of substantially drug-impermeable metallic plastic backing to form a thin drug reservoir layer.

A matrix dispersion-type system is characterized in that a reservoir of the active ingredient is formed by substantially homogeneously dispersing the active ingredient in a hydrophilic or lipophilic polymer matrix. The drug-containing polymer is then molded into disc with a substantially well-defined surface area and controlled thickness. The adhesive polymer is spread along the circumference to form a strip of adhesive around the disc.

A microreservoir system can be considered as a combination of the reservoir and matrix dispersion type systems. In this case, the reservoir of the active substance is formed by first suspending the drug solids in an aqueous solution of water-soluble polymer and then dispersing the drug suspension in a lipophilic polymer to form a multiplicity of unleachable, microscopic spheres of drug reservoirs.

Any of the above-described controlled release, extended release, and sustained release compositions can be formulated to release the active ingredient in about 30 minutes to about 1 week, in about 30 minutes to about 72 hours, in about 30 minutes to 24 hours, in about 30 minutes to 12 hours, in about 30 minutes to 6 hours, in about 30 minutes to 4 hours, and in about 3 hours to 10 hours. In embodiments, an effective concentration of the active ingredient(s) is sustained in a subject for 4 hours, 6 hours, 8 hours, 10 hours, 12 hours, 16 hours, 24 hours, 48 hours, 72 hours, or more after administration of the pharmaceutical compositions to the subject.

Dosages

When the agents described herein are administered as pharmaceuticals to humans and animals, they can be given per se or as a pharmaceutical composition containing active ingredient in combination with a pharmaceutically acceptable carrier, excipient, or diluent.

Actual dosage levels and time course of administration of the active ingredients in the pharmaceutical compositions of the invention can be varied so as to obtain an amount of the active ingredient which is effective to achieve the desired therapeutic response for a particular patient, composition, and mode of administration, without being toxic to the patient. Generally, agents or pharmaceutical compositions of the invention are administered in an amount sufficient to reduce or eliminate symptoms associated with influenza infection.

Exemplary dose ranges include 0.01 mg to 250 mg per day, 0.01 mg to 100 mg per day, 1 mg to 100 mg per day, 10 mg to 100 mg per day, 1 mg to 10 mg per day, and 0.01 mg to 10 mg per day. A preferred dose of an agent is the maximum that a patient can tolerate and not develop serious or unacceptable side effects. In embodiments, the agent is administered at a concentration of about 10 micrograms to about 100 mg per kilogram of body weight per day, about 0.1 to about 10 mg/kg per day, or about 1.0 mg to about 10 mg/kg of body weight per day.

In embodiments, the pharmaceutical composition comprises an agent in an amount ranging between 1 and 10 mg, such as 1, 2, 3, 4, 5, 6, 7, 8, 9, or 10 mg.

In embodiments, the therapeutically effective dosage produces a serum concentration of an agent of from about 0.1 ng/ml to about 50-100 µg/ml. The pharmaceutical compositions typically should provide a dosage of from about 0.001 mg to about 2000 mg of compound per kilogram of body weight per day. For example, dosages for systemic administration to a human patient can range from 1-10 µg/kg, 20-80 µg/kg, 5-50 µg/kg, 75-150 µg/kg, 100-500 µg/kg, 250-750 µg/kg, 500-1000 µg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 1500-2000 mg/kg, 5 mg/kg, 20 mg/kg, 50 mg/kg, 100 mg/kg, 500 mg/kg, 1000 mg/kg, 1500 mg/kg, or 2000 mg/kg. Pharmaceutical dosage unit forms are prepared to provide from about 1 mg to about 5000 mg, for example from about 100 to about 2500 mg of the compound or a combination of essential ingredients per dosage unit form.

In embodiments, about 50 nM to about 1 µM of an agent is administered to a subject. In related embodiments, about 50-100 nM, 50-250 nM, 100-500 nM, 250-500 nM, 250-750 nM, 500-750 nM, 500 nM to 1 µM, or 750 nM to 1 µM of an agent is administered to a subject.

Determination of an effective amount is well within the capability of those skilled in the art, especially in light of the detailed disclosure provided herein. Generally, an efficacious or effective amount of an agent is determined by first administering a low dose of the agent(s) and then incrementally increasing the administered dose or dosages until a desired effect (e.g., reduced symptoms associated with influenza infection) is observed in the treated subject, with minimal or acceptable toxic side effects. Applicable methods for determining an appropriate dose and dosing schedule for administration of a pharmaceutical composition of the present invention are described, for example, in *Goodman and Gilman's The Pharmacological Basis of Therapeutics*, Goodman et al., eds., 11th Edition, McGraw-Hill 2005, and *Remington: The Science and Practice of Pharmacy*, 20th and 21st Editions, Gennaro and University of the Sciences in Philadelphia, Eds., Lippencott Williams & Wilkins (2003 and 2005), each of which is hereby incorporated by reference.

Combination Therapies

The agents and pharmaceutical compositions described herein can also be administered in combination with another therapeutic molecule. The therapeutic molecule can be any compound used to treat influenza infection. Examples of such compounds include, but are not limited to, inhibitory nucleic acids that reduce influenza virus production, antiviral agents (e.g., amantadine, rimantadine, zanamivir, oseltamivir, and the like), toxins, and agents that reduce the symptoms associated with influenza infection (e.g., anti-inflammatories).

The influenza HA antibody can be administered before, during, or after administration of the additional therapeutic agent. In embodiments, the antibody is administered before the first administration of the additional therapeutic agent. In embodiments, the antibody is administered after the first administration of the additional therapeutic agent (e.g., 1, 2, 3, 4, 5, 6, 7, 8, 9, 10, 11, 12, 13, 14 days or more). In embodiments, the antibody is administered simultaneously with the first administration of the additional therapeutic agent.

The amount of therapeutic agent administered to a subject can readily be determined by the attending physician or veterinarian. Generally, an efficacious or effective amount of an antibody and an additional therapeutic is determined by first administering a low dose of one or both active agents and then incrementally increasing the administered dose or dosages until a desired effect is observed (e.g., reduced influenza infection symptoms), with minimal or no toxic side effects. Applicable methods for determining an appropriate dose and dosing schedule for administration of a combination of the present invention are described, for example, in *Goodman and Gilman's The Pharmacological*

Basis of Therapeutics, 11th Edition., supra, and in *Remington: The Science and Practice of Pharmacy*, 20th and 21st Editions, supra.

Kits

The invention provides for kits for preventing or treating influenza infection; neutralizing an influenza virus; inhibiting establishment of influenza virus infection; inhibiting dissemination of influenza virus infection; as well as inhibiting influenza virus entry into a cell. In embodiments, the kit contains one or more agents or pharmaceutical compositions described herein. In embodiments, the kit provides instructions for use. The instructions for use can pertain to any of the methods described herein. In related embodiments, the instructions pertain to using the agent(s) or pharmaceutical composition(s) for treating or preventing influenza infection. Kits according to this aspect of the invention may comprise a carrier means, such as a box, carton, tube or the like, having in close confinement therein one or more container means, such as vials, tubes, ampules, bottles and the like. In embodiments, the kit provides a notice in the form prescribed by a governmental agency regulating the manufacture, use, or sale of pharmaceuticals or biological products, which notice reflects approval by the agency of manufacture, use or sale of the kit and the components therein for human administration.

EXAMPLES

It should be appreciated that the invention should not be construed to be limited to the examples that are now described; rather, the invention should be construed to include any and all applications provided herein and all equivalent variations within the skill of the ordinary artisan.

Example 1

The Clonal Lineage of a Broadly Neutralizing Antibody

Figure 1B:
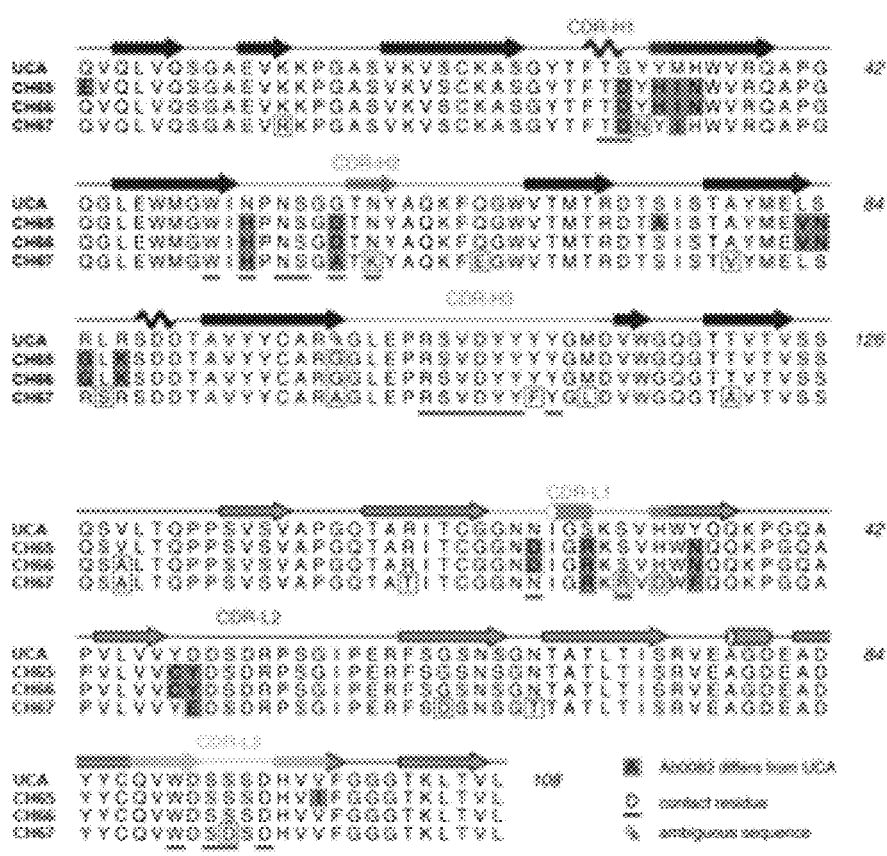
Figure 1C:
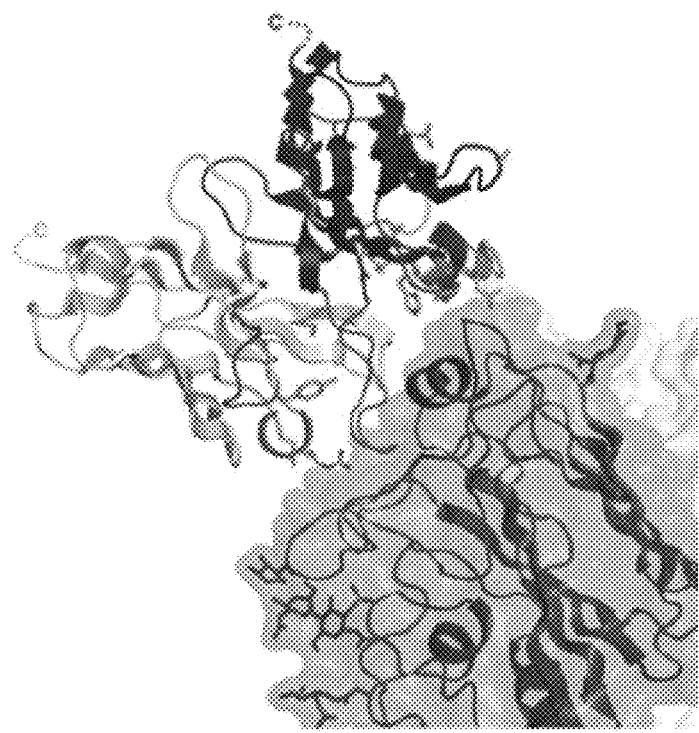
Figure 2A:
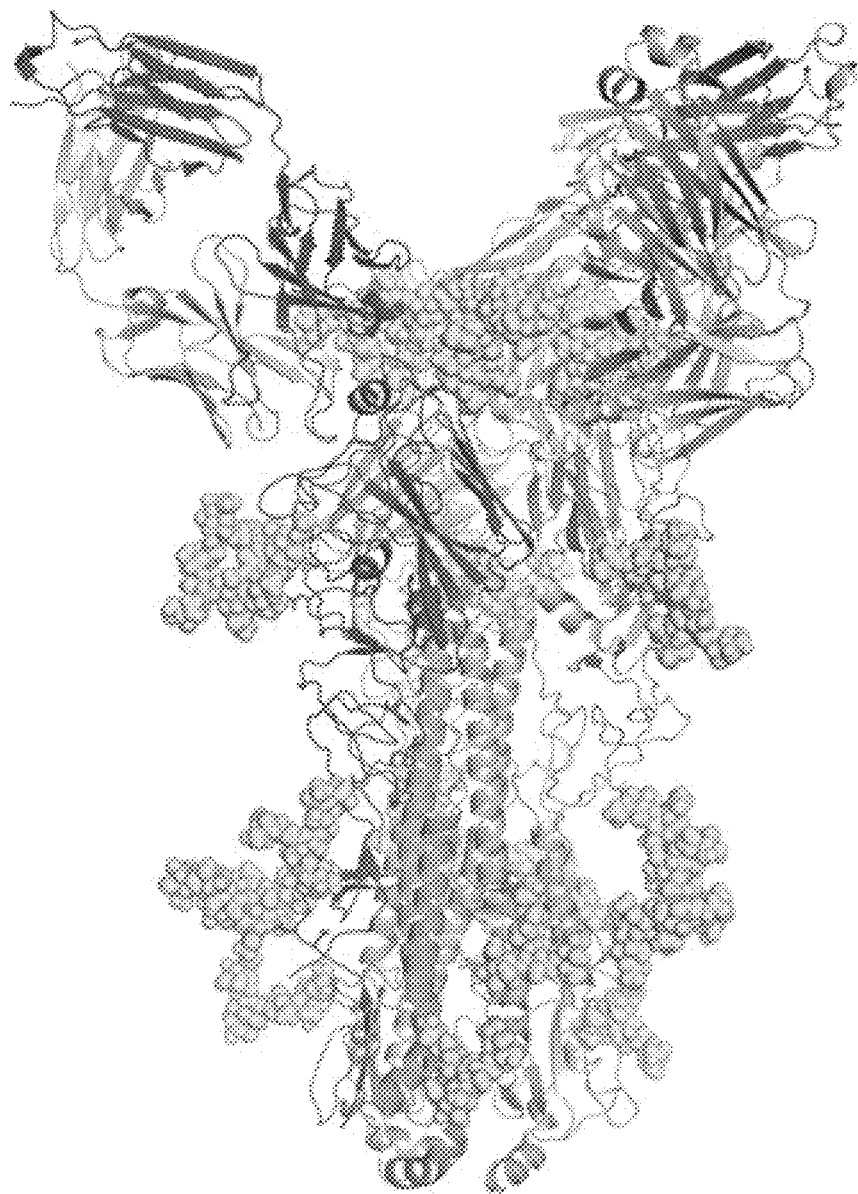
FIG. 2. (A) HA trimer with bound CH65 Fab. One HA chain is in red (HA1) and green (HA2); the other two chains are in gray; glycans are in yellow. The Fab bound to the colored HA chain is in dark blue (heavy chain) and light blue (light chain), with the contacting CDRs in colors as labeled in FIG. 1B. (B) Blow up of the Fv region and its contact with HA1. Colors as in FIG. 1. Note that the heavy-chain CDR3 (magenta) projects into the receptor-binding pocket on HA1, while the remaining CDRs have more limited surface contacts. (C) and (D) Surface representation of the contact between Fab CH65 and HA1, opened up as shown by the arrows. The sialic-acid pocket on one HA subunit is in dark red; the rest of the subunit, in dull red; the remaining two subunits, in gray; glycans, in yellow.
Figure 2B:
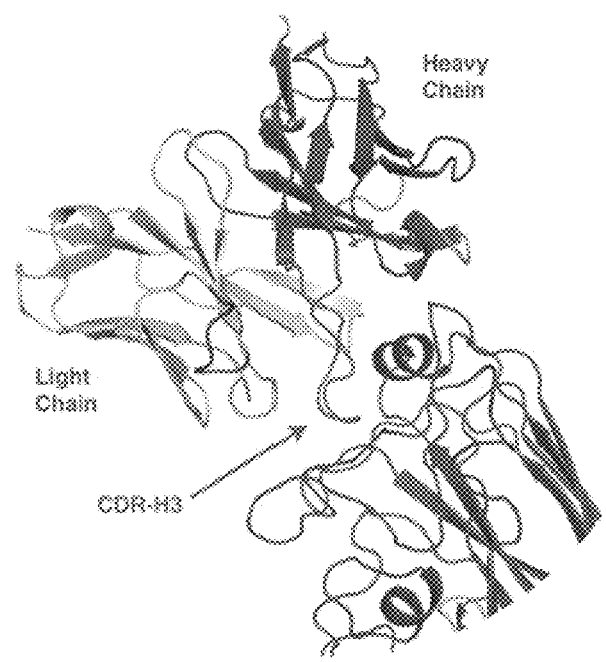
Figure 2C:
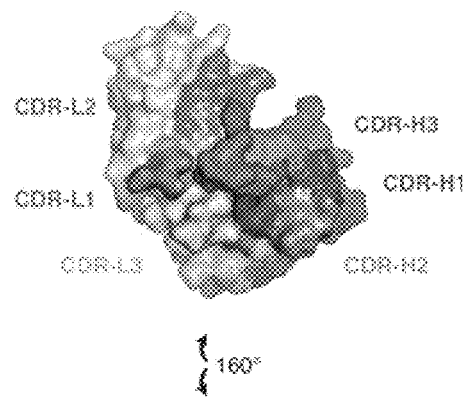
Figure 2D:
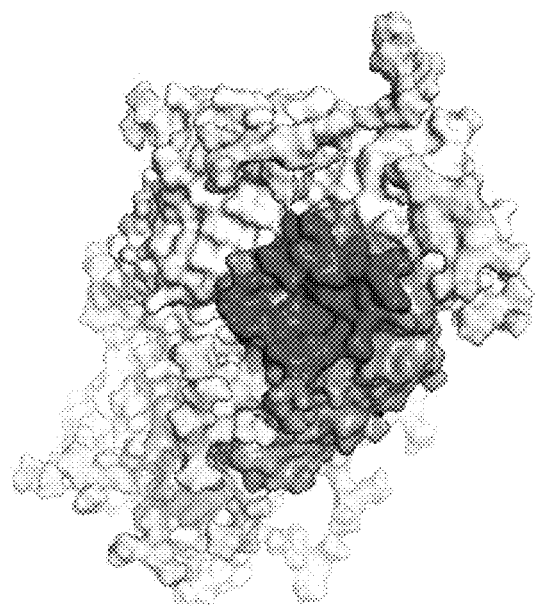
Figure 3A:
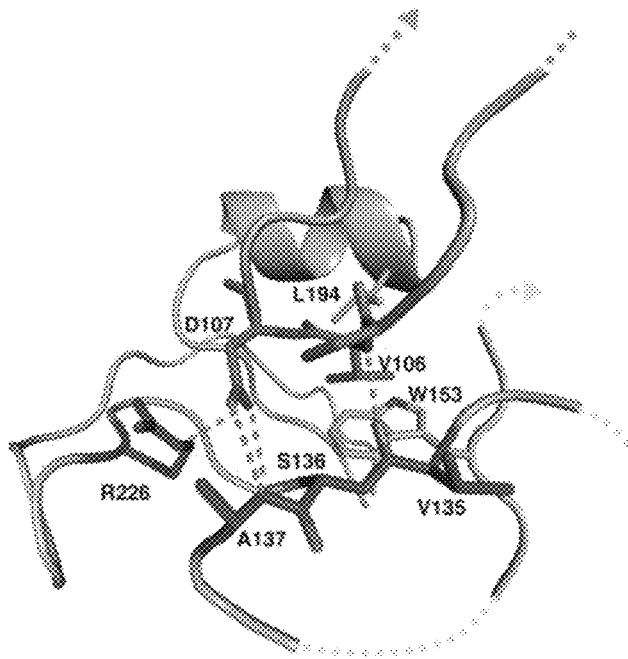
FIG. 3. Comparison of interactions from CH65 (A) and α-2,6-sialyl lactose (B).
Figure 3B:
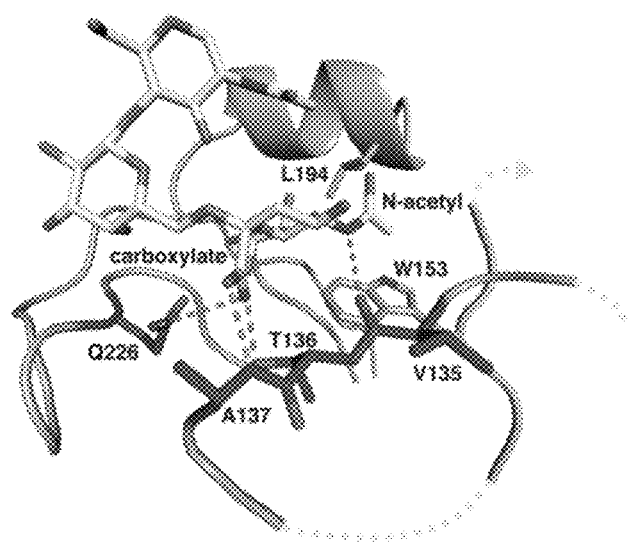
Figure 4:
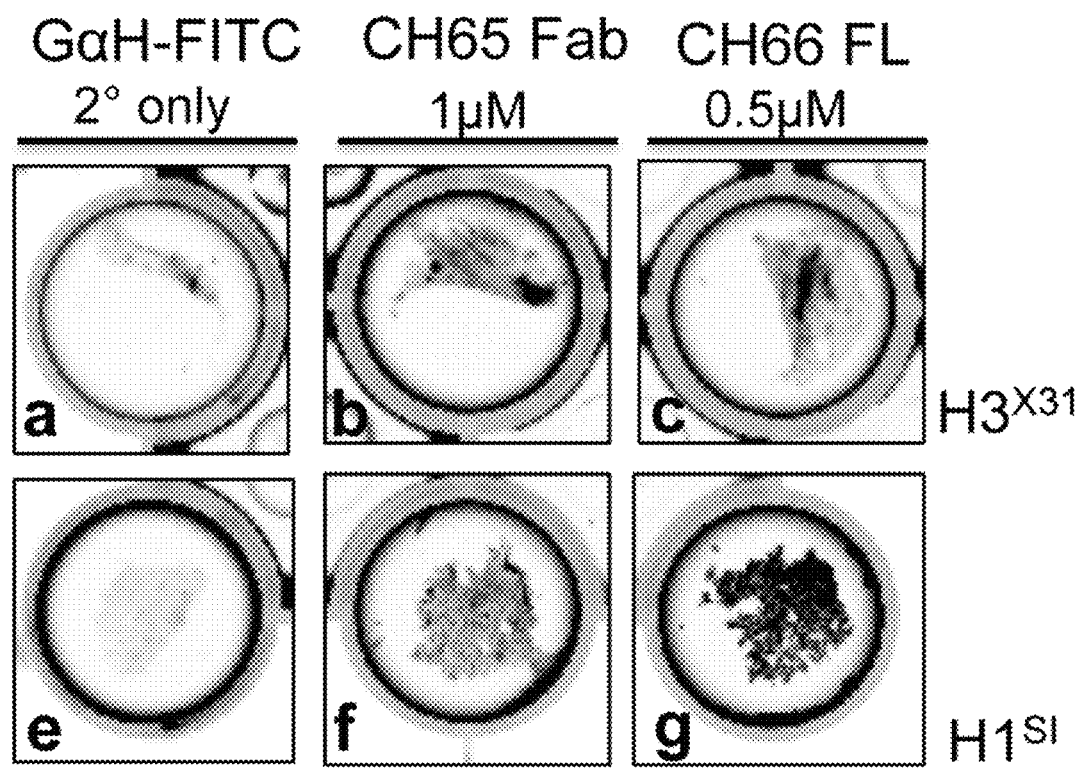
FIG. 4. Enzyme-linked immunoabsorbent assay (ELISA) of reactivity of CH65-CH67 lineage members to H1 and H3 influenza strains. 293 T cells were transfected with full-length HA from strain X31 (H3) (top panel, A-C) or with cell-surface expressed globular head from A/Solomon Islands/3/2006 [H1] (bottom panel, E-G). Cells were fixed with formaldehyde and probed with CH65 Fab (b and f) or CH66 full-length antibody (C and G), followed by a FITC-conjugated secondary antibody specific for the human Fab. Cells were imaged by FITC emission (532 nm). As a control, transfected cells were probed with secondary antibody only (A and E).

Rearranged Ig $V_H$ and $V_L$ genes were isolated by RT/PCR from peripheral blood mononuclear cells, collected from a subject one week after vaccination with the 2007 trivalent inactivated vaccine (TIV) (Liao, H. X. et al. *J. Virol. Methods* 158:171-179 (2009)). Among the clonal lineages detected by sequencing the rearranged genes was the three-member clone (mAbs CH65, CH66 and CH67) shown in FIG. 1A. The inferred sequence of the unmutated common ancestor (UCA) of the clonal lineage of antibodies CH65, CH66 and CH67 is unambiguous, except at position 99 of the heavy chain, which might be either glycine or alanine. FIG. 1B shows an alignment of the amino acid sequences of each antibody to the UCA. All three mature antibodies bind the H1 hemagglutinin (HA) present in the vaccine (A/Solomon Islands/3/2006) with about equal affinity; the UCA binds much more weakly.

Example 2

Breadth of Neutralizing Activity

The heavy chain of CH65 differs from the UCA at 12 positions in the variable domain; and at 6 positions its light chain. CH65 IgG1 and its Fab were expressed in 293T cells by transient transfection and purified as described below. Neutralization was tested against a large panel of H1 isolates from the past 30 years, including vaccine strains from 1977, 1991 and 1995, and observed strikingly broad potency (Table 1). CH67 was also tested against a subset of this panel (Table 1).

TABLE 1

Broad neutralization of seasonal influenza strains A/H1N1 by human MAb CH65 and CH67

| H1N1 virus strain | mAb minimum effective concentration (ug/ml) | |
|---|---|---|
| | CH65 | CH67 |
| A/USSR/90/1977* | 100 | 25 |
| A/Kawasaki/6/1986 | 0.098 | 0.39 |
| A/Texas/36/1991* | Neg | Neg |
| A/Wellington/47/1992 | Neg | Neg |
| A/Florida/2/1993 | 0.012 | 0.012 |
| A/Beijing/262/1995* | 0.098 | 0.098 |
| A/Shengzhen/227/1995 | 0.012 | 0.024 |
| A/Shanghai/8/1996 | Neg | Neg |
| A/Johannesburg/159/1997 | 0.098 | 0.39 |
| A/Shanghai/2/1997 | 0.195 | 0.195 |
| A/Moscow/13/1998 | 0.012 | 0.012 |
| A/Ostrava/801/1998 | 12.5 | Neg |
| A/New Caledonia/22/1999* | 0.391 | 0.195 |
| A/Bangkok/163/2000 | 0.195 | 0.098 |
| A/Fujian/156/2000 | 0.488 | 0.049 |
| A/Chile/8885/2001 | 0.195 | 0.098 |
| A/Auckland/65/2001 | 0.195 | 0.098 |
| A/Neimenggu/52/2002# | 0.098 | 0.098 |
| A/Brazil/1403/2003 | 3.125 | 0.195 |
| A/Canada/59/2004 | 0.098 | 0.098 |
| A/Solomon islands/03/2006*,+ | 0.024 | 0.098 |
| A/Brisbane/59/2007* | 0.098 | 0.98 |
| A/California/07/2009 (swine)* | Neg | 6.25 |

*Strains that were included in seasonal vaccines.
+H1 component of the vaccine received by the subject.
Originally reported as insensitive to mAb CH65.

The antibody neutralized H1N1 strains isolated as early as 1986, covering 21 years of antigenic drift. As expected, it neutralized A/Solomon Islands/3/2006, the H1 component of the 2007 vaccine. Of the 36 strains tested, it failed to neutralize only six, including the 2009 pandemic strain, A/Texas/36/1991 and A/USSR/90/1977. The CH67 antibody has a similar breadth; it also neutralizes (weakly) the 2009 pandemic strain. There is also evidence that CH66 (and likely CH65) binds HA from an H3 virus (X31, a lab strain derived from the 1968 pandemic. Too few HA-directed human monoclonal antibodies have been characterized for systematic comparison, but neutralization by serum samples does not ordinarily exhibit this degree of breadth.

Example 3

Structure of CH65:HA

A complex of the mAb CH65 Fab with the HA ectodomain from A/Solomon Islands/03/2006 ($HA^{ST}$) was crystallized, recorded diffraction to a minimum Bragg spacing of 3.2-Å (Table 2), and the structure was determined by molecular replacement as outlined below.

TABLE 2

Crystallographic statistics

Data collection

| | |
|---|---|
| Resolution (last shell), Å | 30.0-3.20 (3.31-3.20) |
| Wavelength, Å | 0.980 |
| Space group | I212121 |

TABLE 2-continued

Crystallographic statistics

| | |
|---|---|
| Unit cell dimensions (a, b, c), Å | 155.0, 191.8, 332.1 |
| Unit cell angles (α, β, γ), ° | 90, 90, 90 |
| I/σ (last shell) | 16.7 (2.1) |
| Rsym (last shell), % | 9.8 (63.7) |
| Completeness (last shell), % | 98.9 (94.4) |
| Number of refections | 368947 |
| unique | 80377 |
| Redundancy | 4.6 |
| Refinement | |
| Resolution, Å | 30.0-3.20 |
| Number of refections | 80336 |
| working | 78354 |
| free | 1982 |
| Rwork, % | 21.1 |
| Rfree, % | 24.8 |
| Ramachandran plot, % (favored/additional/disallowed) | 88.5/9.3/2.2 |
| Number of atoms: | |
| protein | 21794 |
| other (sulfate ions) | 214 |
| rmsd bond lengths, Å | 0.010 |
| rmsd bond angles, ° | 1.287 |

The asymmetric unit of the crystal contains a single copy of the HA trimer, with three bound Fabs (FIGS. 2A-2D). The final model includes all HA1 and HA2 residues in the expressed protein, except four disordered residues at the C-terminus of HA1. The electron density maps showed evidence for N-linked glycosylation at all eight potential sites on each monomer, and one or more sugar residues at five of these positions could be modeled. The Fab is well-ordered, except residue 1 of the light chain and residues 141-147 of the heavy chain; these residues are all far from the binding site.

A/Solomon Islands/03/2006 (this work) and A/Puerto Rico/8/1934 (Gamblin, S. J. et al., Science 303:1838-1842 (2004)) are, to the inventors' knowledge, the only seasonal H1N1 strains for which a structure of the HA has been determined; others are either pandemic strains or animal influenza strains. Comparison, using the program DALI, shows that HA$^{SI}$ is similar to other H1N1 HAs, such as those of the pandemic isolates from 2009 (Cα RMSD 0.9 Å over 495 aligned residues, 79% sequence identity; PDB IDs 3LZG (Xu, R. et al., *Science* 328:357-360 (2010)) and 3LYJ (Zhang, W. et al., *Protein Cell* 1:459-467 (2010))) and 1918 (Cα RMSD 1.5 Å over 495 aligned residues, 85% sequence identity; PDB IDs 3LZF (Xu, R. et al., *Science* 328:357-360 (2010)) and 1RUZ (Gamblin, S. J. et al., *Science* 303:1838-1842 (2004))) and the seasonal isolate from 1934 (Cα RMSD 1.5 Å over 482 aligned residues, 86% sequence identity; PDB ID 1RVZ (Gamblin, S. J. et al., *Science* 303:1838-1842 (2004))). The vestigial esterase domain of $HA^{SI}$ resembles that of the 2009 HA more closely than it does those from the 1918 and 1934 HAs.

MAb CH65 binds the globular head of the HA trimer (FIGS. 1C and 2A). The epitope includes both the receptor site and the antigenic site designated Sb in an early analysis of H1 sequences (Caton, A. J. et al., *Cell* 31:417-427 (1982)). The contact buries 858 $Å^2$ on the antibody and 748 $Å^2$ on HA1. All three CDRs of the heavy chain, as well as CDR-L1 and L3 of the light chain, participate in the interface (FIGS. 1C and 2B-D). CDR-H3 inserts into the receptor site. Seven of its nineteen residues contribute 402 $Å^2$ of buried surface area, or 47% of the complete interface. The other CDRs form flanking interactions. CDR-L3 contacts the N-terminal end of the short α-helix, site Sb, at the edge of the receptor pocket, and CDR-H1 and -H2 contact a loop that protrudes from HA1 adjacent to the C-terminus of the short α-helix.

Tables 3 and 4 summarize several of the critical interactions between the antibody and HA.

TABLE 3

| Residues in CDR H3 of CH65 that contact HA (Table discloses residues 104-107 of SEQ ID NO: 10) |
|---|
| Arg104* |
| Ser105 |
| Val106 |
| Asp107 |
| Tyr109 |
| Tyr 110 |
| Tyr 112 |

*for some influenza strains (not Solomon Islands), Arg104 might contact HA

TABLE 4

| Residues in HA that contact CH65 | |
|---|---|
| CDR | HA residue contacted |
| CDR H1 | 158 |
| CDR H2 | 158-160 |
| CDR H3 | 135-136; 190-195; 226 |
| CDR L1 | 222; 225; 227 |
| CDR L2 | (none) |
| CDR L3 | 187; 189 |

Example 4

CDR-H3 of mAb CH65 Compared to the Receptor

Because CDR-H3 inserts into the receptor site, this structure was compared to that of the human receptor analog LSTc (sialic-acid-α2,6-galactose-β1,4-N-acteylglucosamine) bound to 1934 HA (PDB ID 1RVZ: reference (Gamblin, S. J. et al., *Science* 303:1838-1842 (2004))) (FIGS. 3A and 3B). In CH65, Asp107 at the tip of CDR-H3 accepts hydrogen bonds from the backbone amide of HA1 Ala137, the side chain hydroxyl of Ser136, and the side chain Nϵ of Arg226. (Arginine is found only rarely at position 226: glutamine is more common Arg226 adopts a kinked conformation in the crystal structure; a glutamine would fit readily, with its Nϵ in the same position as the corresponding atom of the arginine side chain.) The backbone amide of Val106 in the antibody donates a hydrogen bond to the carboxyl oxygen of HA1 Val135 on HA1, and the nonpolar side chain of Val106 is in van der Waals contact with HA1 Trp153 and Leu194. In receptor analog LSTc, the carboxylate group of sialic acid has the same contacts with HA1 as does the (chemically analogous) side chain of Asp107, and the N-acetyl group interacts with HA in the same way as just described for the amide and side chain of Val106. In short, mAb CH65 mimics most of the chemical groups on the human receptor that interact with HA.

Example 5

Glycosylation

Glycosylation at antigenic sites is an important mechanism of immune evasion by influenza virus (Knossow, M. and Skehel, J. J. *Immunology* 119:1-7 (2006); Wiley, D. C.

and Skehel, J. J. Annu. Rev. Biochem. 56:365-394 (1987); and Wei, C. J. et al., *Sci. Transl. Med.* 2:24ra21 (2010)). In $HA^{SI}$, glycosylation leaves sites Sb and Cb exposed, partially obscures site Ca, and entirely masks antigenic site Sa. Site Sa is the epitope recognized by antibody 2D1, the prototype for Ig-mediated immunity to 2009 H1N1 in survivors of the 1918 epidemic (Xu, R. et al., *Science* 328:357-360 (2010)). Of the side chains in contact with 2D1, 7/16 differ between $HA^{SI}$ and 1918 HA; in comparison, only 3/16 differ between 2009 pandemic HA and 1918 HA. Because the HA of A/Solomon Islands/03/2006 is glycosylated at site Sa, neither vaccination with TIV-2007, nor prior infection with an A/Solomon Islands/03/2006-like strain could have elicited a 2D1-like immune response.

Example 6

Affinity Maturation

The amino-acid sequence of CH65 is the result of affinity maturation from its UCA. Analysis of the structure in light of its clonal lineage (FIG. 1B) shows that the central interactions of the antibodies with HA have remained unchanged by affinity maturation. The CDR-H3 has not mutated, nor has the contact of the light-chain CDR-L3 with the N-terminal end of the short α-helix, site Sb. (Ser93 of CDR-L3 is Asp in lineage member CH67; substitution to Asp may allow CH67 to accept a hydrogen-bond from HA Asn187.) Elsewhere on the interaction surface of the antibody, changes to two residues create additional hydrogen bonds between the antibody and $HA^{SI}$. Light-chain residues Asp26 and Arg29 in CDR-L1 have mutated from their respective germline counterparts, Asn and Ser. Asp26 accepts a hydrogen-bond from HA Lys222. Arg29 is positioned to donate two hydrogen-bonds to HA Asp225. Other changes, including those at position 31 (Gly to Asp) and positions 33-35 (Trp-Met-His to His-Ile-Asn) may exert subtle effects on the conformation of CDR-H3.

a FITC-conjugated secondary antibody specific for the human Fab. Cells were imaged by FITC emission (532 nm). As a control, transfected cells were probed with secondary antibody only (FIGS. 4A and 4E). These results indicate that the CH65-CH67 antibodies (e.g., CH66) also bind other influenza serotypes (e.g., H3).

As discussed in detail in the above examples, CH65 comes from an adult subject in the US, who received the 2007 TIV one week before donating a plasma sample. It was assumed that the subject had been exposed to H1N1 influenza strains in the past, so that the antibodies obtained by screening with a panel of recombinant hemagglutinins (rHAs) were from a secondary response. Indeed, the number of mutations (overall frequency about 5%) is too great to have occurred within just one week of a primary exposure. In the setting of TIV, a large fraction of the circulating antibody secreting plasma cells one week post vaccination are influenza specific (Wrammert, J. et al., *Nature* 453:667-671 (2008)). Unlike other methods (e.g., phage display) for high-throughput analysis of human B-cell responses, the procedure described herein to isolate CH65 detects paired rearranged $V_H$ and $V_L$ regions, and hence reconstructs the complete antigen combining site of the native antibody (Liao, H. X. et al. J. Virol. Methods 158:171-179 (2009)).

The CH65 antibody belongs to a relatively small clonal lineage of detected sequences, but there were presumably other members not represented among the expressed antibodies. Because the plasma cell from which it came probably derived from a vaccine-stimulated memory cell, most of the mutations that separate it from the UA probably occurred during the earlier primary response. The breadth of infectivity neutralization by CH65 implies that it might have arisen during nearly any of the seasonal outbreaks of the two decades preceding 2007, as only a small number of mutations during the secondary response could have produced a very tightly binding antibody from one of somewhat lower affinity.

The antigen combining site of CH65 has no markedly atypical structural features. It has contributions from $V_H$ 1~2, $D_H$ 1~1, and $J_H$ 6 and from Vκ3-~21 and Jκ2 (Table 5).

TABLE 5

Gene usage in CH65

| VH | | | | | | | VL | | | | |
|---|---|---|---|---|---|---|---|---|---|---|---|
| ID | V | D | J | Mutation frequency | CDR3 length No. of a.a | Isotype | ID | V | J | Mutation frequency | CDR3 length No. of a.a |
| H0082 | 1~2 | 1~1 | 6 | 5.0% | 19 | G1 | L0024 | 3~21 | 2 | 4.2% | 11 |
| H1226 | 1~2 | 1~1 | 6 | 4.8% | 19 | G1 | L0408 | 3~21 | 2 | 4.3% | 11 |
| H2250 | 1~2 | 1~1 | 6 | 4.7% | 19 | G1 | L0797 | 3~21 | 2 | 3.3% | 11 |

Example 7

CH65-CH67 Lineage Reactivity to Different Influenza Strains

The ability of CH65-CH67 to react with other influenza strains was assessed. 293 T cells were transfected with full-length HA from strain X31 (H3 influenza strain) (FIGS. 4A-4C, top panel) or with cell-surface expressed globular head from A/Solomon Islands/3/2006 (H1 influenza strain) (FIGS. 4E-4G, bottom panel). Cells were fixed with formaldehyde and probed with CH65 Fab (FIGS. 4B and 4F) or CH66 full-length antibody (FIGS. 4C and 4G), followed by The 19-residue heavy-chain CDR3 is of roughly average length (Volpe, J. M. and Kepler, T. B., *Immunome Res.* 4:3 (2008)). Its sequence in the mature antibody is the same as in the UCA. The VDJ recombination that gave rise to the coding sequence of the UCA included 17 n-nucleotides (FIG. 5), so that six of the fourteen CDR3 residues are encoded by the random insertions produced by imprecise joining. These six residues include Val106 and Asp107, which together make the most critical contacts within the sialic-acid pocket. The predicted n-nucleotide additions are somewhat fewer than average at the V-D junction and somewhat greater than average at the D-J junction (Volpe, J. M. and Kepler, T. B., *Immunome Res.* 4:3 (2008)).

The tip of the CH65 heavy-chain CDR3 is a strikingly faithful mimic of the sialic-acid surface that contacts HA. Early work on influenza virus antigenic variation led to discussion of an apparent conflict between escape from neutralization and conservation of an exposed receptor binding site. The HA structure resolved the issue, by showing that the sialic-acid binding site is smaller than the footprint of a typical antibody and hence that mutations in the periphery of the receptor pocket can interfere with neutralization without blocking receptor attachment (Wiley, D. C. et al., *Nature* 289:373-378 (1981); and Wilson, I. A. et al., *Nature* 289:366-373 (1981)). Indeed, variations affecting the susceptibility to neutralization by Ab CH65 map to sites that flank the receptor pocket but avoid any direct receptor contacts.

Two published structures of murine mAbs bound with H3 HAs show some degree of penetration into the receptor site—in both cases, by the heavy-chain CDR3. Neither mAb mimics the sialic-acid interaction as extensively as does CH65. In one (PDB ID 1KEN (Barbey-Martin, C. et al., *Virology* 294:70-74 (2002))), an aspartic acid side chain approaches the location of the sialic-acid carboxylate, but in an orientation that can accept a hydrogen bond only from the hydroxyl of Ser136 and not from the main-chain NH of Asn 137. In the other (2VIR (Fleury, D. et al., *Nat. Struct. Biol.* 5:119-123 (1998))), a Tyr-Asp pair at the tip of the CDR3 has an orientation related to that of the Val-Asp pair in our CH65:HA complex, and the aspartic acid side chain has the same hydrogen-bonding pattern, but the mimicry does not extend to any of the interactions of the receptor N-acetyl group. H3 HAs have leucine, rather than glutamine or arginine at position 226, so that additional polar contact is not available.

Sites of mutations in naturally occurring, seasonal antigenic variants of HA are largely on the outward facing surface of HA1. Some relatively rare antibodies that bind a conserved site along the "stem" of the HA have come from phage-displayed libraries of unrelated, rearranged human $V_H$ genes (all from $V_H1$-69). The structure and characteristics of CH65 show that it is also possible to elicit broadly neutralizing, receptor-binding site antibodies. A parallel can be drawn with the broadly neutralizing, receptor-site antibodies against HIV-1 (e.g., antibody VRC01), which are reasonably close mimics of the functional receptor, CD4 (Zhou T. et al., *Science* 329:811-817 (2010)).

An immunogen with an enhanced probability of eliciting a CH65-like response may protect against series of seasonal strains. A strategy for designing such an immunogen, based on analysis of both the structure and the lineage, could include (in addition to the native HA) a component to induce a UCA-like primary response. Inspection of the differences between CH65 and its UCA suggests that the principal changes affecting affinity are in the light-chain CDR1, where mutations at positions 26 and 29 have introduced salt bridges with HA (Table 6).

TABLE 6

Potential influence of residues in CH65 that have changed from UCA

| CH65 | UCA | potential effect |
|---|---|---|
| Heavy chain ||||
| E1 | Q | distant from contact |
| D31 | G | near a contact, but no salt bridge or strong polar H-bond |

TABLE 6-continued

Potential influence of residues in CH65 that have changed from UCA

| CH65 | UCA | potential effect |
|---|---|---|
| H33 | Y | no obvious likely perturbation |
| I34 | M | " |
| N35 | H | " |
| H52 | N | might compensate for Y->H at 33 |
| D57 | G | no obvious likely perturbation |
| A75 | S | distant |
| V83 | L | " |
| N84 | S | " |
| G85 | R | " |
| K87 | R | " |
| Light chain ||||
| D26 | N | adds salt bridge |
| R29 | S | adds salt bridge |
| N35 | Y | might affect hc:lc interface |
| C48 | Y | changes at 48 and 49 would compensate for ech other |
| Y49 | D | " |
| I98 | V | distant |

A modified HA, in which the same contacts instead gain stability from mutations in the antigen, might have the desired properties.

The lack of common resistance mutations among the many strains tested suggests that Ab CH65 will be a useful template for a therapeutic antibody. Oseltamivir-resistant H1N1, which emerged rapidly beginning in 2007-8, has become the predominant strain of seasonal influenza, and management of severe infection could benefit from a broadly reacting, immune-based therapeutic (Dharan, N. J. et al. *JAMA* 301:1034-1041 (2009)). Previous studies with a human mAb targeting the globular head of H5N1 indicate that the effective neutralizing concentrations for CH65 will be protective in vivo (Simmons, C. P. et al. *PLoS Med.* 4:e178 (2007)).

Accordingly, described herein are novel influenza HA antibodies that will be extremely effective in treating and preventing influenza infection. As seasonal antigenic drift of circulating influenza virus leads to a requirement for frequent changes in vaccine composition, because exposure or vaccination elicits human antibodies with limited cross-neutralization of drifted strains, there is a significant unmet need for an effective therapy that can broadly neutralize influenza drifted strains. The above results clearly demonstrate that use of the novel antibodies provides a solution to this unmet need. Therapy with the novel antibodies described herein is therefore a significant advance in the treatment of patients suffering from influenza infection.

The results reported herein were obtained using the following methods and materials.

Clinical Sample

MAbs CH65, CH66 and CH67 were obtained from a subject vaccinated with the 2007 TIV under a Duke Institutional Board approved human subjects protocol. The subject received the 2007-2008 Fluzone® (Sanofi Pasteur, Swiftwater, Pa.), which contained A/Solomon Islands/3/2006(H1N1), A/Wisconsin/67/2005(H3N2), and B/Malaysia/2506/2004. Blood was drawn on day 7 post-vaccination, and PBMC were isolated and cryopreserved on the same day. Single plasmablasts were sorted into 96-well plates, using a panel of antibodies as described (Moody M A, et al., *PLoS One* 6:e25797 (2011)). Single-cell RT/PCR was carried out to obtain DNA for sequencing (Liao, H. X. et al. *J. Virol. Methods* 158:171-179 (2009)), which was done in both forward and reverse directions using a BigDye® sequencing kit on an ABI 3700 (Ewing, B. et al., *Genome*

Res. 8:175-185 (1998)) and assembled with a method based on quality scores at each position (Kepler, T. B. et al. *BMC Genomics* 11:444 (2010)). Ig isotype was determined by local alignment with known sequences; V, D, and J region genes, CDR3 loop lengths, and mutation frequencies were determined by comparison with the inferred unmutated ancestor.

Lineage Analysis

The UCA was inferred using a Bayesian method by first determining the clonal tree by maximum likelihood using DNAML (Felsenstein, J. *J. Mol. Evol.* 17:368-376 (1981)), and then computing the posterior joint distribution on gene segments and recombination sites, conditional on the inferred ML tree. The posterior probability mass function on nucleotides at each position was then obtained directly.

Expression and Purification of IgG and Fab

The variable regions of immunoglobulin heavy- and light-chain genes were isolated by RT/PCR from single plasma cells as described above (Liao, H.X. et al. *J. Virol. Methods* 158:171-179 (2009)). For production of purified full-length IgG antibody, the $V_H$ and Vκ genes of CH65, CH66 and CH67 were cloned into a pcDNA 3.1 expression vector containing either the human IgG1 constant region gene or the κ-chain constant region gene (Liao, H.X. et al. *J. Virol. Methods* 158:171-179 (2009)). To produce the CH65 Fab, a 5' primer, HV13274-F1 (5'-AAGCTTACCATGC-CGATGGGCTCC-3' (SEQ ID NO: 47)), was designed to contain a restriction site (Hind III) and sequences to anneal to the 5' sequences of the Ig signal peptide, and a 3' primer, HV13221H-R474 (5'-GAGCCCAAATCTTGTGACAAAT-GATCTAGA-3' (SEQ ID NO: 48)) was designed to contain a restriction site (XbaI) and to introduce a stop codon after the sequence (5'TCTTGTGACAAA3' (SEQ ID NO: 49)), encoding amino acid residues, SCDK (SEQ ID NO: 50), just before the hinge of the human IgG1 constant region. PCR amplification, using these primers and the full-length IgG1 heavy chain gene as template, yielded the Fab gene, which was cloned into pcDNA3.1/hygro (Nicely, N.I. et al., *Nat. Struct. Mol. Biol.* 17:1492-1494 (2010)). Recombinant, intact, CH65 IgG1 and its Fab were produced in 293T cells by co-transfection with the genes encoding heavy and light chains. The intact antibody was purified using anti-human IgG beads (Sigma, St. Louis, Mo.); the Fab, using anti-L chain beads (Sigma, St. Louis, Mo.) followed by FPLC gel filtration (Liao, H.X. et al. *J. Virol. Methods* 158:171-179 (2009); and Nicely, N.I. et al., *Nat. Struct. Mol. Biol.* 17:1492-1494 (2010)).

Infectivity Neutralization

Infectivity neutralization was analyzed in a microneutralization assay based on the methods of the influenza reference laboratories at the Centers for Disease Control and Prevention (CDC) (Hancock, K. et al., *N. Engl. J. Med.* 361:1945-1952 (2009)). H1N1 historical virus stocks were provided by Vladimir Lugovtsev (Div. of Viral Products, CBER, FDA). All viruses were titrated on MDCK cells and used at 100 TCID$_{50}$ per well (in triplicate). Two-fold serial dilutions of mAb CH65, starting at 100 µg/ml, were mixed with virus stocks before addition to MDCK cell monolayers. The minimum concentrations that completely inhibited virus replication (EC99) are reported in Table 1.

HA Expression and Purification

Codon-optimized cDNA of the ectodomain of HA A/Solomon Islands/03/2006 was synthesized by GeneArt and subcloned into a pET vector modified for ligation-independent cloning (LIC). The synthetic gene encoded a secretion signal at the N terminus, and, in place of the transmembrane domain, a thrombin cleavage site, a T4-fibritin "foldon" to promote proper trimerization, and a His6 tag (SEQ ID NO: 46) at the C terminus. Trichoplusia ni (Hi-5) cells were infected with recombinant baculovirus. The supernatant was harvested at 48 hours post-infection by centrifugation, concentrated and diafiltered against phosphate-buffered saline with 40 mM imidazole, and loaded onto Ni-NTA resin. The protein was eluted, dialyzed, and incubated overnight with TPCK-treated trypsin at 1:500 mass ratio to remove the trimerization and His6 tags (SEQ ID NO: 46) and to cleave the HA0 precursor peptide. The protein was further purified by gel filtration chromatography on Superdex 200 (GE Healthcare).

Crystallization

The CH65 Fab and the A/Solomon Islands/03/2006 HA were incubated in 4.5:1 molar ratio, and the resulting 3:1 complex was separated from excess Fab by gel filtration chromatography on Superdex 200 in 10 mM Hepes pH 7.5, 150 mM NaCl. The complex was concentrated to an absorbance of 10 at 280 nm (approximately 6 mg/mL). Crystals were grown in hanging drops over a reservoir containing 2.2 M ammonium sulfate, 100 mM Tris pH 7.5, and 5% PEG-400 at 18 degrees C. Crystallization was improved by microseeding. After 3-14 days, crystals were cryoprotected by adding reservoir solution supplemented with 15% glycerol to the drop, then harvested and flash cooled in liquid nitrogen.

Structure Determination and Refinement

Diffraction experiments were performed at beamline 24-ID-E at the Advanced Photon Source. A dataset at 3.2-Å resolution was collected from a single ~50×50×300 μm rod and processed using HKL2000 (Table 2). Molecular replacement (MR) calculations were performed with PHASER (McCoy, A. J. et al., *J. Appl. Crystallogr.* 40:658-674 (2007)), using 1934 H1 HA (PDB ID 1RVZ (Gamblin, S. J. et al., *Science* 303:1838-1842 (2004))) as the starting model. Initial phases from MR enabled a search for Fab molecules by phased molecular replacement in MOLREP, using a library of Fab structures. The model was refined in CNS (Brunger, A. T., *Nat. Protoc.* 2:2728-2733 (2007)) by simulated annealing using deformable elastic network restraints and rebuilt in COOT (Emsley, P. and Cowtan, K., *Acta Crystallogr. D. Biol. Crystallogr.* 60:2126-2132 (2004)). N-linked glycans from a high-resolution structure were fitted into experimental electron density maps where appropriate. Strong 3-fold non-crystallographic symmetry restraints were applied to HA and to each domain of the Fab throughout refinement, allowing variation in the angle between the conserved domain and the variable domain of the Fab. Finally, 3 cycles of individual positional and B-factor refinement in PHENIX (Adams, P. D. et al., *Acta Crystallogr. D. Biol. Crystallogr.* 58:1948-1954 (2002)) resulted in a model in good agreement with observed intensities (R/Rfree=21.1/24.8%) (Table 2). Coordinates and diffraction data have been submitted to the PDB, accession number 3SM5.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

INCORPORATION BY REFERENCE

All patents and publications mentioned in this specification are herein incorporated by reference to the same extent as if each independent patent and publication was specifically and individually indicated to be incorporated by reference.

What is claimed is:

1. An anti-influenza recombinant monoclonal antibody or antigen binding fragment thereof that specifically binds influenza hemagglutinin (HA) at residues 136, 137 and 226 of the HA polypeptide sequence and thereby reduces or inhibits influenza hemagglutinin binding to sialic acid, wherein the anti-influenza antibody or antigen binding fragment thereof comprises at least one sequence selected from the group consisting of:
   a variable heavy ($V_H$) chain sequence SEQ ID NO: 9, SEQ ID NO: 10, SEQ ID NO: 11, SEQ ID NO: 12, or one or more heavy chain CDR regions present in a variable heavy ($V_H$) chain amino acid sequence of SEQ ID NO: 9, SEQ ID NO: 10, SEQ ID NO: 11, or SEQ ID NO: 12; and
   a variable light ($V_L$) chain sequence SEQ ID NO: 13, SEQ ID NO: 14, SEQ ID NO: 15, SEQ ID NO: 16, or one or more light chain CDR regions present in a variable light ($V_L$) chain amino acid sequence of SEQ ID NO: 13, SEQ ID NO: 14, SEQ ID NO: 15, or SEQ ID NO: 16.

2. The anti-influenza recombinant monoclonal antibody or antigen binding fragment thereof of claim 1, wherein the anti-influenza antibody or antigen binding fragment thereof comprises i) a variable heavy ($V_H$) chain comprising SEQ ID NO: 10, and ii) a variable light ($V_L$) chain comprising SEQ ID NO: 14.

3. The anti-influenza recombinant monoclonal antibody or antigen binding fragment thereof of claim 1, wherein the one or more heavy chain CDR regions comprises a CDR3 region of SEQ ID NO: 9, SEQ ID NO: 10, SEQ ID NO: 11, or SEQ ID NO: 12.

4. The anti-influenza recombinant monoclonal antibody or antigen binding fragment thereof of claim 3, wherein the one or more light chain CDR regions comprises a CDR3 region of SEQ ID NO: 13, SEQ ID NO: 14, SEQ ID NO: 15, or SEQ ID NO: 16.

5. The anti-influenza recombinant monoclonal antibody or antigen binding fragment thereof of claim 1, wherein the anti-influenza recombinant monoclonal antibody or antigen binding fragment thereof comprises a variable heavy ($V_H$) chain, wherein the CDR3 region of the $V_H$ chain comprises Arg104, Ser105, Val106, Asp107, Tyr109, Tyr110, Tyr112, or a combination thereof.

6. The anti-influenza recombinant monoclonal antibody or antigen binding fragment thereof of claim 1, wherein the bound HA polypeptide sequence is SEQ ID NO: 17.

7. The anti-influenza recombinant monoclonal antibody or antigen binding fragment thereof of claim 1, wherein the antigen binding fragment thereof is an Fab fragment, an Fab' fragment, an Fd fragment, a Fd' fragment, an Fv fragment, a dAb fragment, an F(ab')₂ fragment, a single chain fragment, a diabody, or a linear antibody.

8. The anti-influenza recombinant monoclonal antibody or antigen binding fragment thereof of claim 1, further comprising an agent conjugated to the anti-influenza antibody or antigen binding fragment thereof.

9. The anti-influenza recombinant monoclonal antibody or antigen binding fragment thereof of claim 8, wherein the agent conjugated to the antibody or antigen binding fragment thereof is a therapeutic agent or detectable label.

10. The anti-influenza recombinant monoclonal antibody or antigen binding fragment thereof of claim 9, wherein the therapeutic agent is a small molecule, nanoparticle, polypeptide, radioisotope, or inhibitory nucleic acid.

11. The anti-influenza recombinant monoclonal antibody or antigen binding fragment thereof of claim 10, wherein the therapeutic agent is an antiviral agent or a toxin.

12. The anti-influenza recombinant monoclonal antibody or antigen binding fragment thereof of claim 10, wherein the therapeutic agent is an siRNA, shRNA, or antisense nucleic acid molecule that reduces influenza virus production.

13. The anti-influenza recombinant monoclonal antibody or antigen binding fragment thereof of claim 9, wherein the detectable label is detected by spectroscopic, photochemical, biochemical, immunochemical, physical, or chemical means.

14. The anti-influenza recombinant monoclonal antibody or antigen binding fragment thereof of claim 9, wherein the detectable label is an enzyme, a fluorescent molecule, a particle label, an electron-dense reagent, a radiolabel, a microbubble, biotin, digoxigenin, or a hapten or a protein that has been made detectable.

15. The anti-influenza recombinant monoclonal antibody or antigen binding fragment thereof of claim 1, wherein the influenza is H1N1, H2N2, H3N2, or a human adapted H5 strain.

16. The anti-influenza recombinant monoclonal antibody or antigen binding fragment thereof of claim 1 derivatized with a moiety that improves the solubility, the biological half-life or the absorption of the antibody or antigen binding fragment thereof.

17. The anti-influenza recombinant monoclonal antibody or antigen binding fragment thereof of claim 1, wherein the anti-influenza antibody or antigen binding fragment thereof comprises:

1 variable heavy ($V_H$) chain CDR1, CDR2 and CDR3 region seqeunces of SEQ ID NO: 9, SEQ ID NO: 10, SEQ ID NO: 11 or SEQ ID NO: 12; and variable light ($V_L$) chain CDR1, CDR2 and CDR3 region sequences of SEQ ID NO: 13, SEQ ID NO: 14, SEQ ID NO: 15 or SEQ ID NO: 16.

18. A method of neutralizing an influenza virus or treating, preventing, inhibiting dissemination of or inhibiting establishment of an influenza virus infection in a subject in need thereof or inhibiting influenza virus entry into a cell, wherein the method comprises administering to the subject an effective amount of the anti-influenza antibody or antigen binding fragment thereof of claim 1, thereby neutralizing an influenza virus or treating, preventing, inhibiting dissemination of or inhibiting establishment of an influenza virus infection in the subject or inhibiting influenza virus entry into a cell of the subject.

19. The method of claim 18, wherein the influenza is H1N1, H2N2, H3N2, or a human adapted H5 strain.

20. The method of claim 18, wherein the subject has or is at risk of developing an influenza infection, optionally wherein the subject is a mammal, optionally a human, optionally wherein the subject is susceptible to viral infection, optionally wherein the subject is selected from the group consisting of a pregnant female, a young or infant subject and an elderly subject.

21. The method of claim 18, wherein the anti-influenza antibody or antigen binding fragment thereof is administered by intramuscular injection, intravenous injection, subcutaneous injection, or inhalation.

22. A method of inhibiting influenza virus entry into a cell, wherein the method comprises contacting a cell having or at risk of developing influenza virus infection with i) the anti-influenza antibody or antigen binding fragment thereof of claim 1, thereby inhibiting influenza virus entry into the cell.

* * * * *

SEQUENCE LISTING

<160> NUMBER OF SEQ ID NOS: 61

<210> SEQ ID NO 1
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tggtgcagtc tggggctgag gtgaagaagc tggggcctc agtgaaggtc      60 tcctgcaagg cttctggata caccttcacc ggctactata tgcactgggt gcgacaggcc    120
cctggacaag ggcttgagtg gatgggatgg atcaaccta acagtggtgg cacaaactat     180
gcacagaagt tcagggctg gtcaccatg accagggaca cgtccatcag cacagcctac     240
atggagctga gcaggctgag atctgacgac acggccgtgt attactgtgc gagaggggga   300
ctggaacccc gatctgtaga ctactactac tacggtatgg acgtctgggg ccaagggacc   360
acggtcaccg tctcctca                                                   378

<210> SEQ ID NO 2
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gaagtgcagc tggtgcagtc tggagctgag gtgaagaagc tggggcctc agtgaaagtc      60 tcctgcaagg cttctggata caccttcacc gactatcata taaactgggt gcgacaggcc    120
cctggacaag ggcttgagtg gatgggatgg atccacccta acagtggtga cacaaactat    180
gcacagaagt tcagggctg gtcaccatg accagggaca cggccatcag cacagcctac     240
atggaggtga atggcttgaa atctgacgac acggccgtgt attattgtgc gagagggga    300 ctggaacccc gatctgtaga ctactactat tatggtatgg acgtctgggg ccaagggacc   360
acggtcaccg tctcctca                                                   378

<210> SEQ ID NO 3
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
caggtgcagc tggtgcagtc tggggctgag gtgaagaagc tggggcctc agtgaaagtc      60 tcctgcaagg cttctggata caccttcacc gactatcata taaactgggt gcgacaggcc    120
cctggacaag ggcttgagtg gatgggatgg atccacccta acagtggtga cacaaactat    180
gcacagaagt tcagggctg gtcaccatg accagggaca cgtccatcag cacagcctac     240
atggaggtga atggcttgaa atctgacgac acggccgtgt attattgtgc gagagggga    300 ctggaacctc gatctgtaga ctactactat tatggtatgg acgtctgggg ccaagggacc   360
acggtcaccg tctcctca                                                   378

<210> SEQ ID NO 4

<210> SEQ ID NO 4
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
caggtgcagc tggtgcagtc tggggctgag gtgaggaagc ctggggcctc agtgaaggtc      60
tcctgcaagg cttctggata caccttcacc gacaactata tacactgggt gcgacaggcc     120
cctggacaag ggcttgagtg gatgggatgg atccacccta acagtggtgc cacaaagtat     180
gcacagaagt ttgagggctg gtcaccatg  accaggaca cgtcaatcag cacagtctac     240
atggaactga gcagatcgag atctgacgac acggccgtat attactgtgc gagagcggga     300
ctggaaccac gatccgtaga ctactacttc tacggtttgg acgtctgggg ccaagggacc     360
gcggtcaccg tctcctca                                                   378
```

<210> SEQ ID NO 5
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
cagtctgtgc tgactcagcc accctcggtg tcagtggccc caggacagac ggccaggatt      60
acctgtgggg gaaacaacat tggaagtaaa agtgtgcact ggtaccagca gaagccaggc     120
caggcccctg tgctggtcgt ctatgatgat agcgaccggc cctcagggat ccctgagcga     180
ttctctggct ccaactctgg gaacacggcc accctgacca tcagcagggt cgaagccggg     240
gatgaggccg actattactg tcaggtgtgg gatagtagta gtgatcatgt ggtattcggc     300
ggagggacca gctgaccgt ccta                                             324
```

<210> SEQ ID NO 6
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
cagtctgtgc tgactcagcc accctcggtg tcagtggccc cagggcagac ggccaggatt      60
acctgtgggg gaaatgatat tggaaggaag agtgtgcact ggaaccagca gaagccaggc     120
caggcccctg tgctggtcgt ctgttatgat agcgaccggc cctcagggat ccctgagcga     180
ttctctggct ccaattcagg gaacacggcc accctgacca tcagtagggt cgaagccggg     240
gatgaggccg actattattg tcaggtgtgg gatagtagta gtgatcatgt gatattcggc     300
ggagggacca gctgaccgt ccta                                             324
```

<210> SEQ ID NO 7
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
cagtctgccc tgactcagcc accctcggtg tcagtggccc cagggcagac ggccaggatt    60
acctgtgggg gaaatgatat tggaaggaag agtgtgcact ggaaccagca gaagccaggc   120
caggcccctg tgctggtcgt ctgttatgat agtgaccggc cctcagggat ccctgagcga   180
ttctctggct ccaattcagg gaacacggcc accctgacca tcagcagggt cgaagccggg   240
gatgaggccg actattattg tcaggtgtgg gatagtagta gtgatcatgt ggtattcggc   300
ggagggacca agctgaccgt ccta                                          324

<210> SEQ ID NO 8
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
cagtctgccc tgactcagcc accctcggtg tcagtggccc caggacagac ggccacgatt    60
acctgtgggg gaaacaacat tggacgtaaa agagtggact ggttccagca gaagccaggc   120
caggcccctg tgctggtcgt ctatgaggat agcgaccggc cctcagggat ccctgagcga   180
ttctctgact ccaactctgg gaccacggcc accctgacca tcagcagggt cgaagccggg   240
gatgaggccg actattactg tcaggtgtgg gatagtgata gtgatcatgt ggtattcggc   300
ggagggacca aactgaccgt ccta                                          324

<210> SEQ ID NO 9
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Leu Glu Pro Arg Ser Val Asp Tyr Tyr Tyr Tyr Gly
            100                 105                 110

Met Asp Val Trp Gly Gln Gly Thr Thr Val Thr Val Ser Ser
        115                 120                 125

<210> SEQ ID NO 10
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

His Ile Asn Trp Val Arg Gln Ala Pro Gly Gln Gly Leu Glu Trp Met
        35                  40                  45

Gly Trp Ile His Pro Asn Ser Gly Asp Thr Asn Tyr Ala Gln Lys Phe
    50                  55                  60

Gln Gly Trp Val Thr Met Thr Arg Asp Thr Ala Ile Ser Thr Ala Tyr
65                  70                  75                  80

Met Glu Val Asn Gly Leu Lys Ser Asp Asp Thr Ala Val Tyr Tyr Cys
                85                  90                  95

Ala Arg Gly Gly Leu Glu Pro Arg Ser Val Asp Tyr Tyr Tyr Tyr Gly
            100                 105                 110

Met Asp Val Trp Gly Gln Gly Thr Thr Val Thr Val Ser Ser
        115                 120                 125

<210> SEQ ID NO 11
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

His Ile Asn Trp Val Arg Gln Ala Pro Gly Gln Gly Leu Glu Trp Met
        35                  40                  45

Gly Trp Ile His Pro Asn Ser Gly Asp Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Val Asn Gly Leu Lys Ser Asp Asp Thr Ala Val Tyr Tyr Cys
                85                  90                  95

Ala Arg Gly Gly Leu Glu Pro Arg Ser Val Asp Tyr Tyr Tyr Tyr Gly
            100                 105                 110

Met Asp Val Trp Gly Gln Gly Thr Thr Val Thr Val Ser Ser
        115                 120                 125

<210> SEQ ID NO 12
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Asp Asn
            20                  25                  30

Tyr Ile His Trp Val Arg Gln Ala Pro Gly Gln Gly Leu Glu Trp Met
            35                  40                  45

Gly Trp Ile His Pro Asn Ser Gly Ala Thr Lys Tyr Ala Gln Lys Phe
 50                  55                  60

Glu Gly Trp Val Thr Met Thr Arg Asp Thr Ser Ile Ser Thr Val Tyr
65                  70                  75                  80

Met Glu Leu Ser Arg Ser Arg Ser Asp Thr Ala Val Tyr Tyr Cys
                85                  90                  95

Ala Arg Ala Gly Leu Glu Pro Arg Ser Val Asp Tyr Tyr Phe Tyr Gly
            100                 105                 110

Leu Asp Val Trp Gly Gln Gly Thr Ala Val Thr Val Ser Ser
            115                 120                 125

<210> SEQ ID NO 13
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Ser Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Ser Val Leu Thr Gln Pro Pro Ser Val Ser Val Ala Pro Gly Gln
1               5                   10                  15

Thr Ala Arg Ile Thr Cys Gly Gly Asn Asp Ile Gly Arg Lys Ser Val
            20                  25                  30

His Trp Asn Gln Gln Lys Pro Gly Gln Ala Pro Val Leu Val Val Cys
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

```
Val Ile Phe Gly Gly Gly Thr Lys Leu Thr Val Leu
            100                 105

<210> SEQ ID NO 15
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Ser Ala Leu Thr Gln Pro Pro Ser Val Ser Val Ala Pro Gly Gln
1               5                   10                  15

Thr Ala Arg Ile Thr Cys Gly Gly Asn Asp Ile Gly Arg Lys Ser Val
            20                  25                  30

His Trp Asn Gln Gln Lys Pro Gly Gln Ala Pro Val Leu Val Val Cys
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105

<210> SEQ ID NO 16
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Ser Ala Leu Thr Gln Pro Pro Ser Val Ser Val Ala Pro Gly Gln
1               5                   10                  15

Thr Ala Thr Ile Thr Cys Gly Gly Asn Asn Ile Gly Arg Lys Arg Val
            20                  25                  30

Asp Trp Phe Gln Gln Lys Pro Gly Gln Ala Pro Val Leu Val Val Tyr
        35                  40                  45

Glu Asp Ser Asp Arg Pro Ser Gly Ile Pro Glu Arg Phe Ser Asp Ser
    50                  55                  60

Asn Ser Gly Thr Thr Ala Thr Leu Thr Ile Ser Arg Val Glu Ala Gly
65                  70                  75                  80

Asp Glu Ala Asp Tyr Tyr Cys Gln Val Trp Asp Ser Asp Ser Asp His
                85                  90                  95

Val Val Phe Gly Gly Gly Thr Lys Leu Thr Val Leu
            100                 105

<210> SEQ ID NO 17
<211> LENGTH: 216
<212> TYPE: PRT
<213> ORGANISM: Influenza A virus

<400> SEQUENCE: 17

Ala Pro Leu Gln Leu Gly Asn Cys Ser Val Ala Gly Trp Ile Leu Gly
1               5                   10                  15

Asn Pro Glu Cys Glu Leu Leu Ile Ser Arg Glu Ser Trp Ser Tyr Ile
```

```
                    20                  25                  30
Val Glu Lys Pro Asn Pro Glu Asn Gly Thr Cys Tyr Pro Gly His Phe
                35                  40                  45
Ala Asp Tyr Glu Glu Leu Arg Glu Gln Leu Ser Ser Val Ser Ser Phe
            50                  55                  60
Glu Arg Phe Glu Ile Phe Pro Lys Glu Ser Ser Trp Pro Asn His Thr
65                  70                  75                  80
Thr Thr Gly Val Ser Ala Ser Cys Ser His Asn Gly Glu Ser Ser Phe
                85                  90                  95
Tyr Lys Asn Leu Leu Trp Leu Thr Gly Lys Asn Gly Leu Tyr Pro Asn
            100                 105                 110
Leu Ser Lys Ser Tyr Ala Asn Asn Lys Glu Lys Glu Val Leu Val Leu
            115                 120                 125
Trp Gly Val His His Pro Pro Asn Ile Gly Asp Gln Arg Ala Leu Tyr
            130                 135                 140
His Thr Glu Asn Ala Tyr Val Ser Val Val Ser Ser His Tyr Ser Arg
145                 150                 155                 160
Lys Phe Thr Pro Glu Ile Ala Lys Arg Pro Lys Val Arg Asp Arg Glu
                165                 170                 175
Gly Arg Ile Asn Tyr Tyr Trp Thr Leu Leu Glu Pro Gly Asp Thr Ile
            180                 185                 190
Ile Phe Glu Ala Asn Gly Asn Leu Ile Ala Pro Arg Tyr Ala Phe Ala
            195                 200                 205
Leu Ser Arg Gly Phe Gly Ser Gly
            210                 215

<210> SEQ ID NO 18
<211> LENGTH: 217
<212> TYPE: PRT
<213> ORGANISM: Influenza A virus

<400> SEQUENCE: 18

Ala Pro Leu Gln Leu Gly Asn Cys Ser Val Ala Gly Trp Ile Leu Gly
1               5                   10                  15
Asn Pro Glu Cys Glu Ser Leu Phe Ser Lys Glu Ser Trp Ser Tyr Ile
                20                  25                  30
Ala Glu Thr Pro Asn Pro Glu Asn Gly Thr Cys Tyr Pro Gly His Phe
                35                  40                  45
Ala Asp Tyr Glu Glu Leu Arg Glu Gln Leu Ser Ser Val Ser Ser Phe
            50                  55                  60
Glu Arg Phe Glu Ile Phe Pro Lys Glu Ser Ser Trp Pro Asn His Thr
65                  70                  75                  80
Val Thr L

Glu Gly Arg Ile Asn Tyr Tyr Trp Thr Leu Leu Glu Pro Gly Asp Thr
            180                 185                 190

Ile Ile Phe Glu Ala Asn Gly Asn Leu Ile Ala Pro Trp Tyr Ala Phe
        195                 200                 205

Ala Leu Ser Arg Gly Phe Gly Ser Gly
        210                 215

<210> SEQ ID NO 19
<211> LENGTH: 217
<212> TYPE: PRT
<213> ORGANISM: Influenza A virus

<400> SEQUENCE: 19

Ala Pro Leu Gln Leu Gly Asn Cys Ser Val Ala Gly Trp Ile Leu Gly
1               5                   10                  15

Asn Pro Glu Cys Glu Ser Leu Phe Ser Lys Glu Ser Trp Ser Tyr Ile
            20                  25                  30

Ala Glu Thr Pro Asn Pro Glu Asn Gly Thr Cys Tyr Pro Gly Tyr Phe
        35                  40                  45

Ala Asp Tyr Glu Glu Leu Arg Glu Gln Leu Ser Ser Val Ser Ser Phe
    50                  55                  60

Glu Arg Phe Glu Ile Phe Pro Lys Glu Ser Ser Trp Pro Lys His Thr
65                  70                  75                  80

Val Thr Lys Gly Val Thr Ala Ser Cys Ser His Asn Gly Lys Ser Ser
                85                  90                  95

Phe Tyr Lys Asn Leu Leu Trp Leu Thr Glu Lys Asn Gly Leu Tyr Pro
            100                 105                 110

Asn Leu Ser Lys Ser Tyr Val Asn Asn Lys Glu Lys Glu Val Leu Val
        115                 120                 125

Leu Trp Gly Val His His Pro Ser Asn Ile Gly Asp Gln Arg Ala Ile
    130                 135                 140

Tyr His Thr Glu Asn Ala Tyr Val Ser Val Val Ser Ser His Tyr Ser
145                 150                 155                 160

Arg Arg Phe Thr Pro Glu Ile Ala Lys Arg Pro Lys Val Arg Gly Gln
                165                 170                 175

Glu Gly Arg Ile Asn Tyr Tyr Trp Thr Leu Leu Glu Pro Gly Asp Thr
            180                 185                 190

Ile Ile Phe Glu Ala Asn Gly Asn Leu Ile Ala Pro Trp Tyr Ala Phe
        195                 200                 205

Ala Leu Ser Arg Gly Phe Gly Ser Gly
        210                 215

<210> SEQ ID NO 20
<211> LENGTH: 217
<212> TYPE: PRT
<213> ORGANISM: Influenza A virus

<400> SEQUENCE: 20

Ala Pro Leu Gln Leu Gly Asn Cys Ser Val Ala Gly Trp Ile

```
Glu Arg Phe Glu Ile Phe Pro Lys Glu Ser Ser Trp Pro Asn His Thr
 65                  70                  75                  80

Val Thr Lys Gly Val Thr Ala Ser Cys Ser His Asn Gly Lys Ser Ser
                 85                  90                  95

Phe Tyr Arg Asn Leu Leu Trp Leu Thr Glu Lys Asn Gly Leu Tyr Pro
            100                 105                 110

Asn Leu Ser Lys Ser Tyr Val Asn Asn Lys Glu Lys Glu Val Leu Val
        115                 120                 125

Leu Trp Gly Val His His Pro Ser Asn Met Gly Asp Gln Arg Ala Ile
130                 135                 140

Tyr His Thr Glu Asn Ala Tyr Val Ser Val Val Ser Ser His Tyr Ser
145                 150                 155                 160

Arg Arg Phe Thr Pro Glu Ile Ala Lys Arg Pro Lys Val Arg Asp Gln
                165                 170                 175

Glu Gly Arg Ile Asn Tyr Tyr Trp Thr Leu Leu Glu Pro Gly Asp Thr
            180                 185                 190

Ile Ile Phe Glu Ala Asn Gly Asn Leu Ile Ala Pro Arg Tyr Ala Phe
        195                 200                 205

Ala Leu Ser Arg Gly Phe Gly Ser Gly
210                 215

<210> SEQ ID NO 21
<211> LENGTH: 217
<212> TYPE: PRT
<213> ORGANISM: Influenza A virus

<400> SEQUENCE: 21

Ala Pro Leu Gln Leu Gly Asn Cys Ser Ile Ala Gly Trp Ile Leu Gly
  1               5                  10                  15

Asn Pro Glu Cys Glu Ser Leu Phe Ser Lys Ser Trp Ser Tyr Ile
             20                  25                  30

Ala Glu Thr Pro Asn Pro Glu Asn Gly Thr Cys Tyr Pro Gly Tyr Phe
         35                  40                  45

Ala Asp Tyr Glu Glu Leu Arg Glu Gln Leu Ser Ser Val Ser Ser Phe
 50                  55                  60

Glu Arg Phe Glu Ile Phe Pro Lys Glu Ser Ser Trp Pro Asn His Thr
 65                  70                  75                  80

Val Thr Lys Gly Val Thr Ala Ser Cys Ser His Asn Gly Lys Ser Ser
                 85                  90                  95

Phe Tyr Lys Asn Leu Leu Trp Leu Thr Glu Lys Asn Gly Leu Tyr Pro
            100                 105                 110

Asn Leu Ser Lys Ser Tyr Val Asn Asn Lys Lys Lys Glu Val Leu Val
        115                 120                 125

Leu Trp Gly Val His His Pro Ser Asn Ile Gly Asp Gln Arg Ala Ile
130                 135                 140

Tyr His Thr Glu Asn Ala Tyr Val Ser Val Val Ser Ser His Tyr Ser
145                 150                 155                 160

Arg Arg Phe Thr Pro Glu Ile Ala Lys Arg Pro Lys Val Arg Asn Gln
                165                 170                 175

Glu Gly Arg Ile Asn Tyr Tyr Trp Thr Leu Leu Glu Pro Gly Asp Thr
            180                 185                 190

Ile Ile Phe Glu Ala Asn Gly Asn Leu Ile Ala Pro Trp Tyr Ala Phe
        195                 200                 205

Ala Leu Ser Arg Gly Phe Glu Ser Gly
210                 215
```

<210> SEQ ID NO 22
<211> LENGTH: 216
<212> TYPE: PRT
<213> ORGANISM: Influenza A virus

<400> SEQUENCE: 22

Ala Pro Leu Gln Leu Gly Asn Cys Ser Val Ala Gly Trp Ile Leu Gly
1               5                   10                  15

Asn Pro Glu Cys Glu Ser Leu Ile Phe Lys Glu Ser Trp Ser Tyr Ile
            20                  25                  30

Val Glu Thr Pro Asn Pro Glu Asn Gly Thr Cys Tyr Pro Gly Tyr Phe
        35                  40                  45

Ala Asp Tyr Glu Glu Leu Arg Glu Gln Leu Ser Ser Val Ser Ser Phe
    50                  55                  60

Glu Arg Phe Glu Ile Phe Pro Lys Glu Ser Ser Trp Pro Asn His Thr
65                  70                  75                  80

Val Thr Gly Val Ser Ala Ser Cys Ser His Asn Gly Lys Ser Ser Phe
                85                  90                  95

Tyr Arg Asn Leu Leu Trp Leu Thr Glu Lys Asn Gly Leu Tyr Pro Asn
            100                 105                 110

Leu Ser Lys Ser Tyr Val Asn Asn Lys Glu Lys Glu Val Leu Val Leu
        115                 120                 125

Trp Gly Val His His Pro Ser Asn Ile Arg Asp Gln Arg Ala Ile Tyr
    130                 135                 140

His Thr Glu Asn Ala Tyr Val Ser Val Ser Ser His Tyr Ser Arg
145                 150                 155                 160

Arg Phe Thr Pro Glu Ile Ala Lys Arg Pro Lys Val Arg Gly Gln Glu
                165                 170                 175

Gly Arg Ile Asn Tyr Tyr Trp Thr Leu Leu Glu Pro Gly Asp Thr Ile
            180                 185                 190

Ile Phe Glu Ala Asn Gly Asn Leu Ile Ala Pro Trp Tyr Ala Phe Ala
        195                 200                 205

Leu Ser Arg Gly Phe Gly Ser Gly
    210                 215

<210> SEQ ID NO 23
<211> LENGTH: 216
<212> TYPE: PRT
<213> ORGANISM: Influenza A virus

<400> SEQUENCE: 23

Ala Pro Leu Gln Leu Gly Asn Cys Ser Val Ala Gly Trp Ile Leu Gly
1               5                   10                  15

Asn Pro Glu Cys Glu Leu Leu Ile Ser Lys Glu Ser Trp Ser Tyr Ile
            20                  25                  30

Val Glu Lys Pro Asn Pro Glu Asn Gly Thr Cys Tyr Pro Gly His Phe
        35                  40                  45

Ala Asp Tyr Glu Glu Leu Arg Glu Gln Leu Ser Ser Val Ser Ser Phe
    50                  55                  60

Glu Arg Phe Glu Ile Phe Pro Lys Glu Ser Ser Trp Pro Asn His Thr
65                  70                  75                  80

Val Thr Gly Val Ser Ala Ser Cys Ser His Asn Gly Glu Ser Ser Phe
                85                  90                  95

Tyr Arg Asn Leu Leu Trp Leu Thr Gly Lys Asn Gly Leu Tyr Pro Asn
            100                 105                 110

```
Leu Ser Lys Ser Tyr Ala Asn Asn Lys Glu Lys Glu Val Leu Val Leu
        115                 120                 125

Trp Gly Val His His Pro Asn Ile Gly Asp Gln Lys Ala Leu Tyr
        130                 135                 140

His Thr Glu Asn Ala Tyr Val Ser Val Val Ser Ser His Tyr Ser Arg
145                 150                 155                 160

Lys Phe Thr Pro Glu Ile Ala Lys Arg Pro Lys Val Arg Asp Gln Glu
                165                 170                 175

Gly Arg Ile Asn Tyr Tyr Trp Thr Leu Leu Glu Pro Gly Asp Thr Ile
                180                 185                 190

Ile Phe Glu Ala Asn Gly Asn Leu Ile Ala Pro Arg Tyr Ala Phe Ala
                195                 200                 205

Leu Ser Arg Gly Phe Gly Ser Gly
        210                 215

<210> SEQ ID NO 24
<211> LENGTH: 216
<212> TYPE: PRT
<213> ORGANISM: Influenza A virus

<400> SEQUENCE: 24

Ala Pro Leu Gln Leu Gly Asn Cys Ser Val Ala Gly Trp Ile Leu Gly
1               5                   10                  15

Asn Pro Glu Cys Glu Ser Leu Ile Ser Lys Glu Ser Trp Ser Tyr Ile
                20                  25                  30

Val Glu Thr Pro Asn Pro Glu Asn Gly Thr Cys Tyr Pro Gly Tyr Phe
            35                  40                  45

Ala Asp Tyr Glu Glu Leu Arg Glu Gln Leu Ser Ser Val Ser Ser Phe
        50                  55                  60

Glu Arg Phe Glu Ile Phe Pro Lys Glu Ser Ser Trp Pro Asn His Thr
65                  70                  75                  80

Val Thr Gly Val Thr Ala Ser Cys Ser His Asn Gly Lys Ser Ser Phe
                85                  90                  95

Tyr Arg Asn Leu Leu Trp Leu Thr Glu Lys Asn Gly Leu Tyr Pro Asn
                100                 105                 110

Leu Ser Asn Ser Tyr Val Asn Asn Lys Glu Lys Glu Val Leu Val Leu
        115                 120                 125

Trp Gly Val His His Pro Ser Asn Ile Gly Val Gln Arg Ala Ile Tyr
        130                 135                 140

His Thr Glu Asn Ala Tyr Val Ser Val Val Ser Ser His Tyr Ser Arg
145                 150                 155                 160

Arg Phe Thr Pro Glu Ile Ala Lys Arg Pro Lys Val Arg Gly Gln Glu
                165                 170                 175

Gly Arg Ile Asn Tyr Tyr Trp Thr Leu Leu Glu Pro Gly Asp Thr Ile
                180                 185                 190

Ile Phe Glu Ala Asn Gly Asn Leu Ile Ala Pro Trp Tyr Ala Phe Ala
                195                 200                 205

Leu Ser Arg Gly Phe Gly Ser Gly
        210                 215

<210> SEQ ID NO 25
<211> LENGTH: 216
<212> TYPE: PRT
<213> ORGANISM: Influenza A virus

<400> SEQUENCE:

Ala Pro Leu Gln Leu Gly Asn Cys Ser Val Ala Gly Trp Ile Leu Gly
1               5                   10                  15

Asn Pro Glu Cys Glu Leu Leu Ile Ser Lys Glu Ser Trp Ser Tyr Ile
            20                  25                  30

Val Glu Thr Pro Asn Pro Glu Asn Gly Thr Cys Tyr Pro Gly Tyr Phe
        35                  40                  45

Ala Asp Tyr Glu Glu Leu Arg Glu Gln Leu Ser Ser Val Ser Ser Phe
50                  55                  60

Glu Arg Phe Glu Ile Phe Pro Lys Gly Ser Ser Trp Pro Asn His Thr
65                  70                  75                  80

Val Thr Gly Val Ser Ala Ser Cys Ser His Asn Gly Lys Ser Ser Phe
                85                  90                  95

Tyr Arg Asn Leu Leu Trp Leu Thr Gly Lys Asn Gly Leu Tyr Pro Asn
                100                 105                 110

Leu Ser Met Ser Tyr Val Asn Asn Lys Glu Lys Glu Val Leu Val Leu
            115                 120                 125

Trp Gly Val His His Pro Pro Asn Ile Gly Asp Gln Arg Ala Leu Tyr
130                 135                 140

His Thr Glu Asn Ala Tyr Val Ser Val Val Ser Ser His Tyr Ser Arg
145                 150                 155                 160

Arg Phe Thr Pro Glu Ile Ala Lys Arg Pro Lys Val Arg Asp Gln Glu
                165                 170                 175

Gly Arg Ile Asn Tyr Tyr Trp Thr Leu Leu Glu Pro Gly Asp Thr Ile
            180                 185                 190

Ile Phe Glu Ala Asn Gly Asn Leu Ile Ala Pro Trp Tyr Ala Phe Ala
        195                 200                 205

Leu Ser Arg Gly Phe Gly Ser Gly
210                 215

<210> SEQ ID NO 26
<211> LENGTH: 217
<212> TYPE: PRT
<213> ORGANISM: Influenza A virus

<400> SEQUENCE: 26

Ala Pro Leu Gln Leu Gly Asn Cys Ser Ile Ala Gly Trp Ile Leu Gly
1               5                   10                  15

Asn Pro Glu Cys Glu Ser Leu Phe Ser Lys Lys Ser Trp Ser Tyr Ile
            20                  25                  30

Ala Glu Thr Pro Asn Ser Glu Asn Gly Thr Cys Tyr Pro Gly Tyr Phe
        35                  40                  45

Ala Asp Tyr Glu Glu Leu Arg Glu Gln Leu Ser Ser Val Ser Ser Phe
50                  55                  60

Glu Arg Phe Glu Ile Phe Pro Lys Glu Ser Ser Trp Pro Asn His Thr
65                  70                  75                  80

Val Thr Lys Gly Val Thr Ala Ser Cys Ser His Lys Gly Arg Ser Ser
                85                  90                  95

Phe Tyr Arg Asn Leu Leu Trp Leu Thr Glu Lys Asn Gly Leu Tyr Pro
                100                 105                 110

Asn Leu Ser Lys Ser Tyr Val Asn Asn Lys Glu Lys Glu Val Leu Val
            115                 120                 125

Leu Trp Gly Val His His Pro Ser Asn Ile Gly Asp Gln Arg Ala Ile
130                 135                 140

Tyr His Thr Glu Asn Ala Tyr Val Ser Val Val Ser Ser His Tyr Asn

```
                145                 150                 155                 160
Arg Arg Phe Thr Pro Glu Ile Ala Lys Arg Pro Lys Val Arg Gly Gln
                    165                 170                 175

Glu Gly Arg Ile Asn Tyr Tyr Trp Thr Leu Leu Glu Pro Gly Asp Thr
                180                 185                 190

Ile Ile Phe Glu Ala Asn Gly Asn Leu Ile Ala Pro Trp Tyr Ala Phe
                195                 200                 205

Ala Leu Ser Arg Gly Phe Gly Ser Gly
            210                 215

<210> SEQ ID NO 27
<211> LENGTH: 216
<212> TYPE: PRT
<213> ORGANISM: Influenza A virus

<400> SEQUENCE: 27

Ala Pro Leu Gln Leu Gly Asn Cys Ser Val Ala Gly Trp Ile Leu Gly
1               5                   10                  15

Asn Pro Glu Cys Glu Leu Leu Ile Ser Lys Glu Ser Trp Ser Tyr Ile
            20                  25                  30

Val Glu Thr Pro Asn Pro Glu Asn Gly Thr Cys Tyr Pro Gly Tyr Phe
        35                  40                  45

Ala Asp Tyr Glu Glu Leu Arg Glu Gln Leu Ser Ser Val Ser Ser Phe
    50                  55                  60

Glu Arg Phe Glu Ile Phe Pro Lys Glu Ser Ser Trp Pro Asn His Thr
65                  70                  75                  80

Val Thr Gly Val Ser Ala Ser Cys Ser His Asn Gly Lys Ser Ser Phe
                85                  90                  95

Tyr Arg Asn Leu Leu Trp Leu Thr Gly Lys Asn Gly Leu Tyr Pro Asn
            100                 105                 110

Leu Ser Met Ser Tyr Val Asn Asn Lys Glu Lys Glu Val Leu Val Leu
        115                 120                 125

Trp Gly Val His His Pro Pro Asn Ile Gly Asn Gln Arg Ala Leu Tyr
    130                 135                 140

His Thr Glu Asn Ala Tyr Val Ser Val Val Ser Ser His Tyr Ser Arg
145                 150                 155                 160

Arg Phe Thr Pro Glu Ile Ala Lys Arg Pro Lys Val Arg Asp Gln Glu
                165                 170                 175

Gly Arg Ile Asn Tyr Tyr Trp Thr Leu Leu Glu Pro Gly Asp Thr Ile
                180                 185                 190

Ile Phe Glu Ala Asn Gly Asn Leu Ile Ala Pro Trp Tyr Ala Phe Ala
            195                 200                 205

Leu Ser Arg Gly Phe Gly Ser Gly
        210                 215

<210> SEQ ID NO 28
<211> LENGTH: 216
<212> TYPE: PRT
<213> ORGANISM: Influenza A virus

<400> SEQUENCE: 28

Ala Pro Leu Gln Leu Gly Asn Cys Ser Val Ala Gly Trp Ile Leu Gly
1               5                   10                  15

Asn Pro Glu Cys Glu Leu Leu Ile Ser Lys Gly Ser Trp Ser Tyr Ile
            20                  25                  30

Val Glu Thr Pro Asn Pro Glu Asn Gly Thr Cys Tyr Pro Gly Tyr Phe
```

```
               35                  40                  45
Ala Asp Tyr Glu Glu Leu Arg Glu Gln Leu Ser Ser Val Ser Ser Phe
 50                  55                  60

Glu Arg Phe Glu Ile Phe Pro Lys Gly Ser Ser Trp Pro Asn His Thr
 65                  70                  75                  80

Val Thr Gly Val Ser Ala Ser Cys Ser His Asn Gly Lys Ser Ser Phe
                 85                  90                  95

Tyr Arg Asn Leu Leu Trp Leu Thr Gly Lys Asn Gly Leu Tyr Pro Asn
                100                 105                 110

Leu Ser Met Ser Tyr Val Asn Asn Lys Glu Lys Glu Val Leu Val Leu
                115                 120                 125

Trp Gly Val His His Pro Pro Asn Ile Gly Asn Gln Arg Ala Leu Tyr
                130                 135                 140

His Thr Glu Asn Ala Tyr Val Ser Val Val Ser Ser His Tyr Ser Arg
145                 150                 155                 160

Arg Phe Thr Pro Glu Ile Ala Lys Arg Pro Lys Val Arg Asp Gln Glu
                165                 170                 175

Gly Arg Ile Asn Tyr Tyr Trp Thr Leu Leu Glu Pro Gly Asp Thr Ile
                180                 185                 190

Ile Phe Glu Ala Asn Gly Asn Leu Ile Ala Pro Trp Tyr Ala Phe Ala
                195                 200                 205

Leu Ser Arg Gly Phe Gly Ser Gly
                210                 215

<210> SEQ ID NO 29
<211> LENGTH: 216
<212> TYPE: PRT
<213> ORGANISM: Influenza A virus

<400> SEQUENCE: 29

Ala Pro Leu Gln Leu Gly Asn Cys Ser Val Ala Gly Trp Ile Leu Gly
 1                   5                  10                  15

Asn Pro Glu Cys Glu Leu Leu Ile Ser Lys Glu Ser Trp Ser Tyr Ile
                 20                  25                  30

Val Glu Thr Pro Asn Pro Glu Asn Gly Thr Cys Tyr Pro Gly Tyr Phe
                 35                  40                  45

Ala Asp Tyr Glu Glu Leu Arg Glu Gln Leu Ser Ser Val Ser Ser Phe
 50                  55                  60

Glu Arg Phe Glu Ile Phe Pro Lys Gly Ser Ser Trp Pro Asn His Thr
 65                  70                  75                  80

Val Thr Gly Val Ser Ala Ser Cys Ser His Asn Gly Lys Ser Ser Phe
                 85                  90                  95

Tyr Arg Asn Leu Leu Trp Leu Thr Gly Lys Asn Gly Leu Tyr Pro Asn
                100                 105                 110

Leu Ser Lys Ser Tyr Ala Asn Asn Lys Lys Glu Val Leu Val Leu
                115                 120                 125

Trp Gly Val His His Pro Pro Asn Ile Gly Asn Gln Arg Ala Leu Tyr
                130                 135                 140

His Thr Glu Asn Ala Tyr Val Ser Val Val Ser Ser His Tyr Ser Arg
145                 150                 155                 160

Arg Phe Thr Pro Glu Ile Ala Lys Arg Pro Lys Val Arg Asp Gln Glu
                165                 170                 175

Gly Arg Ile Asn Tyr Tyr Trp Thr Leu Leu Glu Pro Gly Asp Thr Ile
                180                 185                 190
```

```
Ile Phe Glu Ala Asn Gly Asn Leu Ile Ala Pro Arg Tyr Ala Phe Ala
            195                 200                 205

Leu Ser Arg Gly Phe Gly Ser Gly
    210                 215

<210> SEQ ID NO 30
<211> LENGTH: 216
<212> TYPE: PRT
<213> ORGANISM: Influenza A virus

<400> SEQUENCE: 30

Ala Pro Leu Gln Leu Gly Asn Cys Ser Val Ala Gly Trp Ile Leu Gly
1               5                   10                  15

Asn Pro Glu Cys Glu Leu Leu Ile Ser Lys Glu Ser Trp Ser Tyr Ile
            20                  25                  30

Val Glu Thr Pro Asn Pro Glu Asn Gly Ala Cys Tyr Pro Gly Tyr Phe
        35                  40                  45

Ala Asp Tyr Glu Glu Leu Arg Glu Gln Leu Ser Ser Val Ser Ser Phe
    50                  55                  60

Glu Arg Phe Glu Ile Phe Pro Lys Lys Ser Ser Trp Pro Asn His Thr
65                  70                  75                  80

Val Thr Gly Val Ser Ala Ser Cys Ser His Asn Gly Lys Ser Ser Phe
                85                  90                  95

Tyr Arg Asn Leu Leu Trp Leu Thr Gly Lys Asn Gly Leu Tyr Pro Asn
            100                 105                 110

Leu Ser Lys Ser Tyr Ala Asn Asn Lys Lys Lys Glu Val Leu Ile Leu
        115                 120                 125

Trp Gly Val His His Pro Pro Asn Ile Gly Asp Gln Arg Thr Leu Tyr
    130                 135                 140

His Thr Glu Asn Ala Tyr Val Ser Val Val Ser Ser His Tyr Ser Arg
145                 150                 155                 160

Arg Phe Thr Pro Glu Ile Thr Lys Arg Pro Lys Val Arg Asp Gln Glu
                165                 170                 175

Gly Arg Ile Asn Tyr Tyr Trp Thr Leu Leu Glu Pro Gly Asp Thr Ile
            180                 185                 190

Ile Phe Glu Ala Asn Gly Asn Leu Ile Ala Pro Trp Tyr Ala Phe Ala
        195                 200                 205

Leu Ser Arg Gly Phe Gly Ser Gly
    210                 215

<210> SEQ ID NO 31
<211> LENGTH: 216
<212> TYPE: PRT
<213> ORGANISM: Influenza A virus

<400> SEQUENCE: 31

Ala Pro Leu Gln Leu Gly Asn Cys Ser Val Ala Gly Trp Ile Leu Gly
1               5                   10                  15

```
Val Thr Gly Val Ser Ala Ser Cys Ser His Asn Gly Lys Ser Ser Phe
                85                  90                  95
Tyr Arg Asn Leu Leu Trp Leu Thr Gly Lys Asn Gly Leu Tyr Pro Asn
            100                 105                 110
Leu Ser Lys Ser Tyr Ala Asn Asn Lys Lys Lys Glu Val Leu Ile Leu
        115                 120                 125
Trp Gly Val His His Pro Pro Asn Ile Gly Asp Gln Arg Thr Leu Tyr
    130                 135                 140
His Thr Glu Asn Ala Tyr Val Ser Val Val Ser Ser His Tyr Ser Arg
145                 150                 155                 160
Arg Phe Thr Pro Glu Ile Thr Lys Arg Pro Lys Val Arg Asp Gln Glu
                165                 170                 175
Gly Arg Ile Asn Tyr Tyr Trp Thr Leu Leu Glu Pro Gly Asp Thr Ile
            180                 185                 190
Ile Phe Glu Ala Asn Gly Asn Leu Ile Ala Pro Trp Tyr Ala Phe Ala
        195                 200                 205
Leu Ser Arg Gly Phe Gly Ser Gly
    210                 215

<210> SEQ ID NO 32
<211> LENGTH: 216
<212> TYPE: PRT
<213> ORGANISM: Influenza A virus

<400> SEQUENCE: 32

Ala Pro Leu Gln Leu Gly Asn Cys Ser Val Ala Gly Trp Ile Leu Gly
1               5                   10                  15
Asn Pro Glu Cys Glu Leu Leu Ile Ser Lys Glu Ser Trp Ser Tyr Ile
                20                  25                  30
Val Glu Thr Pro Asn Pro Glu Asn Gly Thr Cys Tyr Pro Gly Tyr Phe
            35                  40                  45
Ala Asp Tyr Glu Glu Leu Arg Glu Gln Leu Ser Ser Val Ser Ser Phe
        50                  55                  60
Glu Arg Phe Glu Ile Phe Pro Lys Glu Ser Ser Trp Pro Asn His Thr
65                  70                  75                  80
Val Thr Gly Val Ser Ala Ser Cys Ser His Asn Gly Lys Ser Ser Phe
                85                  90                  95
Tyr Arg Asn Leu Leu Trp Leu Thr Gly Lys Asn Gly Leu Tyr Pro Asn
            100                 105                 110
Leu Ser Lys Ser Tyr Ala Asn Asn Lys Glu Lys Glu Val Leu Val Leu
        115                 120                 125
Trp Gly Val His His Pro Pro Asn Ile Gly Asn Gln Arg Ala Leu Tyr
    130                 135                 140
His Thr Glu Asn Ala Tyr Val Ser Val Val Ser Ser His Tyr Ser Arg
145                 150                 155                 160
Arg Phe Thr Pro Glu Ile Ala Lys Arg Pro Lys Val Arg Asp Gln Glu
                165                 170                 175
Gly Arg Ile Asn Tyr Tyr Trp Thr Leu Leu Glu Pro Gly Asp Thr Ile
            180                 185                 190
Ile Phe Glu Ala Asn Gly Asn Leu Ile Ala Pro Arg Tyr Ala Phe Ala
        195                 200                 205
Leu Ser Arg Gly Phe Gly Ser Gly
    210                 215

<210> SEQ ID NO 33
```

<211> LENGTH: 216
<212> TYPE: PRT
<213> ORGANISM: Influenza A virus

<400> SEQUENCE: 33

```
Ala Pro Leu Gln Leu Gly Asn Cys Ser Val Ala Gly Trp Ile Leu Gly
1               5                   10                  15

Asn Pro Glu Cys Glu Ser Leu Ile Ser Lys Glu Ser Trp Ser Tyr Ile
            20                  25                  30

Val Glu Thr Pro Asn Pro Glu Asn Gly Thr Cys Tyr Pro Gly Tyr Phe
        35                  40                  45

Ala Asp Tyr Glu Glu Leu Arg Glu Gln Leu Ser Ser Val Ser Ser Phe
    50                  55                  60

Glu Arg Phe Glu Ile Phe Pro Lys Glu Ser Ser Trp Pro Asn His Thr
65                  70                  75                  80

Val Thr Gly Val Ser Ala Ser Cys Ser His Asn Gly Lys Ser Ser Phe
                85                  90                  95

Tyr Arg Asn Leu Leu Trp Leu Thr Lys Lys Asn Gly Leu Tyr Pro Asn
            100                 105                 110

Leu Ser Lys Ser Tyr Val Asn Asn Lys Glu Lys Glu Val Leu Val Leu
        115                 120                 125

Trp Gly Val His His Pro Ser Asn Ile Gly Asp Gln Arg Thr Ile Tyr
    130                 135                 140

His Thr Glu Asn Ala Tyr Val Ser Val Val Ser Ser His Tyr Ser Arg
145                 150                 155                 160

Arg Phe Thr Pro Glu Ile Ala Lys Arg Pro Lys Val Arg Asp Gln Glu
                165                 170                 175

Gly Arg Ile Asn Tyr Tyr Trp Thr Leu Leu Glu Pro Gly Asp Thr Ile
            180                 185                 190

Ile Phe Glu Ala Asn Gly Asn Leu Ile Ala Pro Trp Tyr Ala Phe Ala
        195                 200                 205

Leu Ser Arg Gly Phe Gly Ser Gly
        210                 215
```

<210> SEQ ID NO 34
<211> LENGTH: 217
<212> TYPE: PRT
<213> ORGANISM: Influenza A virus

<400> SEQUENCE: 34

```
Ala Pro Leu His Leu Gly Lys Cys Asn Ile Ala Gly Trp Ile Leu Gly
1               5                   10                  15

Asn Pro Glu Cys Glu Ser Leu Ser Thr Ala Ser Ser Trp Ser Tyr Ile
            20                  25                  30

Val Glu Thr Pro Ser Ser Asp Asn Gly Thr Cys Tyr Pro Gly Asp Phe
        35                  40                  45

Ile Asp Tyr Glu Glu Leu Arg Glu Gln Leu Ser Ser Val Ser Ser Phe
    50                  55                  60

Glu Arg Phe Glu Ile Phe Pro Lys Thr Ser Ser Trp Pro Asn His Asp
65                  70                  75                  80

Ser Asn Lys Gly Val Thr Ala Ala Cys Pro His Ala Gly Ala Lys Ser
                85                  90                  95

Phe Tyr Lys Asn Leu Ile Trp Leu Val Lys Lys Gly Asn Ser Tyr Pro
            100                 105                 110

Lys Leu Ser Lys Ser Tyr Ile Asn Asp Lys Gly Lys Glu Val Leu Val
        115                 120                 125
```

Leu Trp Gly Ile His His Pro Ser Thr Ser Ala Asp Gln Ser Leu
            130                 135                 140

Tyr Gln Asn Ala Asp Ala Tyr Val Phe Val Gly Ser Ser Arg Tyr Ser
145                 150                 155                 160

Lys Lys Phe Lys Pro Glu Ile Ala Ile Arg Pro Lys Val Arg Asp Gln
                165                 170                 175

Glu Gly Arg Met Asn Tyr Tyr Trp Thr Leu Val Glu Pro Gly Asp Lys
            180                 185                 190

Ile Thr Phe Glu Ala Thr Gly Asn Leu Val Val Pro Arg Tyr Ala Phe
        195                 200                 205

Ala Met Glu Arg Asn Ala Gly Ser Gly
            210                 215

<210> SEQ ID NO 35
<211> LENGTH: 223
<212> TYPE: PRT
<213> ORGANISM: Influenza A virus

<400> SEQUENCE: 35

Asn Gly Lys Leu Cys Lys Leu Asn Gly Ile Pro Pro Leu Glu Leu Gly
1               5                   10                  15

Asp Cys Ser Ile Ala Gly Trp Leu Leu Gly Asn Pro Glu Cys Asp Arg
            20                  25                  30

Leu Leu Ser Val Pro Glu Trp Ser Tyr Ile Met Glu Lys Glu Asn Pro
        35                  40                  45

Arg Asn Gly Leu Cys Tyr Pro Gly Ser Phe Asn Asp Tyr Glu Glu Leu
    50                  55                  60

Lys His Leu Leu Ser Ser Val Lys His Phe Glu Lys Val Lys Ile Leu
65                  70                  75                  80

Pro Lys Asp Arg Trp Thr Gln His Thr Thr Thr Gly Gly Ser Gln Ala
                85                  90                  95

Cys Ala Val Ser Gly Asn Pro Ser Phe Phe Arg Asn Met Val Trp Leu
            100                 105                 110

Thr Lys Lys Gly Ser Asp Tyr Pro Val Ala Lys Gly Ser Tyr Asn Asn
        115                 120                 125

Thr Ser Gly Glu Gln Met Leu Ile Ile Trp Gly Val His His Pro Ile
    130                 135                 140

Asp Glu Thr Glu Gln Arg Thr Leu Tyr Gln Asn Val Gly Thr Tyr Val
145                 150                 155                 160

Ser Val Gly Thr Ser Thr Leu Asn Lys Arg Ser Thr Pro Glu Ile Ala
                165                 170                 175

Thr Arg Pro Lys Val Asn Gly Leu Gly Ser Arg Met Glu Phe Ser Trp
            180                 185                 190

Thr Leu Leu Asp Met Trp Asp Thr Ile Asn Phe Glu Ser Thr Gly Asn
        195                 200                 205

Leu Ile Ala Pro Glu Tyr Gly Phe Lys Ile Lys Arg Gly Ser Ser
    210                 215                 220

<210> SEQ ID NO 36
<211> LENGTH: 224
<212> TYPE: PRT
<213> ORGANISM: Influenza A virus

<400> SEQUENCE: 36

Asn Gly Lys Leu Cys Lys Leu Asn Gly Ile Pro Pro Leu Glu Leu Gly
1               5                   10                  15

Asp Cys Ser Ile Ala Gly Trp Leu Leu Gly Asn Pro Glu Cys Asp Arg
            20                  25                  30

Leu Leu Arg Val Pro Glu Trp Ser Tyr Ile Met Glu Lys Glu Asn Pro
        35                  40                  45

Arg Asp Gly Leu Cys Tyr Pro Gly Ser Phe Asn Asp Tyr Glu Glu Leu
    50                  55                  60

Lys His Leu Leu Ser Ser Val Lys His Phe Glu Lys Val Arg Ile Leu
65                  70                  75                  80

Pro Lys Asp Arg Trp Thr Gln His Thr Thr Thr Gly Gly Ser Arg Ala
                85                  90                  95

Cys Ala Val Ser Gly Asn Pro Ser Phe Phe Arg Asn Met Ile Trp Leu
            100                 105                 110

Thr Lys Lys Gly Ser Asn Tyr Pro Val Ala Lys Gly Ser Tyr Asn Asn
        115                 120                 125

Thr Ser Gly Glu Gln Met Leu Ile Ile Trp Gly Val His His Pro Ile
    130                 135                 140

Asp Glu Thr Glu Gln Arg Thr Leu Tyr Gln Asn Val Glu Thr Tyr Val
145                 150                 155                 160

Ser Val Val Thr Ser Thr Leu Asn Lys Arg Ser Thr Pro Lys Ile Ala
                165                 170                 175

Thr Arg Pro Lys Val Asn Gly Leu Gly Gly Arg Met Glu Phe Ser Trp
            180                 185                 190

Thr Leu Leu Asp Met Trp Asp Thr Ile Asn Phe Glu Ser Thr Gly Asn
        195                 200                 205

Leu Ile Ala Pro Glu Tyr Gly Phe Lys Ile Ser Lys Arg Gly Ser Ser
    210                 215                 220

<210> SEQ ID NO 37
<211> LENGTH: 224
<212> TYPE: PRT
<213> ORGANISM: Influenza A virus

<400> SEQUENCE: 37

Asn Gly Lys Leu Cys Lys Leu Asn Gly Ile Pro Pro Leu Glu Leu Gly
1               5                   10                  15

Asp Cys Ser Ile Ala Gly Trp Leu Leu Gly Asn Pro Glu Cys Asp Arg
            20                  25                  30

Leu Leu Ser Val Pro Glu Trp Ser Tyr Ile Met Glu Lys Glu Asn Pro
        35                  40                  45

Arg Asp Gly Leu Cys Tyr Pro Gly Ser Phe Asn Asp Tyr Glu Glu Leu
    50                  55                  60

Lys His Leu Leu Ser Ser Val Lys His Phe Glu Lys Val Lys Ile Leu
65                  70                  75                  80

Pro Lys Asp Arg Trp Thr Gln His Thr Thr Thr Gly Gly Ser Arg Ala
                85                  90                  95

Cys Ala Val Ser Gly Asn Pro Ser Phe Phe Arg Asn Met Val Trp Leu
            100                 105                 110

Thr Glu Lys Gly Ser Asn Tyr Pro Val Ala Lys Gly Ser Tyr Asn Asn
        115                 120                 125

Thr Ser Gly Glu Gln Met Leu Ile Ile Trp Gly Val His His Pro Asn
    130                 135                 140

Asp Glu Thr Glu Gln Arg Thr Leu Tyr Gln Asn Val Gly Thr Tyr Val
145                 150                 155                 160

Ser Val Gly Thr Ser Thr Leu Asn Lys Arg Ser Thr Pro Glu Ile Ala 165                 170                 175

Thr Arg Pro Lys Val Asn Gly Leu Gly Gly Arg Met Glu Phe Ser Trp
            180                 185                 190

Thr Leu Leu Asp Met Trp Asp Thr Ile Asn Phe Glu Ser Thr Gly Asn
        195                 200                 205

Leu Ile Ala Pro Glu Tyr Gly Phe Lys Ile Ser Lys Arg Gly Ser Ser
    210                 215                 220

<210> SEQ ID NO 38
<211> LENGTH: 224
<212> TYPE: PRT
<213> ORGANISM: Influenza A virus

<400> SEQUENCE: 38

Asn Gly Lys Leu Cys Lys Leu Asn Gly Ile Pro Pro Leu Glu Leu Gly
1               5                   10                  15

Asp Cys Ser Ile Ala Gly Trp Leu Leu Gly Asn Pro Glu Cys Asp Arg
            20                  25                  30

Leu Leu Arg Val Pro Glu Trp Ser Tyr Ile Met Glu Lys Glu Asn Pro
        35                  40                  45

Arg Tyr Ser Leu Cys Tyr Pro Gly Ser Phe Asn Asp Tyr Glu Glu Leu
    50                  55                  60

Lys His Leu Leu Ser Ser Val Lys His Phe Glu Lys Val Arg Ile Leu
65                  70                  75                  80

Pro Lys Asp Arg Trp Thr Gln His Thr Thr Thr Gly Asp Ser Lys Ala
                85                  90                  95

Cys Ala Val Ser Gly Lys Pro Ser Phe Phe Arg Asn Met Val Trp Leu
            100                 105                 110

Thr Lys Lys Gly Pro Asn Tyr Pro Val Ala Lys Gly Ser Tyr Asn Asn
        115                 120                 125

Thr Ser Gly Glu Gln Met Leu Ile Ile Trp Gly Val His His Pro Lys
    130                 135                 140

Asp Glu Ala Glu Gln Arg Ala Leu Tyr Gln Asn Val Gly Thr Tyr Val
145                 150                 155                 160

Ser Ala Ser Thr Ser Thr Leu Asn Lys Arg Ser Ile Pro Glu Ile Ala
                165                 170                 175

Thr Arg Pro Glu Val Asn Gly Leu Gly Ser Arg Met Glu Phe Ser Trp
            180                 185                 190

Thr Leu Leu Asp Ala Trp Asp Thr Ile Asn Phe Glu Ser Thr Gly Asn
        195                 200                 205

Leu Val Ala Pro Glu Tyr Gly Phe Lys Ile Ser Lys Arg Gly Ser Ser
    210                 215                 220

<210> SEQ ID NO 39
<211> LENGTH: 211
<212> TYPE: PRT
<213> ORGANISM: Influenza A virus

<400> SEQUENCE: 39

His Gln Ile Leu Asp Gly Glu Asn Cys Thr Leu Ile Asp Ala Leu Leu
1               5                   10                  15

Gly Asp Pro Gln Cys Asp Gly Phe Gln Asn Lys Lys Trp Asp Leu Phe
            20                  25                  30

Val Glu Arg Ser Lys Ala Tyr Ser Asn Cys Tyr Pro Tyr Asp Val Pro
        35                  40                  45

Asp Tyr Ala Ser Leu Arg Ser Leu Val Ala Ser Ser Gly Thr Leu Glu

Phe Asn Asp Glu Ser Phe Asn Trp Thr Gly Val Thr Gln Asn Gly Thr
65                  70                  75                  80

Ser Ser Ser Cys Lys Arg Arg Ser Asn Asn Ser Phe Phe Ser Arg Leu
                85                  90                  95

Asn Trp Leu Thr His Leu Lys Phe Lys Tyr Pro Ala Leu Asn Val Thr
            100                 105                 110

Met Pro Asn Asn Glu Lys Phe Asp Lys Leu Tyr Ile Trp Gly Val His
            115                 120                 125

His Pro Val Thr Asp Asn Asp Gln Ile Phe Leu Tyr Ala Gln Ala Ser
        130                 135                 140

Gly Arg Ile Thr Val Ser Thr Lys Arg Ser Gln Gln Thr Val Ile Pro
145                 150                 155                 160

Asn Ile Gly Ser Arg Pro Arg Ile Arg Asn Ile Pro Ser Arg Ile Ser
                165                 170                 175

Ile Tyr Trp Thr Ile Val Lys Pro Gly Asp Ile Leu Leu Ile Asn Ser
            180                 185                 190

Thr Gly Asn Leu Ile Ala Pro Arg Gly Tyr Phe Lys Ile Arg Ser Gly
        195                 200                 205

Lys Ser Ser
    210

<210> SEQ ID NO 40
<211> LENGTH: 211
<212> TYPE: PRT
<213> ORGANISM: Influenza A virus

<400> SEQUENCE: 40

His Gln Ile Leu Asp Gly Lys Asn Cys Thr Leu Ile Asp Ala Leu Leu
1               5                   10                  15

Gly Asp Pro Gln Cys Asp Gly Phe Gln Asn Lys Lys Trp Asp Leu Phe
            20                  25                  30

Val Glu Arg Ser Lys Ala Tyr Ser Asn Cys Tyr Pro Tyr Asp Val Pro
            35                  40                  45

Asp Tyr Ala Ser Leu Arg Ser Leu Val Ala Ser Ser Gly Thr Leu Glu
        50                  55                  60

Phe Asn Asn Glu Ser Phe Asn Trp Thr Gly Val Thr Gln Asn Gly Thr
65                  70                  75                  80

Ser Ser Ala Cys Ile Arg Arg Ser Lys Asn Ser Phe Phe Ser Arg Leu
                85                  90                  95

Asn Trp Leu Thr His Leu Asn Phe Lys Tyr Pro Ala Leu Asn Val Thr
            100                 105                 110

Met Pro Asn Asn Glu Gln Phe Asp Lys Leu Tyr Ile Trp Gly Val His
            115                 120                 125

His Pro Gly Thr Asp Lys Asp Gln Ile Phe Pro Tyr Ala Gln Ala Ser
        130                 135                 140

Gly Arg Ile Thr Val Ser Thr Lys Arg Ser Gln Gln Thr Ala Ile Pro
145                 150                 155                 160

Asn Ile Gly Ser Arg Pro Arg Val Arg Asn Ile Pro Ser Arg Ile Ser
                165                 170                 175

Ile Tyr Trp Thr Ile Val Lys Pro Gly Asp Ile Leu Leu Ile Asn Ser
            180                 185                 190

Thr Gly Asn Leu Ile Ala Pro Arg Gly Tyr Phe Lys Ile Arg Ser Gly
        195                 200                 205

-continued

```
Lys Ser Ser
    210

<210> SEQ ID NO 41
<211> LENGTH: 211
<212> TYPE: PRT
<213> ORGANISM: Influenza A virus

<400> SEQUENCE: 41

His Arg Ile Leu Asp Gly Ile Asp Cys Thr Leu Ile Asp Ala Leu Leu
1               5                   10                  15

Gly Asp Pro His Cys Asp Val Phe Gln Asn Glu Thr Trp Asp Leu Phe
            20                  25                  30

Val Glu Arg Ser Lys Ala Phe Ser Asn Cys Tyr Pro Tyr Asp Val Pro
        35                  40                  45

Asp Tyr Ala Ser Leu Arg Ser Leu Val Ala Ser Ser Gly Thr Leu Glu
    50                  55                  60

Phe Ile Thr Glu Gly Phe Thr Trp Thr Gly Val Thr Gln Asn Gly Gly
65                  70                  75                  80

Ser Asn Ala Cys Lys Arg Gly Pro Gly Ser Gly Phe Phe Ser Arg Leu
                85                  90                  95

Asn Trp Leu Thr Lys Ser Gly Ser Thr Tyr Pro Val Leu Asn Val Thr
            100                 105                 110

Met Pro Asn Asn Asp Asn Phe Asp Lys Leu Tyr Ile Trp Gly Ile His
        115                 120                 125

His Pro Ser Thr Asp Gln Glu Gln Thr Ser Leu Tyr Val Gln Ala Ser
    130                 135                 140

Gly Arg Val Thr Val Ser Thr Arg Arg Ser Gln Gln Thr Ile Ile Pro
145                 150                 155                 160

Asn Ile Gly Ser Arg Pro Trp Val Arg Gly Leu Ser Ser Arg Ile Ser
                165                 170                 175

Ile Tyr Trp Thr Ile Val Lys Pro Gly Asp Val Leu Val Ile Asn Ser
            180                 185                 190

Asn Gly Asn Leu Ile Ala Pro Arg Gly Tyr Phe Lys Met Arg Thr Gly
        195                 200                 205

Lys Ser Ser
    210

<210> SEQ ID NO 42
<211> LENGTH: 211
<212> TYPE: PRT
<213> ORGANISM: Influenza A virus

<400> SEQUENCE: 42

His Gln Ile Leu Asp Gly Glu Asn Cys Thr Leu Ile Asp Ala Leu Leu
1               5                   10                  15

Gly Asp Pro Gln Cys Asp Gly Phe Gln Asn Lys Lys Trp Asp Leu Phe
            20                  25                  30

Val Glu Arg Ser Lys Ala Tyr Ser Asn Cys Tyr Pro Tyr Asp Val Pro
        35                  40                  45

Asp Tyr Ala Ser Leu Arg Ser Leu Val Ala Ser Ser Gly Thr Leu Glu
    50                  55                  60

Phe Asn Asn Glu Ser Phe Asn Trp Thr Gly Val Thr Gln Asn Gly Thr
65                  70                  75                  80

Ser Ser Ala Cys Ile Arg Arg Ser Asn Asn Ser Phe Phe Ser Arg Leu
                85                  90                  95
```

```
Asn Trp Leu Thr His Leu Lys Phe Lys Tyr Pro Ala Leu Asn Val Thr
            100                 105                 110

Met Pro Asn Asn Glu Lys Phe Asp Lys Leu Tyr Ile Trp Gly Val His
        115                 120                 125

His Pro Gly Thr Asp Asn Asp Gln Ile Phe Pro Tyr Ala Gln Ala Ser
    130                 135                 140

Gly Arg Ile Thr Val Ser Thr Lys Arg Ser Gln Gln Thr Val Ile Pro
145                 150                 155                 160

Asn Ile Gly Ser Arg Pro Arg Val Arg Asn Ile Pro Ser Arg Ile Ser
                165                 170                 175

Ile Tyr Trp Thr Ile Val Lys Pro Gly Asp Ile Leu Leu Ile Asn Ser
                180                 185                 190

Thr Gly Asn Leu Ile Ala Pro Arg Gly Tyr Phe Lys Ile Arg Ser Gly
            195                 200                 205

Lys Ser Ser
    210

<210> SEQ ID NO 43
<211> LENGTH: 211
<212> TYPE: PRT
<213> ORGANISM: Influenza A virus

<400> SEQUENCE: 43

His Gln Ile Leu Asp Gly Glu Asn Cys Thr Leu Ile Asp Ala Leu Leu
1               5                   10                  15

Gly Asp Pro His Cys Asp Gly Phe Gln Asn Lys Glu Trp Asp Leu Phe
            20                  25                  30

Val Glu Arg Ser Lys Ala Tyr Ser Asn Cys Tyr Pro Tyr Asp Val Pro
        35                  40                  45

Asp Tyr Ala Ser Leu Arg Ser Leu Val Ala Ser Ser Gly Thr Leu Glu
    50                  55                  60

Phe Asn Asn Glu Ser Phe Asn Trp Thr Gly Val Ala Gln Asn Gly Thr
65                  70                  75                  80

Ser Ser Ser Cys Lys Arg Arg Ser Ile Lys Ser Phe Phe Ser Arg Leu
                85                  90                  95

Asn Trp Leu His Gln Leu Lys Tyr Arg Tyr Pro Ala Leu Asn Val Thr
            100                 105                 110

Met Pro Asn Asn Asp Lys Phe Asp Lys Leu Tyr Ile Trp Gly Val His
        115                 120                 125

His Pro Ser Thr Asp Ser Asp Gln Thr Ser Leu Tyr Thr Gln Ala Ser
    130                 135                 140

Gly Arg Val Thr Val Ser Thr Lys Arg Ser Gln Gln Thr Val Ile Pro
145                 150                 155                 160

Asn Ile Gly Ser Arg Pro Trp Val Arg Gly Ile Ser Ser Arg Ile Ser
                165                 170                 175

Ile Tyr Trp Thr Ile Val Lys Pro Gly Asp Ile Leu Leu Ile Asn Ser
                180                 185                 190

Thr Gly Asn Leu Ile Ala Pro Arg Gly Tyr Phe Lys Ile Arg Ser Gly
            195                 200                 205

Lys Ser Ser
    210

<210> SEQ ID NO 44
<211> LENGTH: 215
<212> TYPE: PRT
<213> ORGANISM: Influenza A virus
```

<400> SEQUENCE: 44

```
Val Lys Pro Leu Ile Leu Arg Asp Cys Ser Val Ala Gly Trp Leu Leu
1               5                   10                  15

Gly Asn Pro Met Cys Asp Glu Phe Ile Asn Val Pro Glu Trp Ser Tyr
            20                  25                  30

Ile Val Glu Lys Ala Asn Pro Thr Asn Asp Leu Cys Tyr Pro Gly Ser
        35                  40                  45

Phe Asn Asp Tyr Glu Glu Leu Lys His Leu Leu Ser Arg Ile Asn His
    50                  55                  60

Phe Glu Lys Ile Gln Ile Ile Pro Lys Ser Ser Trp Ser Asp His Glu
65                  70                  75                  80

Ala Ser Ser Gly Val Ser Ser Ala Cys Pro Tyr Leu Gly Ser Pro Ser
                85                  90                  95

Phe Phe Arg Asn Val Val Trp Leu Ile Lys Lys Asn Ser Thr Tyr Pro
            100                 105                 110

Thr Ile Lys Lys Ser Tyr Asn Asn Thr Asn Gln Glu Asp Leu Leu Val
        115                 120                 125

Leu Trp Gly Ile His His Pro Lys Asp Ala Ala Glu Gln Thr Arg Leu
    130                 135                 140

Tyr Gln Asn Pro Thr Thr Tyr Ile Ser Ile Gly Thr Ser Thr Leu Asn
145                 150                 155                 160

Gln Arg Leu Val Pro Lys Ile Ala Thr Arg Ser Lys Val Asn Gly Leu
                165                 170                 175

Ser Ser Arg Met Glu Phe Phe Trp Thr Ile Leu Lys Pro Asn Asp Ala
            180                 185                 190

Ile Asn Phe Glu Ser Asn Gly Asn Phe Ile Ala Pro Glu Tyr Ala Tyr
        195                 200                 205

Lys Ile Val Lys Lys Gly Asp
        210                 215
```

<210> SEQ ID NO 45
<211> LENGTH: 216
<212> TYPE: PRT
<213> ORGANISM: Influenza A virus

<400> SEQUENCE: 45

```
Val Lys Pro Leu Ile Leu Arg Asp Cys Ser Val Ala Gly Trp Leu Leu
1               5                   10                  15

Gly Asn Pro Met Cys Asp Glu Phe Ile Asn Val Pro Glu Trp Ser Tyr
            20                  25                  30

Ile Val Glu Lys Ala Asn Pro Thr Asn Asp Leu Cys Tyr Pro Gly Ser
        35                  40                  45

Phe Asn Asp Tyr Glu Glu Leu Lys His Leu Leu Ser Arg Ile Asn His
    50                  55                  60

Phe Glu Lys Ile Gln Ile Ile Pro Lys Ser Ser Trp Ser Asp His Glu
65                  70                  75                  80

Ala Ser Ser Gly Val Ser Ser Ala Cys Pro Tyr Leu Gly Ser Pro Ser
                85                  90                  95

Phe Phe Arg Asn Val Val Trp Leu Ile Lys Lys Asn Ser Thr Tyr Pro
            100                 105                 110

Thr Ile Lys Lys Ser Tyr Asn Asn Thr Asn Gln Glu Asp Leu Leu Val
        115                 120                 125

Leu Trp Gly Ile His His Pro Asn Asp Ala Ala Glu Gln Thr Arg Leu
    130                 135                 140
```

Tyr Gln Asn Pro Thr Thr Tyr Ile Ser Ile Gly Thr Ser Thr Leu Asn
145                 150                 155                 160

Gln Arg Leu Val Pro Lys Ile Ala Thr Arg Ser Lys Val Asn Gly Gln
            165                 170                 175

Ser Gly Arg Met Glu Phe Phe Trp Thr Ile Leu Lys Pro Asn Asp Ala
        180                 185                 190

Ile Asn Phe Glu Ser Asn Gly Asn Phe Ile Ala Pro Glu Tyr Ala Tyr
    195                 200                 205

Lys Ile Val Lys Lys Gly Asp Ser
210                 215

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 46

His His His His His His
1               5

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
aagcttacca tgccgatggg ctcc                                          24

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gagcccaaat cttgtgacaa atgatctaga                                    30

<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
tcttgtgaca aa                                                       12

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Cys Asp Lys
1

<210> SEQ ID NO 51
<211> LENGTH: 126
<212> TYPE: PRT
<213> ORGANISM: Homo sapiens
<220> FEATURE:
<221> NAME/KEY: MOD_RES
<222> LOCATION: (99)..(99)
<223> OTHER INFORMATION: Gly or Ala

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Xaa Gly Leu Glu Pro Arg Ser Val Asp Tyr Tyr Tyr Tyr Gly
            100                 105                 110

Met Asp Val Trp Gly Gln Gly Thr Thr Val Thr Val Ser Ser
        115                 120                 125

<210> SEQ ID NO 52
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
attattgtgc gagaggggga ctggaacccc gatctgtaga ctactactat tatggtatgg    60
acgtctgg                                                             68

<210> SEQ ID NO 53
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
attactgtgc gagagggga ctggaacccc gatctgtaga ctactactac tacggtatgg     60
acgtctgg                                                             68

<210> SEQ ID NO 54
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
attactgtgc gaga    14

<210> SEQ ID NO 55
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggtacaactg gaacgac    17

<210> SEQ ID NO 56
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
attactacta ctactacggt atggacgtct gg    32

<210> SEQ ID NO 57
<211> LENGTH: 214
<212> TYPE: PRT
<213> ORGANISM: Influenza A virus

<400> SEQUENCE: 57

```
Lys Pro Leu Ile Leu Arg Asp Cys Ser Val Ala Gly Trp Leu Leu Gly
1               5                   10                  15

Asn Pro Met Cys Asp Glu Phe Ile Asn Val Pro Glu Trp Ser Tyr Ile
            20                  25                  30

Val Glu Lys Ala Asn Pro Thr Asn Asp Leu Cys Tyr Pro Gly Ser Phe
        35                  40                  45

Asn Asp Tyr Glu Glu Leu Lys His Leu Leu Ser Arg Ile Asn His Phe
    50                  55                  60

Glu Lys Ile Gln Ile Ile Pro Lys Ser Ser Trp Ser Asp His Glu Ala
65                  70                  75                  80

Ser Ser Gly Val Ser Ser Ala Cys Pro Tyr Leu Gly Ser Pro Ser Phe
                85                  90                  95

Phe Arg Asn Val Val Trp Leu Ile Lys Lys Asn Ser Thr Tyr Pro Thr
            100                 105                 110

Ile Lys Lys Ser Tyr Asn Asn Thr Asn Gln Glu Asp Leu Leu Val Leu
        115                 120                 125

Trp Gly Ile His His Pro Lys Asp Ala Ala Glu Gln Thr Arg Leu Tyr
    130                 135                 140

Gln Asn Pro Thr Thr Tyr Ile Ser Ile Gly Thr Ser Thr Leu Asn Gln
145                 150                 155                 160

Arg Leu Val Pro Lys Ile Ala Thr Arg Ser Lys Val Asn Gly Leu Ser
                165                 170                 175

Ser Arg Met Glu Phe Phe Trp Thr Ile Leu Lys Pro Asn Asp Ala Ile
            180                 185                 190

Asn Phe Glu Ser Asn Gly Asn Phe Ile Ala Pro Glu Tyr Ala Tyr Lys
        195                 200                 205

Ile Val Lys Lys Gly Asp
    210
```

<210> SEQ ID NO 58
<211> LENGTH: 213
<212> TYPE: PRT
<213> ORGANISM: Influenza A virus

<400> SEQUENCE: 58

```
Pro Pro Leu Glu Leu Gly Asp Cys Ser Ile Ala Gly Trp Leu Leu Gly
1               5                   10                  15

Asn Pro Glu Cys Asp Arg Leu Leu Ser Val Pro Glu Trp Ser Tyr Ile
            20                  25                  30

Met Glu Lys Glu Asn Pro Arg Asn Gly Leu Cys Tyr Pro Gly Ser Phe
        35                  40                  45

Asn Asp Tyr Glu Glu Leu Lys His Leu Leu Ser Ser Val Lys His Phe
    50                  55                  60

Glu Lys Val Lys Ile Leu Pro Lys Asp Arg Trp Thr Gln His Thr Thr
65                  70                  75                  80

Thr Gly Gly Ser Gln Ala Cys Ala Val Ser Gly Asn Pro Ser Phe Phe
                85                  90                  95

Arg Asn Met Val Trp Leu Thr Lys Lys Gly Ser Asp Tyr Pro Val Ala
            100                 105                 110

Lys Gly Ser Tyr Asn Asn Thr Ser Gly Glu Gln Met Leu Ile Ile Trp
        115                 120                 125

Gly Val His His Pro Ile Asp Glu Thr Glu Gln Arg Thr Leu Tyr Gln
    130                 135                 140

Asn Val Gly Thr Tyr Val Ser Val Gly Thr Ser Thr Leu Asn Lys Arg
145                 150                 155                 160

Ser Thr Pro Glu Ile Ala Thr Arg Pro Lys Val Asn Gly Leu Gly Ser
                165                 170                 175

Arg Met Glu Phe Ser Trp Thr Leu Leu Asp Met Trp Asp Thr Ile Asn
            180                 185                 190

Phe Glu Ser Thr Gly Asn Leu Ile Ala Pro Glu Tyr Gly Phe Lys Ile
        195                 200                 205

Lys Arg Gly Ser Ser
    210
```

<210> SEQ ID NO 59
<211> LENGTH: 215
<212> TYPE: PRT
<213> ORGANISM: Influenza A virus

<400> SEQUENCE: 59

```
Ala Pro Leu His Leu Gly Lys Cys Asn Ile Ala Gly Trp Ile Leu Gly
1               5                   10                  15

Asn Pro Glu Cys Glu Ser Leu Ser Thr Ala Ser Ser Trp Ser Tyr Ile
            20                  25                  30

Val Glu Thr Pro Ser Ser Asp Asn Gly Thr Cys Tyr Pro Gly Asp Phe
        35                  40                  45

Ile Asp Tyr Glu Glu Leu Arg Glu Gln Leu Ser Ser Val Ser Ser Phe
    50                  55                  60

Glu Arg Phe Glu Ile Phe Pro Lys Thr Ser Ser Trp Pro Asn His Asp
65                  70                  75                  80

Ser Asn Lys Gly Val Thr Ala Ala Cys Pro His Ala Gly Ala Lys Ser
                85                  90                  95

Phe Tyr Lys Asn Leu Ile Trp Leu Val Lys Lys Gly Asn Ser Tyr Pro
            100                 105                 110
```

```
Lys Leu Ser Lys Ser Tyr Ile Asn Asp Lys Gly Lys Glu Val Leu Val
            115                 120                 125

Leu Trp Gly Ile His His Pro Ser Thr Ser Ala Asp Gln Gln Ser Leu
        130                 135                 140

Tyr Gln Asn Ala Asp Ala Tyr Val Phe Val Gly Ser Ser Arg Tyr Ser
145                 150                 155                 160

Lys Lys Phe Lys Pro Glu Ile Ala Ile Arg Pro Lys Val Arg Asp Gln
                165                 170                 175

Glu Gly Arg Met Asn Tyr Tyr Trp Thr Leu Val Glu Pro Gly Asp Lys
            180                 185                 190

Ile Thr Phe Glu Ala Thr Gly Asn Leu Val Val Pro Arg Tyr Ala Phe
            195                 200                 205

Ala Met Glu Arg Asn Ala Gly
            210                 215

<210> SEQ ID NO 60
<211> LENGTH: 214
<212> TYPE: PRT
<213> ORGANISM: Influenza A virus

<400> SEQUENCE: 60

Ala Pro Leu Gln Leu Gly Asn Cys Ser Val Ala Gly Trp Ile Leu Gly
1               5                   10                  15

Asn Pro Glu Cys Glu Leu Leu Ile Ser Arg Glu Ser Trp Ser Tyr Ile
            20                  25                  30

Val Glu Lys Pro Asn Pro Glu Asn Gly Thr Cys Tyr Pro Gly His Phe
        35                  40                  45

Ala Asp Tyr Glu Glu Leu Arg Glu Gln Leu Ser Ser Val Ser Ser Phe
    50                  55                  60

Glu Arg Phe Glu Ile Phe Pro Lys Glu Ser Ser Trp Pro Asn His Thr
65                  70                  75                  80

Thr Thr Gly Val Ser Ala Ser Cys Ser His Asn Gly Glu Ser Ser Phe
                85                  90                  95

Tyr Lys Asn Leu Leu Trp Leu Thr Gly Lys Asn Gly Leu Tyr Pro Asn
            100                 105                 110

Leu Ser Lys Ser Tyr Ala Asn Asn Lys Glu Lys Glu Val Leu Val Leu
        115                 120                 125

Trp Gly Val His His Pro Pro Asn Ile Gly Asp Gln Arg Ala Leu Tyr
    130                 135                 140

His Thr Glu Asn Ala Tyr Val Ser Val Val Ser Ser His Tyr Ser Arg
145                 150                 155                 160

Lys Phe Thr Pro Glu Ile Ala Lys Arg Pro Lys Val Arg Asp Arg Glu
                165                 170                 175

Gly Arg Ile Asn Tyr Tyr Trp Thr Leu Leu Glu Pro Gly Asp Thr Ile
            180                 185                 190

Ile Phe Glu Ala Asn Gly Asn Leu Ile Ala Pro Arg Tyr Ala Phe Ala
            195                 200                 205

Leu Ser Arg Gly Phe Gly
    210

<210> SEQ ID NO 61
<211> LENGTH: 209
<212> TYPE: PRT
<213> ORGANISM: Influenza A virus

<400> SEQUENCE: 61
```

```
Arg Ile Leu Asp Gly Ile Asp Cys Thr Leu Ile Asp Ala Leu Leu Gly
1               5                   10                  15
Asp Pro His Cys Asp Val Phe Gln Asn Glu Thr Trp Asp Leu Phe Val
                20                  25                  30
Glu Arg Ser Lys Ala Phe Ser Asn Cys Tyr Pro Tyr Asp Val Pro Asp
            35                  40                  45
Tyr Ala Ser Leu Arg Ser Leu Val Ala Ser Ser Gly Thr Leu Glu Phe
        50                  55                  60
Ile Thr Glu Gly Phe Thr Trp Thr Gly Val Thr Gln Asn Gly Gly Ser
65                      70                  75                  80
Asn Ala Cys Lys Arg Gly Pro Gly Ser Gly Phe Phe Ser Arg Leu Asn
                85                  90                  95
Trp Leu Thr Lys Ser Gly Ser Thr Tyr Pro Val Leu Asn Val Thr Met
            100                 105                 110
Pro Asn Asn Asp Asn Phe Asp Lys Leu Tyr Ile Trp Gly Ile His His
            115                 120                 125
Pro Ser Thr Asp Gln Glu Gln Thr Ser Leu Tyr Val Gln Ala Ser Gly
        130                 135                 140
Arg Val Thr Val Ser Thr Arg Arg Ser Gln Gln Thr Ile Ile Pro Asn
145                 150                 155                 160
Ile Gly Ser Arg Pro Trp Val Arg Gly Leu Ser Ser Arg Ile Ser Ile
                165                 170                 175
Tyr Trp Thr Ile Val Lys Pro Gly Asp Val Leu Val Ile Asn Ser Asn
            180                 185                 190
Gly Asn Leu Ile Ala Pro Arg Gly Tyr Phe Lys Met Arg Thr Gly Lys
        195                 200                 205
Ser
```